(12) United States Patent
Jung et al.

(10) Patent No.: US 8,815,778 B2
(45) Date of Patent: Aug. 26, 2014

(54) PH MODULATION METHOD TO DETECT LIGAND-RECEPTOR BINDING

(75) Inventors: Hyunsook Jung, Daejon (KR); Aaron D Robison, Bryan, TX (US); Paul S. Cremer, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 13/140,228

(22) PCT Filed: Dec. 18, 2009

(86) PCT No.: PCT/US2009/068854
§ 371 (c)(1), (2), (4) Date: Sep. 29, 2011

(87) PCT Pub. No.: WO2010/080640
PCT Pub. Date: Jul. 15, 2010

(65) Prior Publication Data
US 2012/0028823 A1    Feb. 2, 2012

Related U.S. Application Data

(60) Provisional application No. 61/217,366, filed on May 29, 2009, provisional application No. 61/203,198, filed on Dec. 18, 2008.

(51) Int. Cl.
*G01N 21/64* (2006.01)
*C07D 471/06* (2006.01)

(52) U.S. Cl.
CPC ............... *G01N 21/64* (2013.01); *C07D 471/06* (2013.01)
USPC .......................................... 506/9

(58) Field of Classification Search
USPC ................................. 506/7, 13, 23
See application file for complete search history.

(56) References Cited

U.S. PATENT DOCUMENTS

| | | |
|---|---|---|
| 5,798,276 A | 8/1998 | Haugland |
| 5,955,612 A | 9/1999 | Ahlem |
| 6,562,632 B1 | 5/2003 | Szalecki |
| 7,056,653 B2 | 6/2006 | Barenholz |
| 7,514,267 B1 | 4/2009 | Lopez |
| 2002/0039728 A1* | 4/2002 | Kain et al. .................. 435/6 |
| 2002/0177144 A1 | 11/2002 | Remacle |
| 2003/0099950 A1 | 5/2003 | Hanna |
| 2005/0233332 A1 | 10/2005 | Collis |
| 2008/0213133 A1 | 9/2008 | Wallace |
| 2008/0248492 A1 | 10/2008 | Yamazaki |

OTHER PUBLICATIONS

Corrie, J.E.T., et al., "Chemistry of Sulforhodamine-Amine Conjugates," Bioconjugate Chemistry 12(2):186-194, Mar. 2001.
Daniel, S., et al., "Separation of Membrane-Bound Compounds by Solid-Supported Bilayer Electrophoresis," J. Am. Chem. Soc. 129(26), 8072-8073, Jul. 2007.
Fears, K.P., et al., "Determination of the Surface pK of Carboxylic- and Amine-Terminated Alkanethiols Using Surface Plasmon Resonance Spectroscopy," Langmuir 24(3):837-843, Feb. 2008.
Fromherz, P., "Lipid Coumarin Dye as a Probe of Interfacial Electrical Potential in Biomembranes," in S. Fleischer and B. Fleischer (eds.), "Methods in Enzymology," vol. 171, Academic Press, Inc., San Diego, 1989, pp. 376-387.
Marchesini, S., et al., "Novel Fluorescent pH Indicator for the Acidic Range," Biochemistry International 27(3):545-550, Jul. 1992.
Sapuri, A.R., et al., "Electrostatically Targeted Intermembrane Lipid Exchange With Micropatterned Supported Membranes," Langmuir 19(5):1606-1610, Mar. 2003.
International Search Report and Written Opinion mailed Sep. 30, 2010, issued in corresponding International Application No. PCT/US2009/068854, filed Dec. 18, 2009, 8 pages.

\* cited by examiner

*Primary Examiner* — Jennifer McDonald
*Assistant Examiner* — Valerie Toodle
(74) *Attorney, Agent, or Firm* — Christensen O'Connor Johnson Kindness PLLC

(57) ABSTRACT

The present disclosure relates to detecting receptor-ligand binding by measuring local pH modulation using a pH-sensitive fluorophore.

60 Claims, 47 Drawing Sheets

150μm

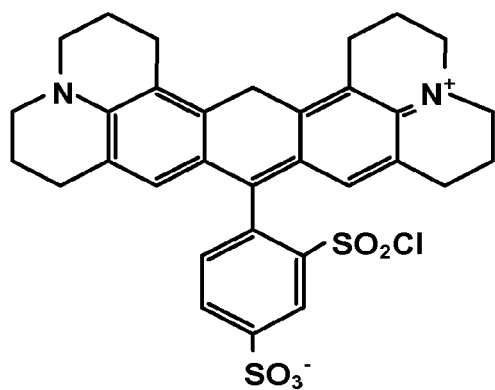
ORTHO-TEXAS RED SULFONYL CHLORIDE
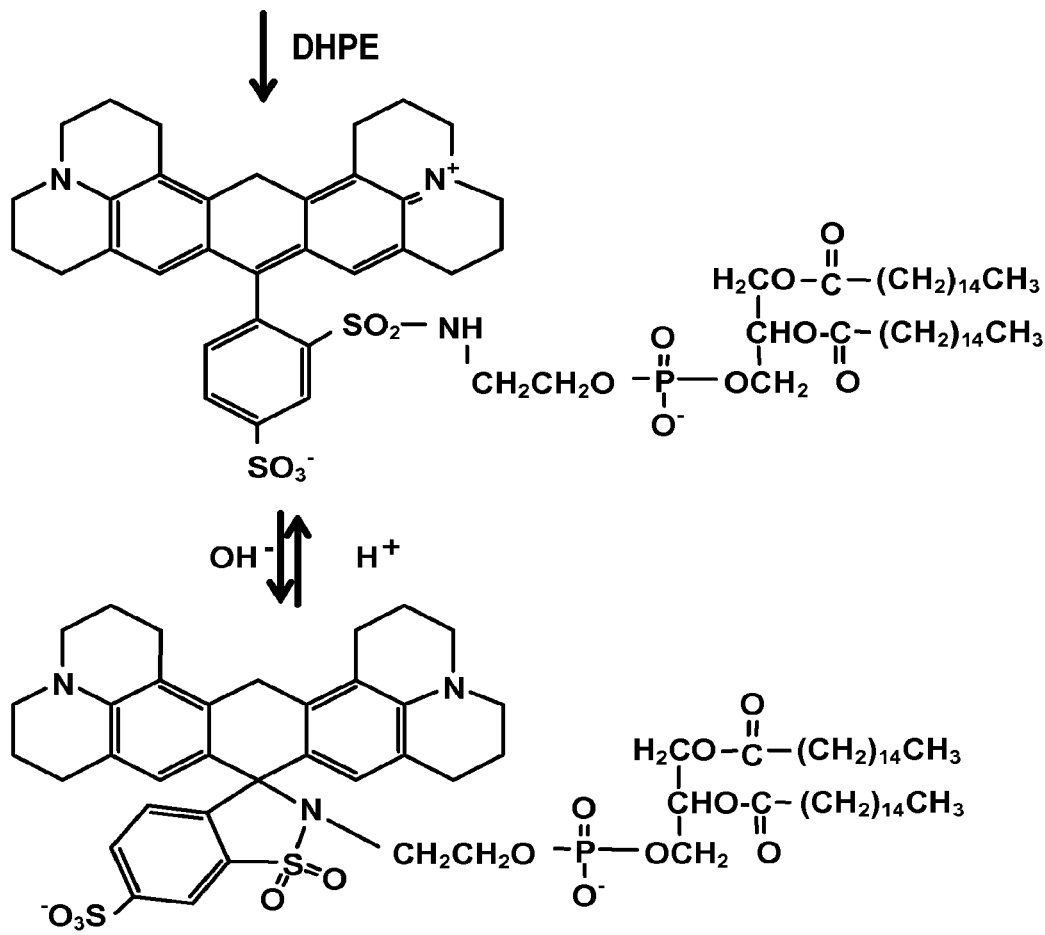
ORTHO-TEXAS RED DHPE
*Fig.14A.*

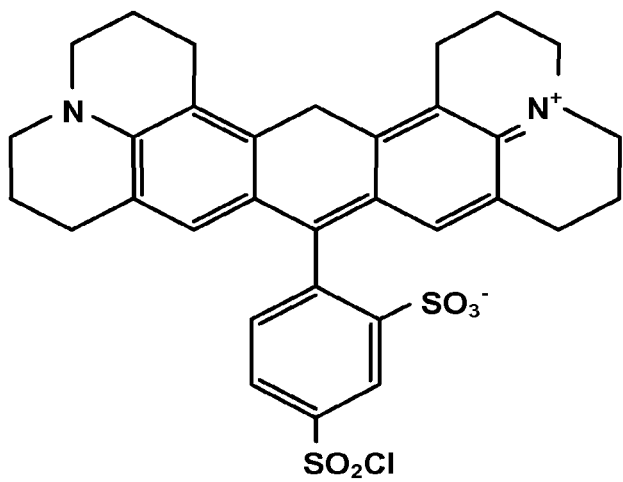
PARA-TEXAS RED SULFONYL CHLORIDE
↓ DHPE
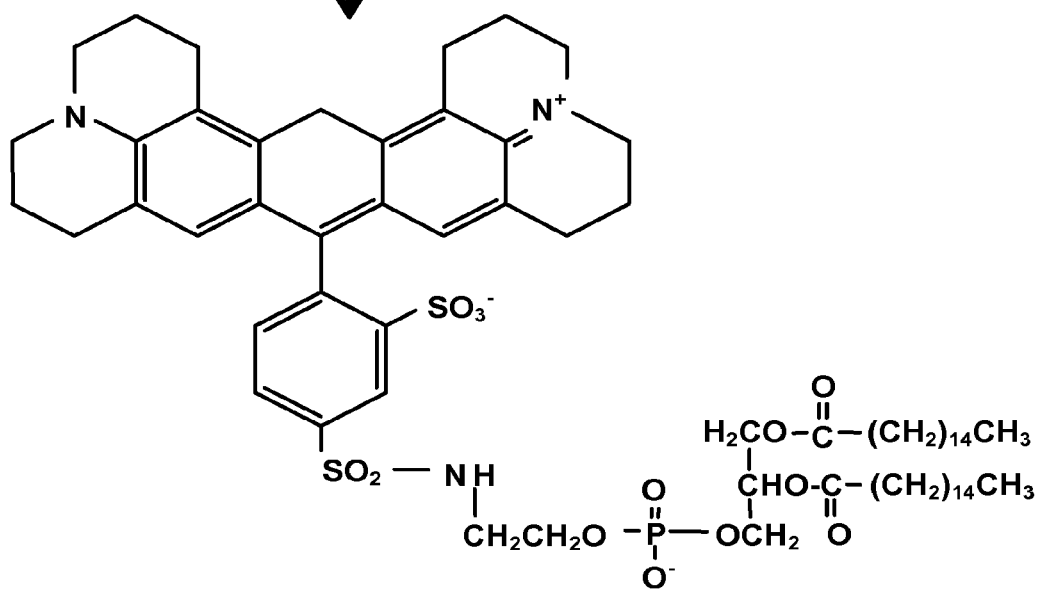
PARA-TEXAS RED DHPE
*Fig.14B.*

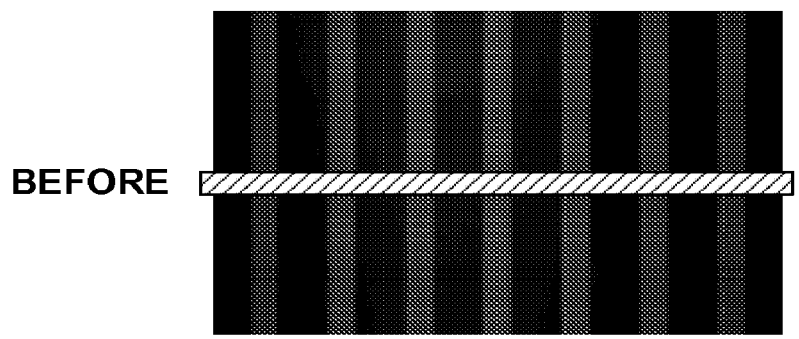
BEFORE
*Fig.18A1.*
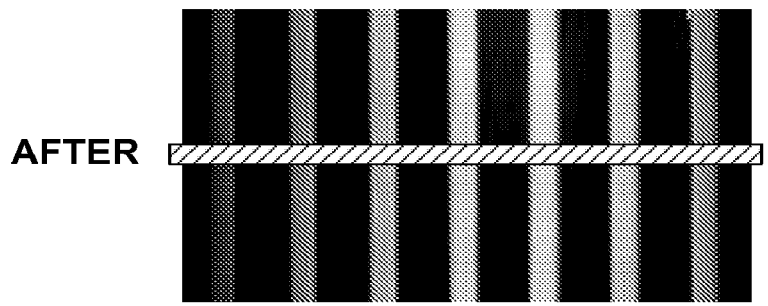
AFTER
*Fig.18A2.*
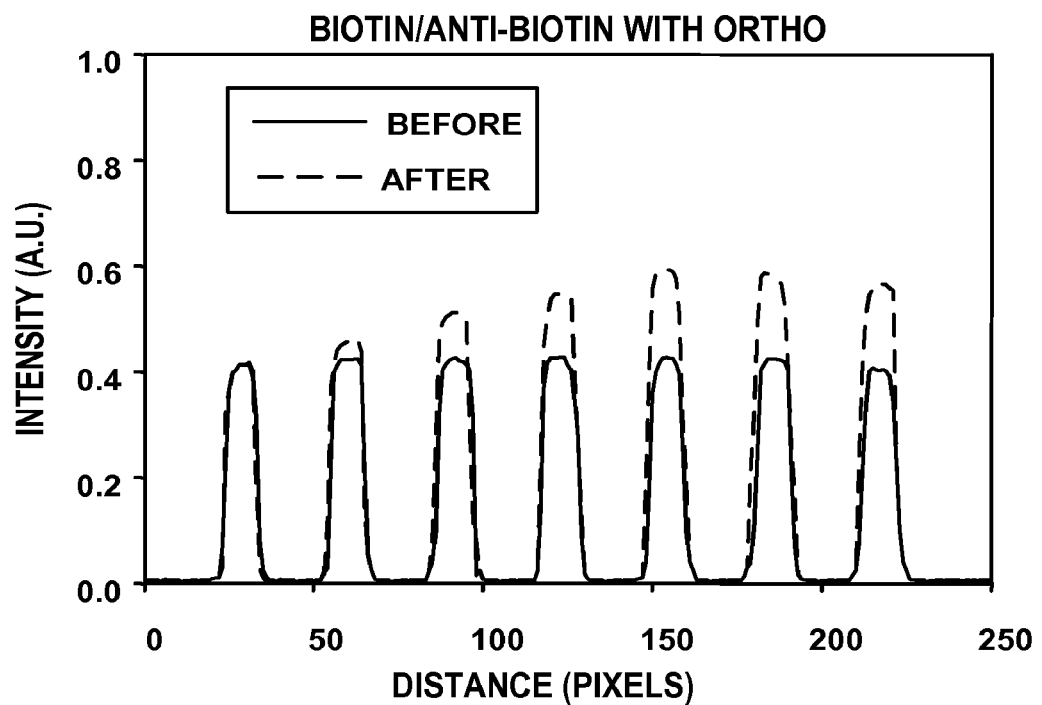
*Fig.18B.*

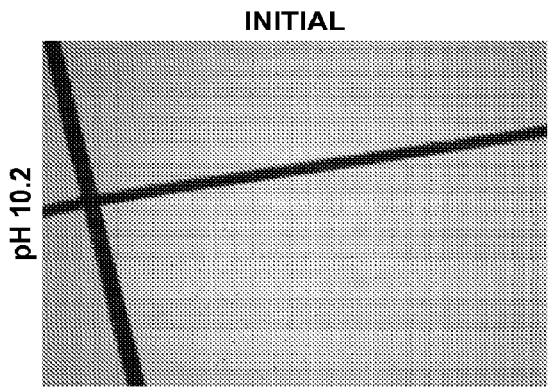
Fig.22A1.
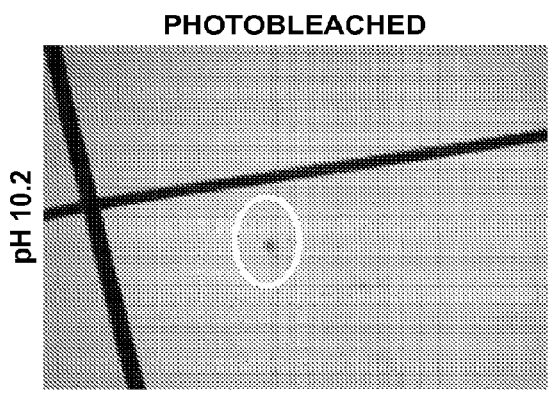
Fig.22A2.
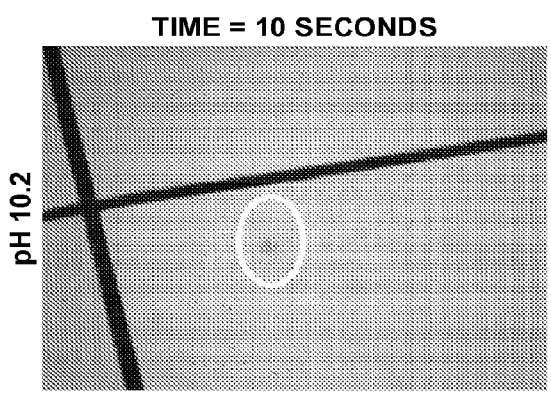
Fig.22A3.
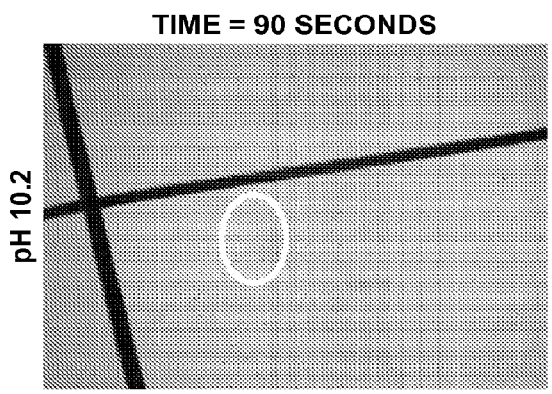
Fig.22A4.

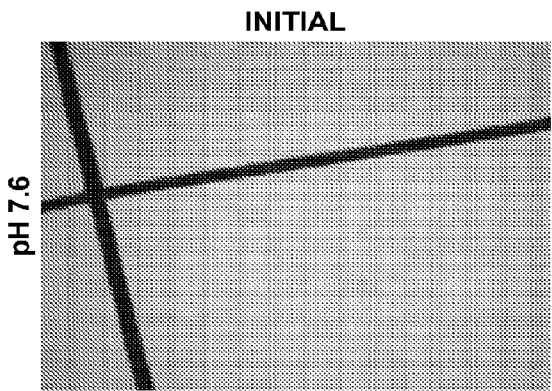
Fig.22B1.
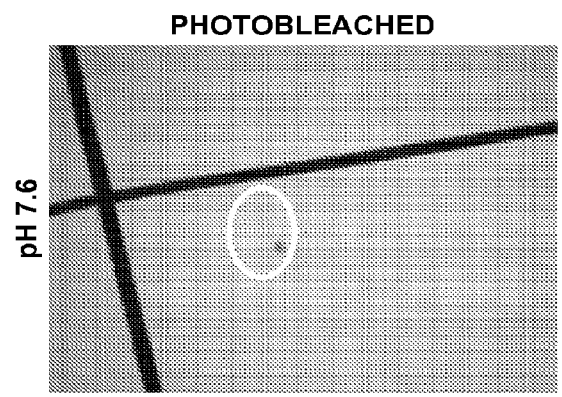
Fig.22B2.
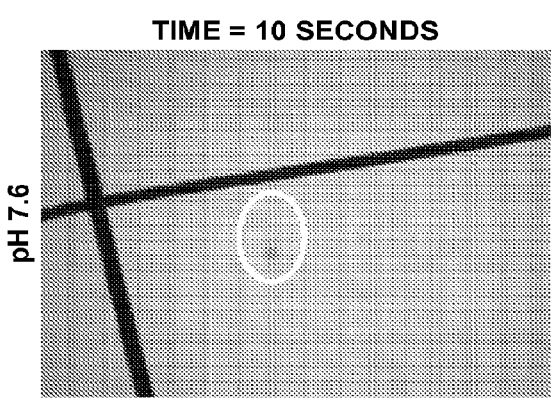
Fig.22B3.
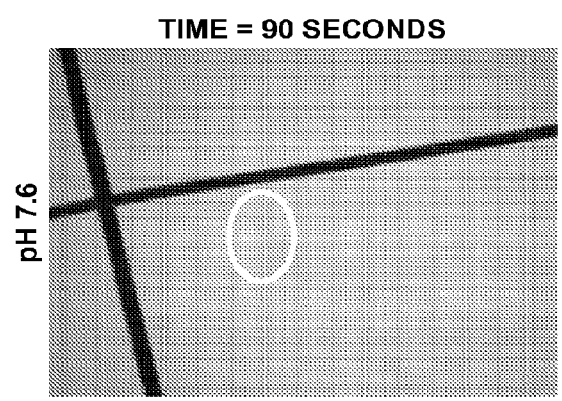
Fig.22B4.

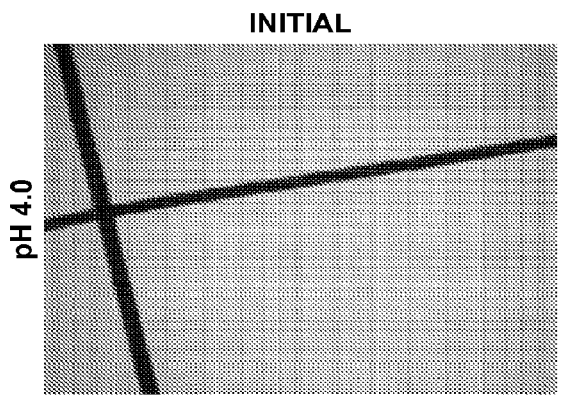
Fig.22C1.
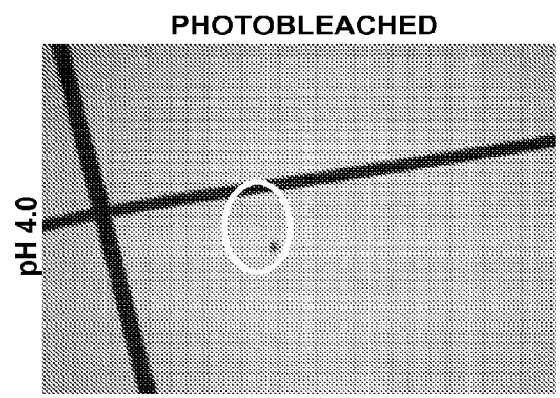
Fig.22C2.
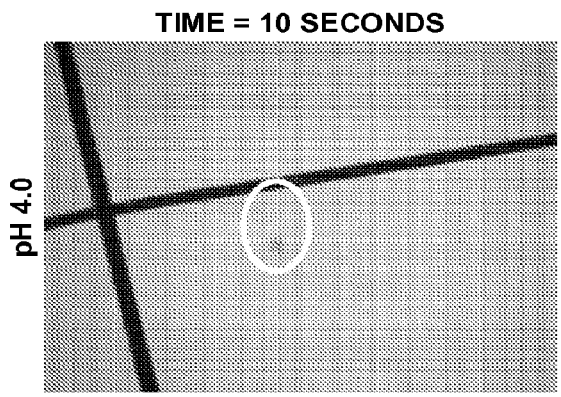
Fig.22C3.
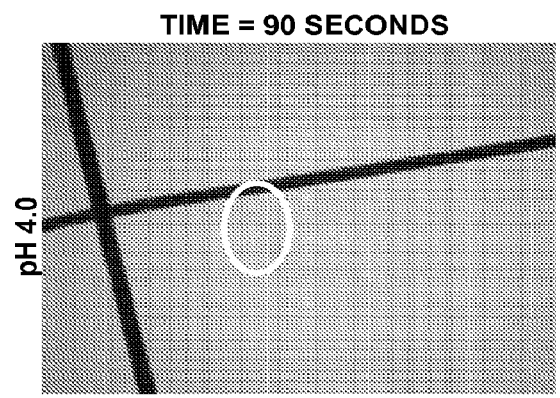
Fig.22C4.

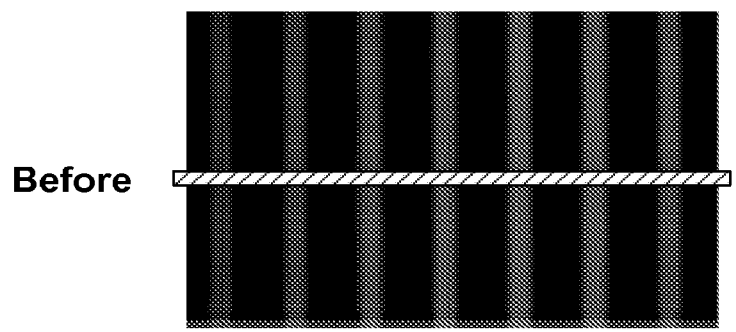
Before
*Fig.26A1.*
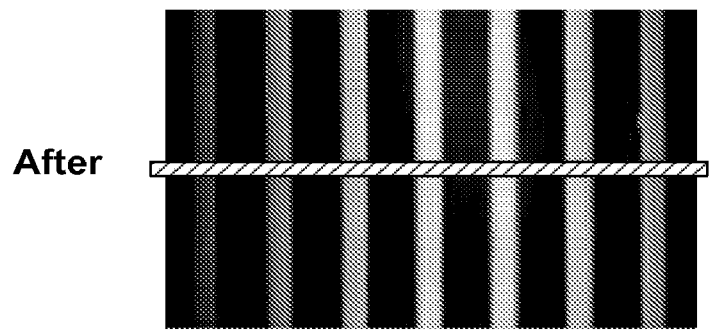
After
*Fig.26A2.*
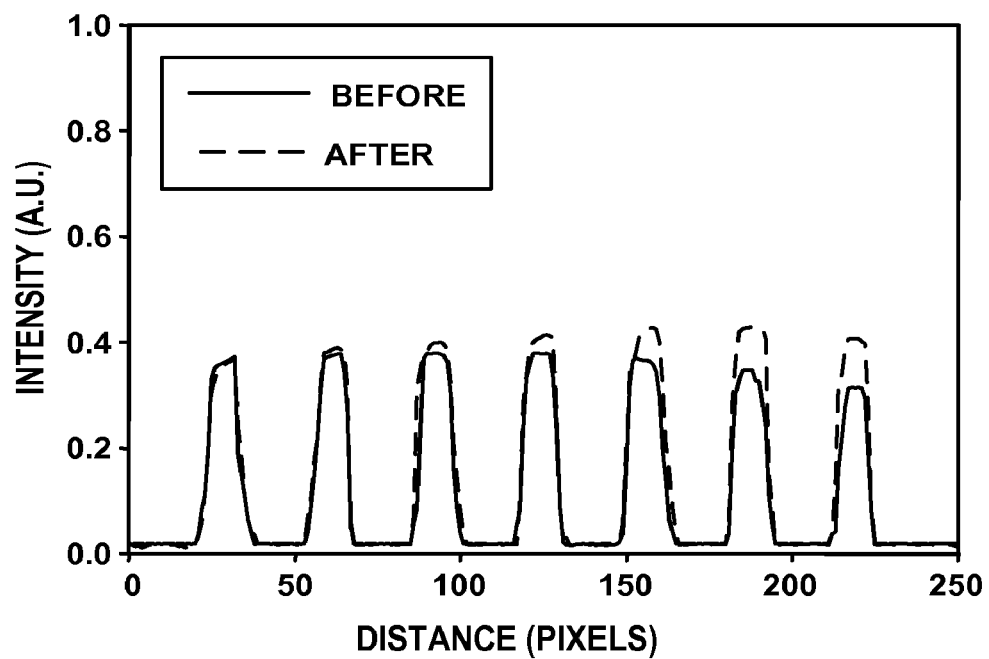
*Fig.26B.*

Skander and Ward et al., JACS 2004, 126, 14411

1-palmitoyl-2-oleoyl-sn-glycero-3-phosphocholine (POPC)
Neutral Lipid 1,2-Dioleoyl-sn-Glycero-3-Phospho-L-Serine (Sodium Salt) (DOPS)
Negative Lipid

PH MODULATION METHOD TO DETECT LIGAND-RECEPTOR BINDING

CROSS-REFERENCE TO RELATED APPLICATIONS

This application claims the benefit of U.S. Provisional Application No. 61/203,198, filed Dec. 18, 2008, and U.S. Provisional Application No. 61/217,366, filed May 29, 2009, each of which is incorporated herein by reference in its entirety.

RIGHTS IN THE INVENTION

This invention was made with government support under Grant No. N00014-08-1-0467 from the Office of Naval Research, Grant No. R01 GM070622 from the National Institutes of Health, and Grant No. W911NF-05-1-0494 from the Army Research Office. The government has certain rights in the invention.

FIELD OF THE DISCLOSURE

The present disclosure relates, in some embodiments; to analysis of receptor-ligand binding via pH modulation measurements. Accordingly, compositions, devices, systems, and methods regarding detection of receptor-ligand binding by local pH modulation are presented.

BACKGROUND

Techniques for monitoring ligand-receptor interactions are vital to a wide number of fields ranging from biotechnology to fundamental cell biology. Moreover, the associated sensing technologies may be of direct interest to the armed forces (e.g., the U.S. Navy). Such measurements are often made by fluorescently labeling proteins and nucleotides of interest. Indeed, fluorescent tags have become a ubiquitous tool for detecting protein-ligand interactions. (Soper, S. A., et al., *Anal. Chem.* 70:477 R-494R, 1998.) Labels can, however, interfere with the detection process and be extremely cumbersome to implement with real-time sensor devices. (Tan, P. K., et al., *Nucleic Acids Res.* 31:5676-5684, 2003.) This has been a major driving force behind the creation of assays that can detect biological analytes without labeling them (i.e., label-free detection). Methods for label-free detection include the use of liquid crystalline phase transitions (Kim, S. R. and N. L. Abbott, *Adv. Mater.* 13:1445-1449, 2001; Brake, J. M., et al., *Science* 302:2094-2097, 2003), colloidal particle imaging (Baksh, M. M., et al., *Nature* 427:139-141, 2004), semiconductor nanowire conductivity (Cui, Y. et al., *Science* 293:1289-1292, 2001; Patolsky, F., et al., *Anal. Chem.* 78:4260-4269, 2006; Wang, W. U., et al., *Proc. Natl. Acad. Sci. U.S.A.* 102:3208-3212, 2005), quartz crystal microbalance (QCM) measurements (Muratsugu, M., et al., *Anal. Chem.* 65:2933-2937, 1993; Cooper, M. A., et al., *Nat. Biotechnol.* 19:833-837, 2001; Yao, C. Y., et al., *J. Nanosci. Nanotech.* 6:3828-3834, 2006), and surface plasmon resonance (SPR) spectroscopy (Yang, C. Y., et al., *Lab on a Chip* 5:1017-1023, 2005; Kroger, D., et al., *Anal. Chem.* 71:3157-3165, 1999; Hoffman, T. L., et al., *Proc. Natl. Acad. Sci. U.S.A.* 97:11215-11220, 2000). These techniques, however, are not always easy to employ, can give a nonlinear response to the analyte, require specialized equipment, and/or suffer from poor sensitivity in comparison with fluorescence-based measurements (Song, X. D. and Swanson, B. I., *Anal. Chem.* 71:2097-2107, 1999).

SPR has perhaps become the most popular choice for label-free detection. This measurement, which is based upon changes in refractive index, requires a metal coated substrate (e.g., Au or Ag) and is performed in most cases by a dedicated and expensive commercial instrument (Markov, D. A., et al., *J. Am. Chem. Soc.* 126:16659-16664, 2004). The experiment is temperature sensitive and the signal abstracted is not necessarily linearly dependent on surface coverage. To make a measurement, one immobilizes a ligand on the metal substrate and flows a receptor over the surface. Under ideal conditions, the technique has an analyte detection limit in the low picomolar concentration range when the equilibrium dissociation constant for the ligand/receptor interaction is on the order of a few nanomolar (Yang, C. Y., et al., *Lab on a Chip* 5:1017-1023, 2005). SPR can be run in imaging mode to obtain many binding measurements simultaneously (multiplexing) (Brockman, J. M., et al., *J. Am. Chem. Soc.* 121:8044-8051, 1999; Wegner, G. J., et al., *Anal. Chem.* 74:5161-5168, 2002; Lee, H. J., et al., *Anal. Chem.* 78:6504-6510, 2006); however, the sensitivity is correspondingly poorer. In fact, SPR imaging sensitivity has been found to be on the order of 1 nM of bulk analyte for a 20 nM interaction (Lee, H. J., et al., *Anal. Chem.* 78:6504-6510, 2006). This has led to the development of subsequent chemical amplification steps in order to detect lower concentrations of analyte in solution (Li, Y., et al., *Anal. Chem.* 79:1082-1088, 2007). Other methodologies are needed that improve upon these inadequate detection thresholds and other deficiencies associated with label-free detection techniques.

SUMMARY OF THE INVENTION

The present disclosure relates to detecting receptor-ligand binding by measuring local pH modulation using a pH-sensitive fluorophore. Provided herein is a substrate comprising: (a) an ortho-sulforhodamine 101-conjugate; and (b) a ligand or a receptor, wherein the substrate is substantially free of para-sulforhodamine 101-conjugate. Also provided is a substrate comprising: (a) a para-sulforhodamine 101-conjugate; and (b) a ligand or a receptor, wherein the substrate is substantially free of ortho-sulforhodamine 101-conjugate. The present invention further provides a substrate comprising: (a) an ortho-sulforhodamine 101-conjugate; (b) a para-sulforhodamine 101-conjugate; and (c) a ligand or a receptor, wherein the ortho-sulforhodamine 101-conjugate and the para-sulforhodamine 101-conjugate are optically separated—that is, physically separated to a distance where they can be measured separately by microscopy. Also contemplated is a bead having a coating, wherein the coating comprises a surface that comprises an ortho-sulforhodamine 101-conjugate, such as the conjugate presented on the surface, wherein the bead is substantially free of para-sulforhodamine 101-conjugate. Some embodiments contemplate a bead having a coating, wherein the coating comprises a surface that comprises a para-sulforhodamine 101-conjugate, such as the conjugate presented on the surface, wherein the bead is substantially free of ortho-sulforhodamine 101-conjugate. Further contemplated is a bead having a coating, wherein the coating comprises a surface that comprises pH-sensitive dye, such as the dye presented on the surface, wherein the pH-sensitive dye is covalently bound to the coating and covalently bound to a first ligand or a first receptor. Dye and fluorophore are used interchangeably herein.

Some embodiments also provide a system for detecting receptor-ligand binding, comprising: (a) a multi-well plate; and (b) a bead, as described herein. In some embodiments, a microfluidic device is provided, comprising at least two channels, wherein one channel comprises an ortho-sulforhodamine 101-conjugate wherein the one channel is substantially free of para-sulforhodamine 101-conjugate, and a second channel comprises a para-sulforhodamine 101-conjugate wherein the second channel is substantially free of ortho-sulforhodamine 101-conjugate.

Also contemplated is a method of detecting binding between a non-fluorescently labeled ligand and a non-fluorescently labeled receptor, comprising: introducing a substrate comprising both a pH-sensitive fluorophore and the non-fluorescently labeled ligand to a solution comprising the non-fluorescently labeled receptor; and observing a change, if any, in fluorescence as reported by the pH-sensitive fluorophore, wherein a change in fluorescence is indicative of binding. The pH-sensitive fluorophore and the non-fluorescently labeled ligand may each be presented on the surface of the substrate (e.g., the same surface). Other embodiments contemplate a method of detecting binding between a non-fluorescently labeled ligand and a non-fluorescently labeled receptor, comprising: introducing a substrate comprising both a pH-sensitive fluorophore and the non-fluorescently labeled receptor to a solution comprising the non-fluorescently labeled ligand; and observing a change, if any, in fluorescence as reported by the pH-sensitive fluorophore, wherein a change in fluorescence is indicative of binding. The pH-sensitive fluorophore and the non-fluorescently labeled receptor may each presented on a surface (e.g., the same surface) of the substrate.

Some embodiments contemplate a method of detecting binding between a non-fluorescently labeled receptor and a non-fluorescently labeled ligand, comprising: obtaining a first fluorescence measurement associated with a substrate or a solution (i.e., a first solution) comprising both a pH-sensitive fluorophore and the non-fluorescently labeled receptor; introducing a (second) solution comprising the non-fluorescently labeled ligand to the substrate; and obtaining a second fluorescence measurement, wherein a change in fluorescence between the first and second measurements is indicative of binding.

Some embodiments contemplate a method of detecting binding between a non-fluorescently labeled ligand and a non-fluorescently labeled receptor, comprising: obtaining a first fluorescence measurement associated with a substrate or a solution (i.e., a first solution) comprising both a pH-sensitive fluorophore and the non-fluorescently labeled ligand; introducing a (second) solution comprising the non-fluorescently labeled receptor to the substrate; and obtaining a second fluorescence measurement, wherein a change in fluorescence between the first and second measurements is indicative of binding.

The present invention further provides a method of detecting receptor-ligand binding comprising contacting a receptor with a ligand in the presence of an ortho-sulforhodamine 101-conjugate, wherein the ortho-sulforhodamine 101-conjugate is optically separated (i.e., separated to a physical distance beyond the diffraction limit) from a para-sulforhodamine 101-conjugate, and wherein a change in fluorescence of the ortho-sulforhodamine 101-conjugate indicates binding. Also provided is a method of determining whether the ligand or the receptor of a substrate binds to a cognate receptor or cognate ligand, respectively, the method comprising: introducing the substrate to a bulk aqueous solution comprising a cognate receptor or cognate ligand; and observing a change, if any, in fluorescence as reported by an ortho-sulforhodamine 101-conjugate, such as the conjugate presented on the surface of the substrate, wherein a change in fluorescence is indicative of binding.

Some embodiments contemplate a method of determining whether the ligand of a substrate binds to a cognate receptor or whether the receptor of a substrate binds to a cognate ligand, the method comprising: obtaining a first fluorescence measurement associated with the substrate; introducing the substrate to a bulk aqueous solution comprising a cognate receptor or cognate ligand; and obtaining a second fluorescence measurement, wherein a change in fluorescence between the first and second measurements is indicative of binding.

Also provided is a method of detecting binding between a ligand and a receptor, comprising: obtaining a first fluorescence measurement of a first solution comprising a ortho-sulforhodamine 101-labeled receptor, wherein the solution is substantially free of para-sulforhodamine 101-conjugate; introducing a second solution comprising a ligand; and obtaining a second fluorescence measurement, wherein a change in fluorescence between the first and second measurements is indicative of binding.

Further provided is a method of determining a kinetic measurement of a receptor-ligand binding event comprising contacting an ortho-sulforhodamine 101 labeled protein with a ligand, wherein $k_{on}$ for the binding event is determined.

As discussed above, a need has arisen for improved compositions, devices, systems, and methods for detecting biomolecule-ligand binding, such as on a solid-liquid interface. Examples of biomolecules include, without limitation, proteins and viruses. Examples of solid-liquid interfaces include, without limitation, glass beads, polymer beads, oxide substrates, semiconductor substrates, plastic substrates, and/or supported bilayers. The present disclosure relates, according to some embodiments, to compositions, devices, systems, and methods for detecting protein-ligand binding and/or virus-ligand binding on glass beads, polymer beads, oxide substrates, semiconductor substrates, plastic substrates, or supported bilayers by local pH modulation. For example, in some embodiments, a pH sensitive assay may be configured for use with one or more fluorescent bead platforms. Micron scale beads may be made by employing silane chemistry to attach pH sensitive dye molecules and ligands. Beads may be used in a standard 96 well assay and read out with a standard fluorescence plate reader. Embodiments of this assay may be optimized for the lowest possible limits of detection and maximum resistance to non-specific protein adsorption.

DESCRIPTION OF THE DRAWINGS

Some embodiments of the disclosure may be understood by referring, in part, to the present disclosure and the accompanying drawings, which illustrate one or more specific example embodiments.

FIG. 14. (a) The ortho and (b) para forms of Texas Red® sulfonyl chloride are shown at the top. Both isomers can be conjugated to a primary amine (DHPE in this case). The ortho isomer forms a five membered ring upon deprotonation of the sulfonamide by attacking the xanthylium ring system (a). The para isomer does not undergo an equivalent reaction because of geometric constraints (b).

FIG. 22. Images and photobleaching data for SLBs composed of 99.47 mol % POPC/0.5 mol % biotin-cap-PE/~0.03 mol % ortho-Texas Red® DHPE (pH insensitive dye). Bilayers were initially formed in PBS buffer at pH 7.6. (a) The bulk solution was exchanged with a buffer solution at pH 10.2 before photobleaching. (b) Same measurement as in (a), but after lowering the pH to 7.6. (c) Same measurement as in (a), but after lowering the pH to 4.0. The red circles highlight the position where the bleaching spots were made.

DETAILED DESCRIPTION OF THE INVENTION

Figure 1:
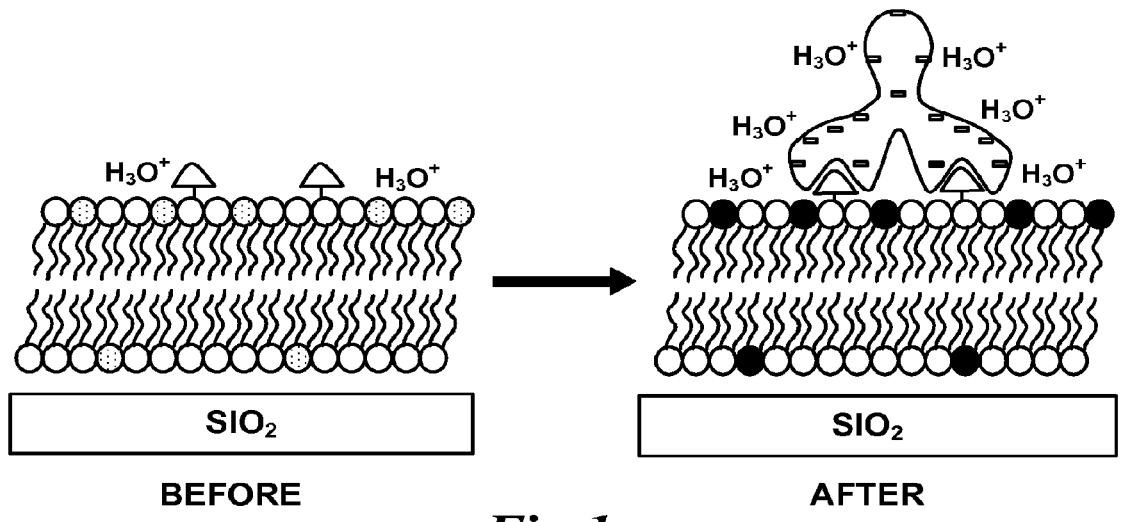
FIG. 1. Schematic diagram illustrating the principle of a pH sensitive dye as a reporter for interfacial binding of negatively charged proteins. (Before) In the absence of proteins, the dye molecules fluoresce relatively weakly. (After) Upon specific protein binding, the dye molecules fluoresce strongly.

The present disclosure relates to detecting receptor-ligand binding by measuring local pH modulation using a pH-sensitive fluorophore. In some embodiments, detection methods are provided where there is not a need for labeling either member of a receptor-ligand binding pair, though either may optionally be labeled. The present disclosure provides, in some embodiments, assays that are straight-forward to employ and compatible with equipment that is already available in many laboratories. According to some embodiments, assays may achieve results close to single molecule sensitivity while being compatible with an array-based readout.

Accordingly, the present invention provides, in some embodiments, a substrate comprising: (a) an ortho-sulforhodamine 101-conjugate; and (b) a ligand or a receptor, wherein the substrate is substantially free of para-sulforhodamine 101-conjugate.

In some embodiments, the substrate is planar. The substrate may comprise plastic, glass (e.g., borosilicate), silica, mica, sapphire, a polymer, or an oxide, or a combination thereof. Non-limiting examples of oxides include alumina and $TiO_2$, and others are known in the art. The substrate may comprise a polymer, such as polydimethylsiloxane (PDMS). In some embodiments, PDMS is exposed to an oxygen plasma such that the surface is hydrophilic. In some embodiments, the PDMS is used within about fifteen minutes of being exposed to an oxygen plasma for this purpose. In some embodiments, the substrate comprises a semiconductor. The substrate may comprise a lipid. In some embodiments, the substrate comprises a supported lipid bilayer. In some embodiments, the substrate is free of any other fluorophore or fluorophore-containing conjugate. The substrate may be a well of a multi-well plate (e.g., 96-well or 384-well). The substrate may be comprised in a device, such as a microfluidic device. For example, the substrate may be the surface of a microfluidic device.

In some embodiments, a substrate is further defined as a bead. The skilled artisan will realize that the invention is not limited to spherical beads and any shaped bead or particle may be used. The terms "bead" and "particle" are used interchangeably herein to signify that any shaped bead or particle may be used in the invention. Beads may be spherical but may also be other shapes, such as ovals, cubes, closed cylinders and irregular shapes. Beads may be porous or non-porous: A bead may be a silica bead or a polystyrene bead. The diameter of a bead may range from about 0.05 μm to about 100 μm. In some embodiments, the diameter ranges from about, at most about, or at least about 0.05, 0.1, 0.5, 1.0, 10, 50, or 100 μm, or any range derivable therein. A bead may be substantially covered by a coating. The coating may be a protein-resistant coating, which, as is known in the art, is a material that resists the binding of a protein. The protein-resistant coating may comprise zwitterionic lipids, polyethyleneglycol (PEG), or a mixture thereof. Molecular weights of PEG may range from small oligomers (e.g., a 5-mer) to values (e.g., $PEG^{10,000}$). An ortho-sulforhodamine 101-conjugate may be immobilized on the coating. A conjugate may be immobilized such that the ortho-sulforhodamine 101 is presented on the surface of the coating. In some embodiments, the ortho-sulforhodamine 101-conjugate is covalently bound to the coating such that the ortho-sulforhodamine 101 is presented on the surface of the coating.

In some embodiments, the ortho-sulforhodamine 101-conjugate may comprise the ligand or receptor to form an ortho-sulforhodamine 101-labeled ligand or an ortho-sulforhodamine 101-labeled receptor. In some embodiments, the ortho-sulforhodamine 101-conjugate comprises the receptor to form an ortho-sulforhodamine 101-labeled receptor. The ortho-sulforhodamine 101-conjugate may be covalently bound to the substrate such that the ortho-sulforhodamine 101 is presented on the surface of the coating. ortho-Sulforhodamine 101 may be covalently bound to the substrate and to either the ligand or the receptor.

In some embodiments, the ortho-sulforhodamine 101-conjugate comprises a lipid, such as DHPE. The ortho-sulforhodamine 101-conjugate may be further defined as ortho-sulforhodamine 101-DHPE. In some embodiments, the ortho-sulforhodamine 101-conjugate comprises a polymer, such as PEG. The ortho-sulforhodamine 101-conjugate may be further defined as ortho-sulforhodamine 101-PEG-trialkoxysilane.

In some embodiments, ortho-sulforhodamine 101, para-sulforhodamine 101, an ortho-sulforhodamine 101-conjugate, a para-sulforhodamine 101-conjugate, or a pH-sensitive fluorophore as described herein is not encapsulated. For example, in some embodiments, the conjugated or unconjugated fluorophore is not encapsulated in a solution in a liposome, bead, or other encapsulating body. In some embodiments, the conjugated or unconjugated fluorophore is not encapsulated by means of being presented on the interior surface of a liposome, bead, or other encapsulating body. In some embodiments, the detection of a change of fluorescence takes place external to a liposome, bead, or other encapsulating body. In some embodiments, the ligand does not comprise a fluorophore. In some embodiments, the receptor does not comprise a fluorophore. In some embodiments, the ligand is not a metal ion. In some embodiments, a receptor is a non-fluorescently labeled receptor. In some embodiments, a ligand is a non-fluorescently labeled ligand. In some embodiments, a change in fluorescence upon receptor-ligand binding is not dependent upon the release of a species from a substrate. In some embodiments, a fluorophore presented on the surface of a bead or other substrate is not coated with a second lipid layer, such as described by U.S. Pat. No. 7,514,267, incorporated herein by reference. In some embodiments, a coating on a substrate is not a metal coating.

The present invention also contemplates a substrate comprising: (a) a para sulforhodamine 101-conjugate; and (b) a ligand or a receptor, wherein the substrate is substantially free of ortho-sulforhodamine 101-conjugate.

Also contemplated is a substrate comprising: (a) an ortho-sulforhodamine 101-conjugate; (b) a para-sulforhodamine 101-conjugate; and (c) a ligand or a receptor, wherein the ortho-sulforhodamine 101-conjugate and the para-sulforhodamine 101-conjugate are optically separated.

In some embodiments, the present invention contemplates a bead having a coating, wherein the coating comprises a surface that comprises an ortho-sulforhodamine 101-conjugate, such as the conjugate presented on the surface, wherein the bead is substantially free of para-sulforhodamine 101-conjugate. The ortho-sulforhodamine 101-conjugate may be immobilized on the coating such that the fluorophore is presented on the surface of the coating. The ortho-sulforhodamine 101-conjugate may be covalently bound to the coating such that the fluorophore is presented on the surface of the coating. The coating may be a protein-resistant coating, as described above. Indeed, the coating may be any coating described herein. The coating may comprise PEG. The coating may further comprise either a first ligand or a first receptor presented on the surface. The first ligand or the first receptor may be covalently bound to the coating such that it is presented on the surface of the coating. The ortho-sulforhodamine 101-conjugate may be covalently bound to the coating and covalently bound to a first ligand or a first receptor, such that the fluorophore and either the ligand or receptor are each presented on the surface of the coating.

Also contemplated is a bead having a coating, wherein the coating comprises a surface that comprises a para-sulforhodamine 101-conjugate, such as the conjugate presented on the surface, wherein the bead is substantially free of ortho-sulforhodamine 101-conjugate. The coating may be of any type discussed herein.

Also contemplated is a bead having a coating, wherein the coating comprises a surface that comprises pH-sensitive dye, such as the dye presented on the surface, wherein the pH-sensitive dye is covalently bound to the coating and covalently bound to a first ligand or a first receptor. The coating may be of any type discussed herein.

Systems are also contemplated by the present invention. For example, some embodiments contemplate a system for detecting receptor-ligand binding, comprising: (a) a multi-well plate; and (b) a bead as described herein. The multi-well plate may be a 96- or a 384-well plate. The system may be configured to detect binding of a minimum of about 50 molecules per pixel. The system may be configured to detect binding of a minimum of about 1 part in 3,000,000 of the receptor-ligand $K_d$. Indeed, in any embodiment herein, receptor-ligand binding detection may be about, at least about, or at most about 1 part in 30,000,000, 1 part in 3,000,000, 1 part in 300,000, 1 part in 30,000, or 1 part in 3,000, or any range derivable therein, of the receptor-ligand $K_d$. The system may be configured to operate within a pH range of about 2 to about 13. Indeed, in some embodiments, detection may occur at a pH of about, at most about, 2, 2.5, 3, 3.5, 4, 4.5, 5, 5.5, 6, 6.5, 7, 7.5, 8, 8.5, 9, 9.5, 10, 10.5, 11, 11.5, 12, 12.5, or 13, or any range derivable therein. As is known in the art, different pH-sensitive dyes will operate in different pH conditions. For example, use of ortho-sulforhodamine 101 and its conjugates will typically occur in a range of about 5-9.

Devices, such as microfluidic devices, are also contemplated herein. For example, some embodiments contemplate a microfluidic device comprising at least two channels, wherein one channel comprises an ortho-sulforhodamine 101-conjugate wherein the one channel is substantially free of para-sulforhodamine 101-conjugate, and a second channel comprises a para-sulforhodamine 101-conjugate wherein the second channel is substantially free of ortho-sulforhodamine 101-conjugate. The conjugates may be immobilized to the surface of either channel, as appropriate. In some embodiments, the ortho-sulforhodamine 101-conjugate is covalently bound to the surface of one channel, and the para-sulforhodamine 101-conjugate is covalently bound to the surface of the second channel. Any bead described herein may be immobilized on a surface of a channel. For example, a bead having a coating, wherein the coating comprises a surface that comprises an ortho-sulforhodamine 101-conjugate, such as the conjugate presented on the surface, wherein the bead is substantially free of para-sulforhodamine 101-conjugate, may be immobilized on the surface of one channel, and a bead having a coating, wherein the coating comprises a surface that comprises a para-sulforhodamine 101-conjugate, such as the conjugate presented on the surface, wherein the bead is substantially free of ortho-sulforhodamine 101-conjugate, may be immobilized to the surface of the second channel.

Methods are also contemplated by the present invention. For example, provided is a method of detecting binding between a non-fluorescently labeled ligand and a non-fluorescently labeled receptor, comprising: introducing a substrate comprising both a pH-sensitive fluorophore and the non-fluorescently labeled ligand to a solution comprising the non-fluorescently labeled receptor; and observing a change, if any, in fluorescence as reported by the pH-sensitive fluorophore, wherein a change in fluorescence is indicative of binding. The pH-sensitive fluorophore and the non-fluorescently labeled ligand may each be presented on the surface of the substrate (e.g., the same surface). In this or any embodiment herein, the detection limit may be as discussed above.

Also contemplated is a method of detecting binding between a non-fluorescently labeled ligand and a non-fluorescently labeled receptor, comprising: introducing a substrate comprising both a pH-sensitive fluorophore and the non-fluorescently labeled receptor to a solution comprising the non-fluorescently labeled ligand; and observing a change, if any, in fluorescence as reported by the pH-sensitive fluorophore, wherein a change in fluorescence is indicative of binding. The pH-sensitive fluorophore and the non-fluorescently labeled receptor may each be presented on the surface (e.g., the same surface) of the substrate.

Further contemplated is a method of detecting receptor-ligand binding comprising contacting a receptor with a ligand in the presence of an ortho-sulforhodamine 101-conjugate, wherein the ortho-sulforhodamine 101-conjugate is optically separated from a para-sulforhodamine 101-conjugate, and wherein a change in fluorescence of the ortho-sulforhodamine 101-conjugate indicates binding. In this or any embodiment herein, a method may further comprise employing para-sulforhodamine 101 or a para-sulforhodamine 101-conjugate as a reference. Exemplary methods of employing such a reference are described herein.

In some embodiments, the receptor is immobilized on a substrate, such as covalently bound to a substrate, and the ligand is present in a bulk aqueous phase that is introduced to the bound receptor. In some embodiments, a method further comprises a step of immobilizing the receptor to the substrate, such as covalently binding the receptor to the substrate.

In some embodiments, the ligand is immobilized on a substrate, such as covalently bound to a substrate, and the receptor is present in a bulk aqueous phase that is introduced to the bound ligand. In some embodiments, a method further comprises a step of immobilizing the ligand to the substrate, such as covalently binding the ligand to the substrate.

A method may be further defined as a high throughput screening method.

In some embodiments herein, an ortho-sulforhodamine 101-conjugate may comprise the ligand or receptor to form an ortho-sulforhodamine 101-labeled ligand or an ortho-sulforhodamine 101-labeled receptor. The ortho-sulforhodamine 101-conjugate may be immobilized on a substrate, in some embodiments.

In some embodiments, a method may further comprise improving receptor-ligand detection by increasing the mole percentage of the ortho-sulforhodamine 101-conjugate immobilized to a substrate.

Also contemplated is a method of determining whether the ligand or the receptor of a substrate binds to a cognate receptor or cognate ligand, respectively, the method comprising: introducing the substrate to a bulk aqueous solution comprising or thought to comprise a cognate receptor or cognate ligand; and observing a change, if any, in fluorescence as reported by an ortho-sulforhodamine 101-conjugate, such as the conjugate presented on the surface of the substrate, wherein a change in fluorescence is indicative of binding. This or any other method described herein may further comprise employing the para-sulforhodamine 101-conjugate as a reference. In some embodiments, a method may further comprise immobilizing the ortho-sulforhodamine 101-conjugate onto the substrate. A method may further comprise immobilizing the ligand or receptor onto the substrate.

A method may also comprise the addition of positively or negatively charged lipids to a supported lipid bilayer such that the pH-sensitive fluorophore employed in the method reacts differently to a receptor-ligand binding event.

Some embodiments contemplate a method of detecting binding between a non-fluorescently labeled receptor and a non-fluorescently labeled ligand, comprising: obtaining a first fluorescence measurement associated with a substrate comprising both a pH-sensitive fluorophore and the non-fluorescently labeled receptor; introducing a solution comprising the non-fluorescently labeled ligand to the substrate; and obtaining a second fluorescence measurement, wherein a change in fluorescence between the first and second measurements is indicative of binding. The detection limit may about 1 part in 3,000,000 of the receptor-ligand $K_d$. The pH-sensitive fluorophore may be an ortho-sulforhodamine 101-conjugate. The ortho-sulforhodamine 101-conjugate may optically separated from a para-sulforhodamine 101-conjugate. The para-sulforhodamine 101-conjugate may be employed as a reference.

Further provided is a method of detecting binding between a non-fluorescently labeled ligand and a non-fluorescently labeled receptor, comprising: obtaining a first fluorescence measurement associated with a substrate comprising both a pH-sensitive fluorophore and the non-fluorescently labeled ligand; introducing a solution comprising the non-fluorescently labeled receptor to the substrate; and obtaining a second fluorescence measurement, wherein a change in fluorescence between the first and second measurements is indicative of binding. The detection limit may about 1 part in 3,000,000 of the receptor-ligand $K_d$. The pH-sensitive fluorophore may be an ortho-sulforhodamine 101-conjugate. The ortho-sulforhodamine 101-conjugate may optically separated from a para-sulforhodamine 101-conjugate. The para-sulforhodamine 101-conjugate may be employed as a reference.

Also provided is a method of determining whether the ligand of a substrate binds to a cognate receptor or whether the receptor of a substrate binds to a cognate ligand, the method comprising: obtaining a first fluorescence measurement associated with the substrate; introducing the substrate to a bulk aqueous solution comprising a cognate receptor or cognate ligand; and obtaining a second fluorescence measurement, wherein a change in fluorescence between the first and second measurements is indicative of binding.

In some embodiments, such as some methods, the receptor is a non-fluorescently labeled receptor. In some embodiments, such as some methods, the ligand is a non-fluorescently labeled ligand. In some embodiments, such as some methods, the receptor is covalently bound to a substrate. The ligand may be present in a bulk aqueous phase that is introduced to the bound receptor. A method may further comprise covalently binding the receptor to the substrate. In some embodiments, such as some methods, the ligand is covalently bound to a substrate. In some embodiments, such as some methods, the receptor is present in a bulk aqueous phase that is introduced to the bound ligand. A method may further comprise covalently binding the ligand to the substrate. In some embodiments, such as some methods, the ortho-sulforhodamine 101-conjugate comprises the ligand or receptor to form an ortho-sulforhodamine 101-labeled ligand or an ortho-sulforhodamine 101-labeled receptor. In some embodiments, such as some methods, the ortho-sulforhodamine 101-conjugate is immobilized on a substrate. A method may further comprise increasing the concentration of the ortho-sulforhodamine 101-conjugate by increasing the mole percentage of the conjugate immobilized to the substrate.

Further contemplated is a method of detecting binding between a ligand and a receptor, comprising: obtaining a first fluorescence measurement of a first solution comprising a ortho-sulforhodamine 101-labeled receptor, wherein the solution is substantially free of para-sulforhodamine 101-conjugate; introducing a second solution comprising a ligand; and obtaining a second fluorescence measurement, wherein a change in fluorescence between the first and second measurements is indicative of binding. The method may further comprising employing para-sulforhodamine 101-conjugate as a reference.

Some embodiments contemplate a method of detecting binding between a non-fluorescently labeled receptor, or a receptor labeled only with ortho-sulforhodamine 101 or para-sulforhodamine 101, and a non-fluorescently labeled ligand, comprising: obtaining a first fluorescence measurement associated with a substrate comprising both a pH-sensitive fluorophore and the non-fluorescently labeled receptor, or a receptor labeled only with ortho-sulforhodamine 101 or para-sulforhodamine 101; introducing a solution comprising the non-fluorescently labeled ligand to the substrate; and obtaining a second fluorescence measurement, wherein a change in fluorescence between the first and second measurements is indicative of binding. The method may further comprise covalently binding the receptor to the substrate. The method may be further defined as a high throughput method. The pH-sensitive fluorophore may be an ortho-sulforhodamine 101-conjugate. Some embodiments may further comprise employing para-sulforhodamine 101-conjugate as a reference. In some embodiments, ortho-sulforhodamine 101-conjugate comprises the receptor to form an ortho-sulforhodamine 101-labeled receptor.

Some embodiments contemplate a method of detecting binding between a non-fluorescently labeled ligand, or a ligand labeled only with ortho-sulforhodamine 101 or para-sulforhodamine 101, and a non-fluorescently labeled receptor, comprising: obtaining a first fluorescence measurement associated with a substrate comprising both a pH-sensitive fluorophore and the non-fluorescently labeled ligand, or a ligand labeled only with ortho-sulforhodamine 101 or para-sulforhodamine 101; introducing a solution comprising the non-fluorescently labeled receptor to the substrate; and obtaining a second fluorescence measurement, wherein a change in fluorescence between the first and second measurements is indicative of binding. The method may further comprise covalently binding the receptor to the substrate. The method may be further defined as a high throughput method. The pH-sensitive fluorophore may be an ortho-sulforhodamine 101-conjugate. Some embodiments may further comprise employing para-sulforhodamine 101-conjugate as a reference. In some embodiments, the ortho-sulforhodamine 101-conjugate comprises the ligand to form an ortho-sulforhodamine 101-labeled receptor.

Kinetic measurements of receptor-ligand binding may be performed using ortho-sulforhodamine 101-conjugates as described herein. Persons of skill in the art are familiar with kinetic experiments that may be performed using fluorophores, and such experiments may be performed using an ortho-sulforhodamine 101-conjugate. Exemplary kinetic measurements that may be determined include the $k_{on}$ for the binding event. Stopped-flow experiments or temperature jump experiments may be employed, for example. A kinetic experiment may be performed, for example, by labeling a receptor (e.g., a protein) with ortho-Texas Red®. In some embodiments, the labeled protein is initially free in solution and the ligand, such as a small organic molecule, is also free in solution. The ligand and receptor may be mixed from separate volumes into a third chamber or, alternatively, temperature jump experiments may be performed. The ligand may be negatively charged, positively charged, or contain no net charge. In the case of negatively charged ligands, the system will typically work as a "turn-on sensor". Signal would rise in this case of binding and drop upon unbinding. The opposite would typically occur for positively charged ligands. In some embodiments, an ortho-Texas Red® labeled protein is immobilized on a substrate. In this case, ligands can be followed over the surface to monitor binding kinetics.

The present invention also contemplates a composition for detecting protein-ligand binding comprising: at least one bead having a surface; at least one pH-sensitive dye-terminated PEGylated silane on the bead surface; at least one ligand-terminated PEGylated silane on the bead surface; and at least one PEGylated silane on the bead surface, wherein the at least one pH-sensitive dye-terminated PEGylated silane, the at least one ligand-terminated PEGylated silane, and the at least one PEGylated silane together substantially cover the bead surface. The pH-sensitive dye-terminated PEGylated silane may comprise ortho-Texas Red®-PEG-triethoxysilane. The present invention also contemplates a composition for detecting protein-ligand binding comprising: at least one bead having a surface; at least one pH-insensitive dye-terminated PEGylated silane on the bead surface; at least one ligand-terminated PEGylated silane on the bead surface; and at least one PEGylated silane on the bead surface, wherein the at least one pH-insensitive dye-terminated PEGylated silane, the at least one ligand-terminated PEGylated silane, and the at least one PEGylated silane together substantially cover the bead surface. The pH-insensitive dye-terminated PEGylated silane may comprise para-Texas Red®-PEG-triethoxysilane. A bead may be a glass bead, a polymer bead, an oxide substrate, a semiconductor substrate, a plastic substrate, or a supported bilayer. The diameter of the bead may be from about 0.1 µm to about 100 µm. In some embodiments, the pH sensitivity of the at least one pH-sensitive dye-terminated PEGylated silane on the bead surface is from about 2 to about 13. In some embodiments, the pH-sensitivity is of any value or range described herein.

Also contemplated is a system for detecting protein-ligand binding comprising a multi-well plate, wherein at least one well comprises (a) at least one bead having a surface; (b) at least one pH-sensitive dye-terminated PEGylated silane on the bead surface; (c) at least one ligand-terminated PEGylated silane on the bead surface; and (d) at least one PEGylated silane on the bead surface, wherein the at least one pH-sensitive dye-terminated PEGylated silane, the at least one ligand-terminated PEGylated silane, and the at least one PEGylated silane together substantially cover the bead surface. In some embodiments, a multi-well plate comprises at least well that comprises (a) at least one bead having a surface; (b) at least one pH-insensitive dye-terminated PEGylated silane on the bead surface; (c) at least one ligand-terminated PEGylated silane on the bead surface; and (d) at least one PEGylated silane on the bead surface, wherein the at least one pH-insensitive dye-terminated PEGylated silane, the at least one ligand-terminated PEGylated silane, and the at least one PEGylated silane together substantially cover the bead surface. The system may comprise both types of wells. The multi-well plate may be a 96-well plate or a 384-well plate.

The present invention further contemplates a method for detecting protein-ligand binding comprising: contacting a protein with a ligand in the presence of a composition comprising at least one bead having a surface; at least one pH-sensitive dye-terminated PEGylated silane on the bead surface; at least one ligand-terminated PEGylated silane on the bead surface; and at least one PEGylated silane on the bead surface, wherein the at least one pH-sensitive dye-terminated PEGylated silane, the at least one ligand-terminated PEGylated silane, and the at least one PEGylated silane together substantially cover the bead surface. In some embodiments, a method further comprises detecting binding of as little as about 250 molecules per pixel. In some embodiments, a method further comprises detecting binding of as little as about 1 part in 30,000 of the protein-ligand $K_D$.

It will be appreciated that the ability of a pH sensitive fluorophore to detect receptor-ligand binding depends on several factors, including the photobleaching resistance of the fluorophore, the salt concentration of the bulk solution (which affects the local electric field surrounding receptor, ligand, fluorophore, and optional substrate), the concentration of receptor or ligand present (such as the concentration of receptor bound to a surface (i.e., the receptor density at a surface)), and the concentration of the fluorophore (e.g., the fluorophore density at a surface). For example, higher concentrations of the pH-sensitive fluorophore result in improved detection limits, as described herein. The level of detection will also depend on whether a reference fluorophore is employed, where employment of such a reference is expected to yield improved detection limits. Examples of such improvement are described herein. Moreover, a pH-sensitive fluorophore will respond to changes in the local electric field out to about the Debye length, which is salt concentration dependent. Under physiological conditions, this is typically 0.5 or 2 nm. However, under low salt concentrations this distance can be tens or hundreds of nanometers. Indeed, in receptor-binding detection conditions where aggregation is problematic such that a salt concentration greater than zero is needed, the Debye length will decrease. If the analyte does not aggregate such that no salt is needed, the Debye length may increase to hundreds of nanometers such that the concentration of fluorophore may be decreased and sufficient levels of detection may be still be obtained.

While methods employing a substrate are described herein (that is, heterogeneous systems), a substrate need not always be employed to detect receptor-ligand binding using a pH sensitive fluorophore as described herein. For example, homogeneous solutions may be employed wherein a fluorophore is bound to a protein, and this entity is free in solution, and this solution comes into contact with a second solution that comprises a ligand or a putative ligand. The ligand may be a small organic molecule, for example. Detection of a change in fluorescence may indicate receptor-ligand binding in this situation as well. Accordingly, some embodiments of the present invention contemplate a method of detecting binding between a ligand and a receptor, comprising: obtaining a first fluorescence measurement of a first solution comprising a pH-sensitive fluorophore-labeled receptor; introducing a second solution comprising a ligand; and obtaining a second fluorescence measurement, wherein a change in fluorescence between the first and second measurements is indicative of binding.

It is noted that the technique described by U.S. Pat. No. 7,056,653 would not be expected to achieve the detection capabilities described herein. In particular, if the methods of the '653 were used to attempt to detect receptor-ligand binding as described herein, the signal-to-noise is expected to be significantly poorer (e.g., multiple orders of magnitude). This is due, in part, to the fact that the dyes described in the '653 patent do not possess high resistance to photobleaching. Further, detection limits would be poorer than methods described herein where a reference fluorophore is employed. In addition, Barenholz's methods always employ a substrate; use of a substrate is optional in methods described herein.

An "ortho-sulforhodamine 101-conjugate" refers to a compound comprising ortho-sulforhodamine 101 conjugated to a moiety:

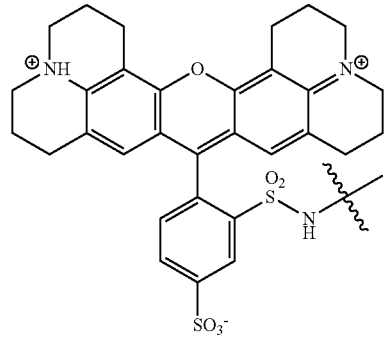

For example, an ortho-sulforhodamine 101-conjugate may be attached, directly or indirectly (through a linker, such as a polymer, such that the linker does not interfere with fluorescence measurement), to a ligand, receptor, polymer, lipid, or surface coating (e.g., metals such as Au via a thiol, or polymer bead via a linker). "ortho-Texas Red®-conjugate" and "ortho-sulforhodamine 101-conjugate" are used interchangeably herein.

A "para-sulforhodamine 101-conjugate" refers to a compound comprising para-sulforhodamine 101 conjugated to a moiety:

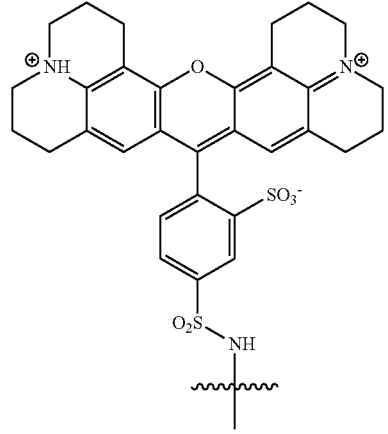

For example, a para-sulforhodamine 101-conjugate may be attached, directly or indirectly (through a linker, such as a polymer, such that the linker does not interfere with fluorescence measurement), to a ligand, receptor, polymer, lipid, or surface coating (e.g., metals such as Au via a thiol, or polymer bead via a linker). "para-Texas Red®-conjugate" and "para-sulforhodamine 101-conjugate" are used interchangeably herein.

In any embodiment that employs or refers to both an ortho-sulforhodamine 101-conjugate and a para-sulforhodamine 101-conjugate, the conjugate comprised in either may be the same or different.

As used herein, "ligand" refers to a moiety that is capable of binding to a receptor. A ligand and a receptor have a binding constant that is sufficiently strong to allow detection of binding by an assay method that is appropriate for detection of a ligand binding to a receptor (e.g., a second messenger assay to detect an increase or decrease in the production of a second messenger in response to ligand binding to the receptor; a binding assay to measure protein-ligand binding; an immunoassay to measure antibody-antigen interactions; a method as described herein; or other in vitro assays). A ligand and receptor specifically bind to each other (e.g., via covalent or hydrogen bonding). In certain embodiments, the $K_d$ of a receptor-ligand interaction is, at most 100 mM. In certain embodiments, the $K_d$ is at most about, at least about, or about 100 mM, 75 mM, 50 mM, 25 mM, 10 mM, 1 mM, 750 µM, 500 µM, 250 µM, 100 µM, 10 µM, 1 µM, 750 nM, 500 nM, 250 nM, 100 nM, 10 nM, 1 nM, 750 pM, 500 pM, 250 pM, 100 pM, 50 pM, 20 pM, 10 pM, 1 pM, 750 fM, 500 fM, 250 fM, 100 fM, 50 fM, 10 fM, 5 fM, 2 fM, 1 fM, or lower. Any ligand known in the art, including both naturally occurring and artificially prepared, is contemplated by the present invention. A ligand may be, for example, an ion, drug, antibiotic, nucleotide, antibody, antigen, hapten, hormone, steroid, enzyme, neurotransmitter, peptide, peptidomimetic, protein, nucleic acid, toxin, agonist, or antagonist, where these classes are not necessarily mutually exclusive. A ligand may have a net positive charge, a net negative charge, or may be neutral. A ligand may be a small organic molecule (e.g., having a molecular weight of less than 1,000 g/mol). A variety of ligands are described in, e.g., The Merck Index: An Encyclopedia of Chemicals, Drugs, and Biologicals, 2006. A ligand may be a putative ligand. In some embodiments, a ligand does not comprise a surface of a substrate. In some embodiments, the ligand is not a nucleic acid. In some embodiments, if a ligand is immobilized on a substrate, the ligand is presented on the surface of the substrate and not embedded within the substrate (i.e., the ligand is not shielded from the surface).

As used herein, a "receptor" is a molecule that binds a ligand. A receptor may be naturally occurring or artificially prepared. Such molecules include proteins, such as G-protein coupled receptors, enzymes, and antibodies. A receptor may be a cell-surface receptor. A receptor may be DNA, for example, as certain ligands bind to DNA (e.g., an intercalator). Vancomycin is another non-peptide receptor, where D-Ala-D-Ala is a ligand. A receptor may have a net positive charge, a net negative charge, or may be neutral. A receptor may be presented on the surface of an entity, such as a bacteria or a virus. A receptor may be a putative receptor. In some embodiments, a receptor does not comprise a surface of a substrate. In some embodiments, if a receptor is immobilized on a substrate, the receptor is presented on the surface of the substrate and not embedded within the substrate (i.e., the receptor is not shielded from the surface).

By "substantially free of para-sulforhodamine 101-conjugate," it is meant that a para-sulforhodamine 101-conjugate is present in an amount that is less than about 5% of that of an ortho-sulforhodamine 101-conjugate. In certain embodiments, it is present in an amount of at most or at least 5%, 4.5%, 4%, 3.5%, 3%, 2.5%, 2%, 1.5%, 1%, 0.5%, or less. Any embodiment herein may be substantially free of para-sulforhodamine 101-conjugate.

By "substantially free of ortho-sulforhodamine 101-conjugate," it is meant that a para-sulforhodamine 101-conjugate is present in an amount that is less than about 5% of that of a para-sulforhodamine 101-conjugate. In certain embodiments, it is present in an amount of at most or at least 5%, 4.5%, 4%, 3.5%, 3%, 2.5%, 2%, 1.5%, 1%, 0.5%, or less. Any embodiment herein may be substantially free of ortho-sulforhodamine 101-conjugate.

As used herein, "optically separated" refers to the fact that to detect the ortho and para isomers of sulforhodamine 101 optically, they have to be spatially separated. This means that they are bound to a substrate in two separate spots. Those spots should be separated beyond the diffraction limit (~500 nm) so that they can be easily discerned. In practice, for example, if the spot size is 5 µm×5 µm, it would make sense to separate the spots by a 5 µm spacer. These distances can be judged by optical microscopy using a standard CCD camera for detection, as is known in the art. Thus, optically separated fluorophores are physically separated to a distance where they can be measured separately by microscopy and separated to a physical distance beyond the diffraction limit.

A substrate, such as a bead, that comprises a receptor, ligand, fluorophore, or any other agent described herein may refer to such an agent that is immobilized onto or into, covalently bound to, or non-covalently bound to the surface of the substrate. When an agent is immobilized, it is typically immobilized in a way that presents the agent on the surface of the substrate (that is, the external surface of the substrate). A linker may join the agent to the substrate, wherein the linker is covalently bound to the agent and to the substrate. Any linker known in the art may be employed provided it does not prevent the receptor from binding to the ligand and does not prevent fluorescence measurement. A pH-sensitive fluorophore may be immobilized to the same surface of a substrate as either a ligand or a receptor.

pH-Sensitive fluorophores, as described herein, typically exhibit a high resistance to photobleaching. Thus, a pH-sensitive fluorophore may be further defined as a photobleaching-resistant pH-sensitive fluorophore. In some embodiments, a photobleaching-resistant pH-sensitive fluorophore corresponds to a resistance that is at least two orders of magnitude more difficult to photobleach than coumarin 102 (see Table 1 below).

TABLE 1

Photostability Properties of Coumarin and Rhodamine Dyes in Water at Low Irradiances Obtained from the Cell-Bleaching Experiments

| dye | $\phi_b{}^{a,b}$ | $\mu^{a,c}$ | $\tau_0$ (ns)$^d$ | $k_b$ (s$^{-1}$)$^{a,e}$ | $\sigma_{01}(\lambda)$ (10$^{-17}$ cm$^2$) |
|---|---|---|---|---|---|
| Coumarin 120 | $3.4 \times 10^{-4}$ | 3 000 | 5.0 | 6 700 | 3.9 (365 nm) |
| Coumarin 307 | $1.5 \times 10^{-4}$ | 6 500 | 4.5 | 3 400 | 5.4 (397 nm) |
| Coumarin 102 | $4.3 \times 10^{-4}$ | 2 300 | 5.5 | 7 800 | 7.0 (397 nm) |
| Coumarin 39 | $1.2 \times 10^{-3}$ | 800 | 5.6 | 21 000 | 4.7 (397 nm) |
| Carbostyril 124 | $1.4 \times 10^{-3}$ | 700 | 5.0 | 27 000 | 6.3 (335 nm) |
| Rhodamine 6G | $1.2 \times 10^{-6}$ | 833 000 | 3.9 | 310 | 22.2 (515 nm) |

TABLE 1-continued

Photostability Properties of Coumarin and
Rhodamine Dyes in Water at Low Irradiances Obtained
from the Cell-Bleaching Experiments

| dye | $\phi_b^{a,b}$ | $\mu^{a,c}$ | $\tau_0$ (ns)$^d$ | $k_b$ (s$^{-1}$)$^{a,e}$ | $\sigma_{01}(\lambda)$ (10$^{-17}$ cm$^2$) |
|---|---|---|---|---|---|
| TMR | $3.3 \times 10^{-7}$ | 3 070 000 | 2.3 | 140 | 13.3 (515 nm) |
| Rhodamine 123 | $6.4 \times 10^{-7}$ | 1 570 000 | 4.0 | 160 | 12.3 (515 nm) |

$^a$The standard deviation of all values is in the order of 20%, obtained by repeated measurements.
$^b$The quantum yield of photobleaching. $\phi_b = \phi_b^3$. was calculated from the measured fluorescence decreases using eq 15.
$^c$The mean number of survived excitation cycles. $\mu$. was calculated from $\phi_b$: $\mu = 1/\phi_b$.
$^d$The fluorescence lifetimes. $\tau_0$. of the dyes were determined from precision measurements at dye concentrations of about 10$^{-7}$ M.
$^e$The composite microscopic rate constant, $k_b$, of photobleaching from $S_1$ and $T_1$ was calculated using eq 9.

Eggeling, C., et al., Anal. Chem., 70:2651-2659, 1988. In addition to rhodamine 6G, TMR, and rhodamine 123, ortho-sulforhodamine 101 is another example of a pH-sensitive fluorophore that exhibits a high resistance to photobleaching. In some embodiments, the pH-sensitive fluorophore comprises a rhodamine moiety. In any embodiment herein that employs ortho-sulforhodamine 101 or a conjugate thereof, any pH-sensitive fluorophore with a high resistance to photobleaching may be employed alone or as a conjugate, and vice versa. In some embodiments, the pH sensitivity of a pH-sensitive fluorophore may range from about, at most about, or at least about 2, 2.5, 3, 3.5, 4, 4.5, 5, 5.5, 6, 6.5, 7, 7.5, 8, 8.5, 9, 9.5, 10, 10.5, 11, 11.5, 12, 12.5, or 13, or any range derivable therein. pH-Sensitivity of a given fluorophore may be altered by, for example, adding negative or positive charge to the surface (e.g., adding negatively or positively charged lipids to a lipid surface).

A change in the fluorescence of a pH-sensitive fluorophore is observed upon receptor-ligand binding in embodiments described herein. The change may be as less than 3 parts in 1,000 at the 99% confidence level, for example. The change may be expressed in terms of percentage, such as a change of about, at least about, or at most about 0.5, 1, 1.5, 2, 2.5, 3, 3.5, 4, 4.5, 5, 5.5, 6, 6.5, 7, 7.5, 8, 8.5, 9, 9.5, or 10% or more.

A pH-insensitive fluorophore is a fluorophore that does not exhibit a change in fluorescence over the pH range of the experimental conditions employed, or exhibits a maximum change of less than 5%. pH-Insensitive fluorophores are well-known in the art, such as those sold by Invitrogen, Inc. An example of a pH-insensitive fluorophore is para-sulforhodamine 101.

In some embodiments, if a fluorophore is immobilized on a substrate, the fluorophore is presented on the surface of the substrate and not embedded within the substrate (i.e., the fluorophore is not shielded from the surface).

As used herein, "lipid" refers to a straight-chain hydrocarbon radical having 5 carbons or higher, wherein the radical may comprise single, double, and/or triple bonds. In certain embodiments, the straight-chain hydrocarbon radical has between 5 and 45 carbon atoms. Non-limiting examples of lipids include —$C_5H_{11}$, —$C_{11}H_{23}$, —$C_{15}H_{31}$, —$C_{19}H_{39}$ and —$C_{17}H_{31}$.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value.

As used herein the specification, "a" or "an" may mean one or more, unless clearly indicated otherwise. As used herein in the claims, when used in conjunction with the word "comprising," the words "a" or "an" may mean one or more than one.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

As an alternative to or in addition to "comprising," any embodiment herein may recite "consisting of." For example, the invention contemplates a substrate consisting of an ortho-sulforhodamine 101-conjugate and a ligand or a receptor, wherein the substrate is substantially free of para-sulforhodamine 101-conjugate. As another example, also contemplated is a method of detecting binding between a non-fluorescently labeled ligand and a non-fluorescently labeled receptor, the method consisting of: obtaining a first fluorescence measurement associated with a substrate comprising both a pH-sensitive fluorophore and the non-fluorescently labeled ligand; introducing a solution comprising the non-fluorescently labeled receptor to the substrate; and obtaining a second fluorescence measurement, wherein a change in fluorescence between the first and second measurements is indicative of binding. The transitional phrase "consisting of" excludes any element, step, or ingredient not specified in the claim.

It is specifically contemplated that any limitation discussed with respect to one embodiment of the invention may apply to any other embodiment of the invention. Furthermore, any composition of the invention may be used in any method or system of the invention, and any method of the invention may be used to produce or to utilize any composition of the invention.

In some embodiments, generations of label free biosensors as described herein may be practiced by employing pH sensitive fluorescent substrates that turn on when analyte molecules bind to the surface. For example, a support surface may be coated with a two-dimensionally fluid phospholipid membrane containing ligands for specific protein binding. The membranes may also be doped with a small concentration of a pH sensitive lipid-conjugated fluorophore, such as ortho-Texas Red® DHPE. This dye molecule fluoresces strongly when it is protonated, but not when it is deprotonated. The binding of analyte molecules to the substrate surface will shift the local pH relative to the bulk solution value and, hence, modulate the fluorescence of the underlying substrate. Because supported bilayers are used in some assay embodiments, substrates may be resistant to non-specific protein adsorption and may provide the same type of two-dimensional ligand rearrangements that take place on the surface of the plasma membrane in whole cells. Supported lipid bilayers to be employed in some assay embodiments may be compatible with microfluidic and array-based technologies. Therefore, many sensor elements may be read out simultaneously under a standard fluorescence microscope or even under a fluorescence plate reader.

In some embodiments, an assay may be optimized to achieve the lowest possible limit of detection. Both the ligand density and the concentration of pH sensitive fluorophore molecules may be modulated for this purpose. Additionally, supported bilayers containing a pH insensitive fluorophore, para-Texas Red® DHPE, may be use as a reference standard for monitoring changes in fluorescence intensity. This molecule has almost the identical physical properties as ortho-Texas Red® DHPE and may permit reliable detection of very small changes in fluorescence intensity (e.g., less than 3 parts in 1000) at the 99% confidence level. The limit of detection for some assay embodiments may be established in terms of the lowest concentration of analyte protein which may be detected and/or the lowest number density of proteins which can be reliably detected on the substrate surface. In some embodiments, a detection limit of 10 proteins/$\mu m^2$ at the surface or less may be achieved. LOD values may be tested with a variety of binding systems including antibody/antigen, concanavalin A/mannose, and $GM_1$/cholera toxin.

In some embodiments, a sensor may be generalized for operation under a variety of conditions. A sensor may be configured to "turn on" when negatively charged proteins adsorb at the membrane interface near, e.g., pH 7.8. The bilayer chemistry may be tuned, according to some embodiments, to optimize the platform for a range extending from pH 4.3 to 11.3, or any other pH range described herein. Positively and negatively charged lipids, for example, may be used for this purpose. A fluorophore may turn on as the pH is increased and may be tested for use with positively charged protein analytes. It may be desirable to assess the range over which a sensor provides a linear fluorescence intensity change with changing local pH values.

In some embodiments, a pH sensitive assay may be configured for use with one or more fluorescent bead platforms. Micron scale beads, which are typically sensitive to specific protein binding, may be made by employing silane chemistry to attach pH sensitive dye molecules and ligands. Beads may be used in a standard 96 well assay and read out with a standard fluorescence plate reader. Embodiments of this assay may be optimized for the lowest possible limits of detection and maximum resistance to non-specific protein adsorption.

Label-free biosensors may be made using supported lipid bilayer and bead-based platforms. These platforms may be fabricated using high throughput/low sample volume microfluidic techniques. Such on-chip technologies may permit the limits of detection of the pH sensor assay under a particular set of conditions to be tested (e.g., rapidly tested). New assay platforms may be fabricated within 24 hours. For example, the performance conditions may be assessed (e.g., rapidly assessed) for the optimum conditions for the best limits of detection, minimum non-specific adsorption, as well as flexibility of pH range, dye chemistry, and lipid content.

According to some embodiments of the disclosure, a simple label-free assay may be run in imaging mode for multiplexed data collection while still retaining very high sensitivity. A method may be simple to use and compatible with standard laboratory equipment such as a fluorescence microscope or plate reader. Thus, practitioners may not need to purchase a dedicated instrument or specialized assay platforms (e.g., metal coated chips). In some embodiments, an assay may be as highly sensitive as known fluorescence techniques, but without labeling the target analyte (i.e., receptor or ligand) with a fluorophore. Instead, fluorescent dyes may be directly immobilized onto the substrate surface. In some embodiments, these dyes may function as sensor elements upon specific protein binding. This may be achieved if the substrate-bound dye's fluorescence is altered (e.g., strongly enhanced) by a specific binding event.

Without limiting any particular embodiment to any specific mechanism of action, the underlying physical principle for a detection method may be based upon the idea that the binding of proteins at lipid membrane surfaces will locally perturb the pH. Most proteins in solution are negatively charged at physiological pH. Therefore, when these biomacromolecules adsorb on a surface, they recruit hydronium ions with them. This lowers the surface pH relative to the bulk value. This local acidification can be exploited to protonate a fluorophore that will "turn-on" in the protonated state, but be inactive in the deprotonated state. A schematic image of this idea is shown in FIG. 1. As can be seen, ligands (gray triangles) are incorporated into a supported phospholipid bilayer along with a pH sensitive fluorophore (shown in pink). The fluorophores are initially inactive. They may be activated (shown in red), however, by the binding of a negatively charged protein. This process may be highly sensitive because fluorescence microscopy may be useful down to the single molecule level (Pappas, D., et al., *Trends Anal. Chem.* 26:884-894, 2007). Moreover, the process may be amplified because the binding of one protein can turn on multiple fluorophores.

Figure 2:
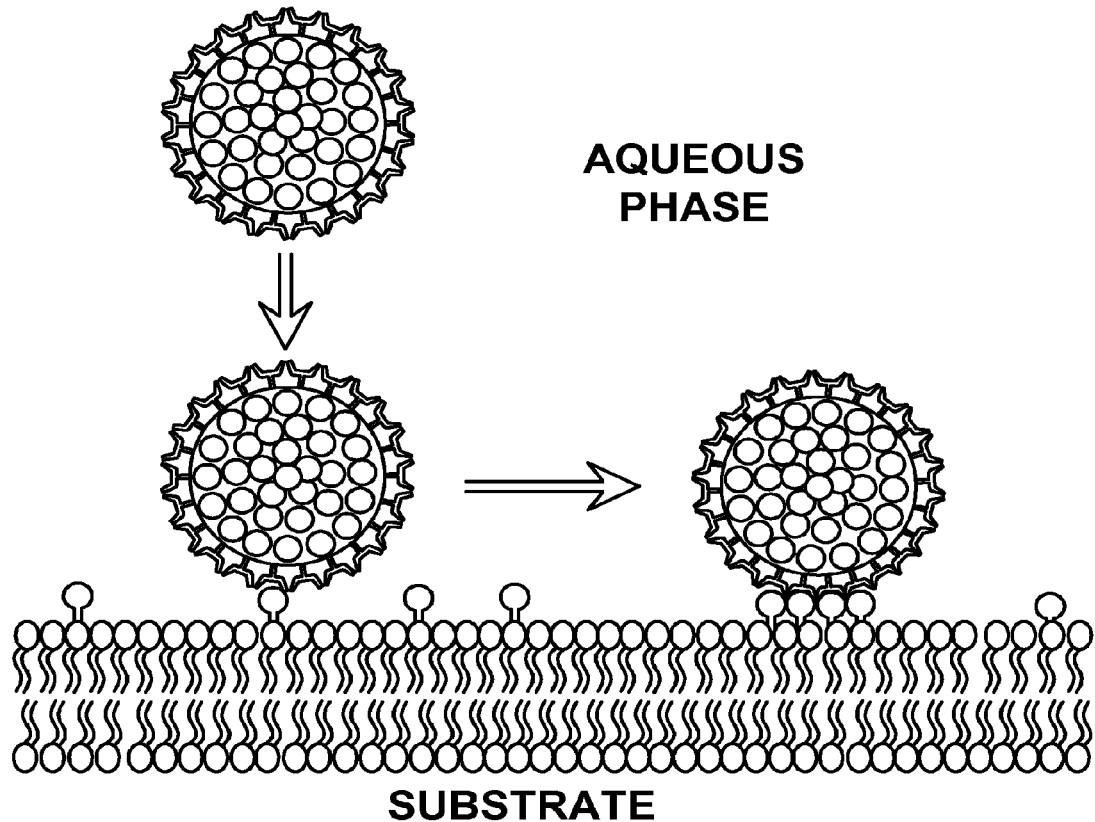
FIG. 2. Multivalent binding of a virus particle onto a supported lipid bilayer via the lateral rearrangement of membrane-conjugated ligands. The height of the system from the glass support to the top of the membrane is roughly 5 nm (Cremer, P. S. and Boxer, S. C. *J. Phys. Chem. B* 103:2554-2559, 1999) and the virus particles are not drawn to scale.

A biosensor, according to some embodiments, may be made by exploiting supported phospholipid bilayer platforms. Supported bilayers may be formed by coating a planar hydrophilic substrate with a phospholipid membrane. A thin water layer resides between the lower leaflet of the bilayer and the underlying substrate (Kim, J., et al., *Langmuir* 17:7255-7260, 2001). Hence, the bilayer remains two-dimensionally fluid at the interface. Ligands may be directly incorporated into the membrane and may be free to move around in two dimensions. This allows them to rearrange to accommodate binding with proteins, viruses, and bacteria with multiple binding sites in much the same manner as occurs in vivo at cell surfaces (Daniel, S., et al., *MRS Bull.* 31:536-540, 2006). An example of this concept is shown in FIG. 2. In this case, an incoming virus particle (green) contains many receptor sites that can interact with the ligands (yellow), which are presented on the surface of the supported bilayer. The lateral rearrangement of the ligands allows for highly selective binding to occur.

A supported phospholipid bilayer sensor platform having zwitterionic lipids (net charge of zero), in some embodiments, may be resistant to non-specific binding of proteins from solution in much the same manner that a cell membrane can resist the nonspecific binding of protein molecules (Castellana, E. T. and P. S. Cremer, *Surf. Sci. Rep.* 61:429-444, 2006). Such platforms may have a high degree of specificity and/or resistance to non-specific adsorption (Yang, T., et al., *J. Am. Chem. Soc.* 125:4779-4784, 2003; Shi, J., et al., *J. Am. Chem. Soc.* 129:5954-5961, 2007; Yang, T. L., et al., *Anal. Chem.* 73:165-169, 2001). A platform may be stabilized against exposure to air and/or may be compatible with microfluidic technologies (Holden, M. A., et al., *J. Am. Chem. Soc.* 126:6512-6513, 2004; Albertorio, F., et al., *Langmuir* 21:7476-7482, 2005). An example of an on-chip microfluidic bilayer assay is shown in FIG. 3. The schematic diagram on the left depicts an example standard design. In this case, a polydimethylsiloxane (PDMS) mold is bonded to a planar glass support. Phospholipid membranes (shown in green) are coated on the walls and floors of the device via the vesicle fusion method (Yang, T. L., et al., *Anal. Chem.* 73:165-169, 2001). An epifluorescence image of a working device is shown on the right. The alternating red and green fluorescence within the channels emanates from doping the bilayers with red (Texas Red®) or green (NBD) fluorophore-conjugated lipids. Each channel represents a separate sensing element in the multiplexed assay. Two-dimensional arrays may also be made in addition to the one-dimensional array shown here. The dye molecules are present at a concentration of 0.1 mol % and the specific dye chemistry of Texas Red® will be discussed in the next section.

Figure 4:
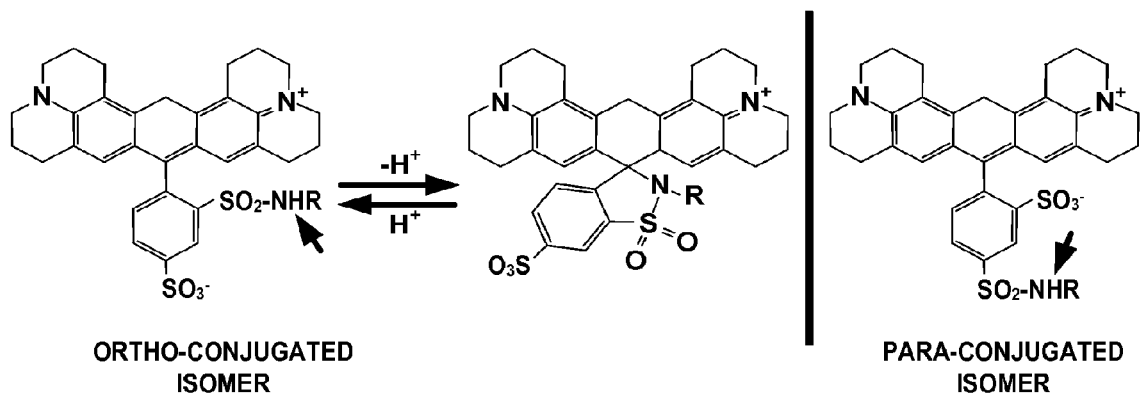
FIG. 4. Isomers of Texas Red® DHPE. The sulfonamide moiety (—SO$_2$—NHR) may be conjugated to the lower ring at either the ortho or para positions. It contains a titratable proton (shown with arrows). In the case of ortho conjugation, removal of the proton leads to the formation of a ring structure which makes the molecule non-fluorescent. The same intramolecular reaction is not possible with the para isomer. The R group represents the lipid, dihexadecylphosphatidylethanolamine (DHPE).

Measurements using the ortho isomer of Texas Red®-DHPE as a pH sensitive dye (FIG. 4) have been made. This molecule fluoresces in the protonated state, but not when it is deprotonated (Marchesini, S., et al., *Biochem. Int.* 27:545-550, 1992). The process is perfectly reversible and it is possible to toggle between these two states by raising and lowering the pH (Corrie, J. E. T., et al., *Bioconjugate Chem.* 12:186-194, 2001). By contrast, the para isomer of Texas Red®-DHPE is a pH insensitive dye and may be employed in control experiments.

Figure 5:
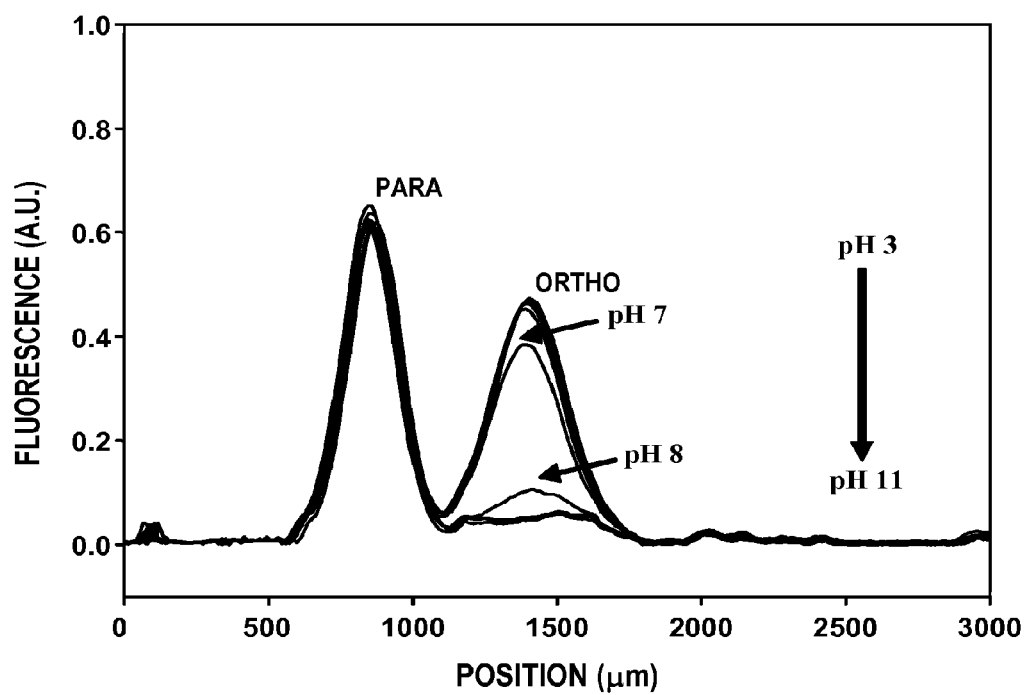
FIG. 5. Fluorescence line scans across a supported bilayer containing para- and ortho-conjugated Texas Red® DHPE.

The ortho and para isomers may be readily separated from each other by thin film chromatography (Daniel, S., et al., *J. Am. Chem. Soc.* 129:8072-8073, 2007). These lipid-conjugated dyes may also be directly placed within a supported lipid bilayer and separated from each other by electrophoresis (Daniel, S., et al., *J. Am. Chem. Soc.* 129:8072-8073, 2007). FIG. 5 shows a series of fluorescence line scans of para and ortho Texas Red®-DHPE bands in a supported bilayer as the pH is raised from 3 to 11 in single pH unit steps. As FIG. 5 illustrates, the intensity of the para band remains unchanged, while the ortho band drops dramatically in intensity between pH 7 and 8.

The peak heights from the ortho-conjugated Texas Red® data in FIG. 5 may be used to obtain a titration curve for this isomer. These data, which are plotted in FIG. 6, clearly show that the $pK_A$ of the dye is 7.8. (±0.2). To obtain the y-axis, the peak height at pH 3 was set to 1.0, and all other peak heights are relative to this value.

As with any acid, the measured value of the $pK_A$ for ortho-Texas Red®-DHPE is highly sensitive to its surrounding environment. Therefore, adsorption of negatively charged proteins to the interface lowers its pH value relative to the bulk. This effect may be exploited in a sensing application where the bulk pH value is near the $pK_A$ of the dye. The biotin/anti-biotin binding pair was monitored as a demonstration of this concept. Supported phospholipid bilayers were made with 99.4 mol % 1-palmitoyl-2-oleoyl-sn-glycero-3-phosphocholine (POPC), 0.5 mol % biotin-cap-DPPE (biotin-PE), and 0.1 mol % ortho-Texas Red®-DHPE. The bilayers were coated on the inside walls and floors of PDMS/glass microfluidic channels as described in FIG. 3. The solution contained 10 mM phosphate buffered saline (PBS, pH 7.8) with 150 mM NaCl.

Figure 7A:
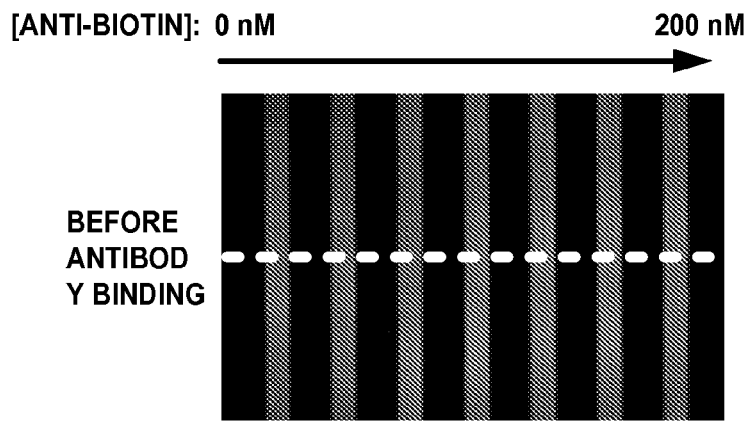
FIG. 7. (a) Epifluorescence image of a seven channel microfluidic device coated with supported POPC bilayers containing 0.5 mol % biotin-PE. (b) Image of the same device after the introduction of unlabeled anti-biotin. The blue and red dotted lines are used to obtain the line profiles shown in FIG. 8.
Figure 7B:
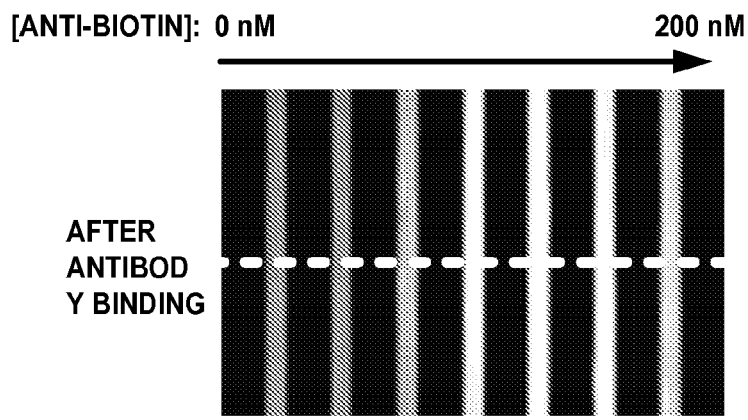

An epifluorescence image from the seven channel device used in these experiments is shown in FIG. 7A. As expected, the fluorescence intensity was essentially identical in each channel. Next, anti-biotin was introduced into the system at increasing concentration from left to right (0 to 200 nM). This led to an increase in fluorescence as shown in FIG. 7B. Fluorescence line profiles taken from FIG. 7 are plotted in FIG. 8.

Figure 9A:
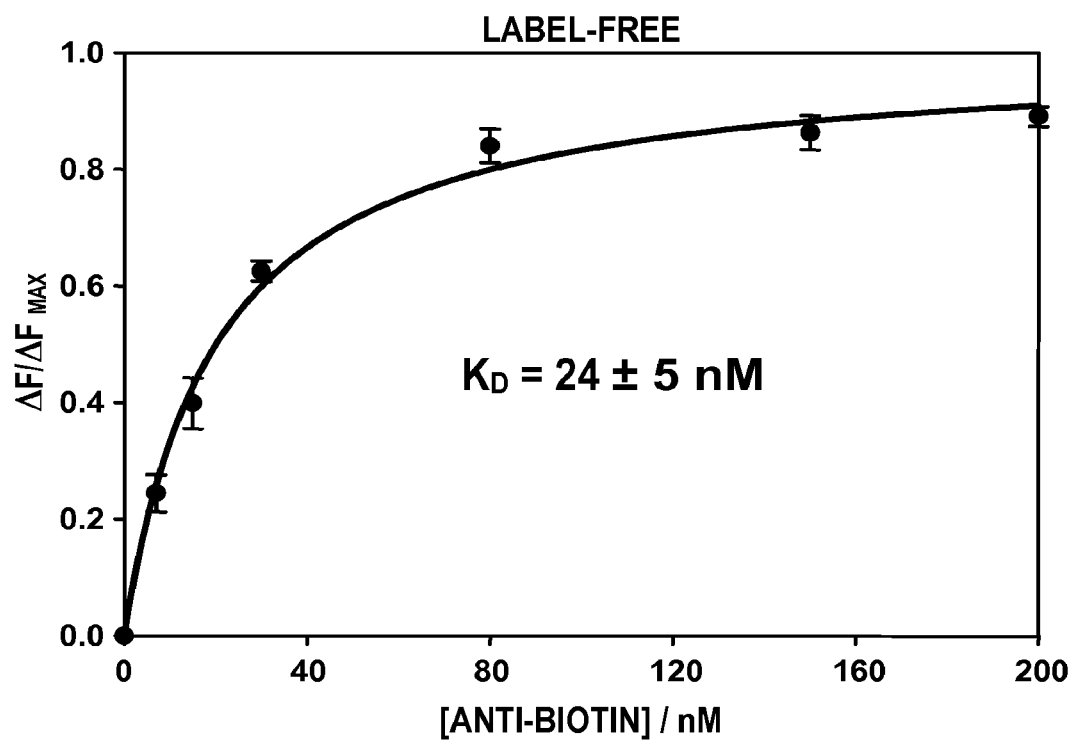
FIG. 9. Binding curves for the (a) label-free and (b) labeled antibody binding systems. The solid lines are Langmuir isotherm fits to the data points. The error bars represent the average of three measurements.
Figure 9B:
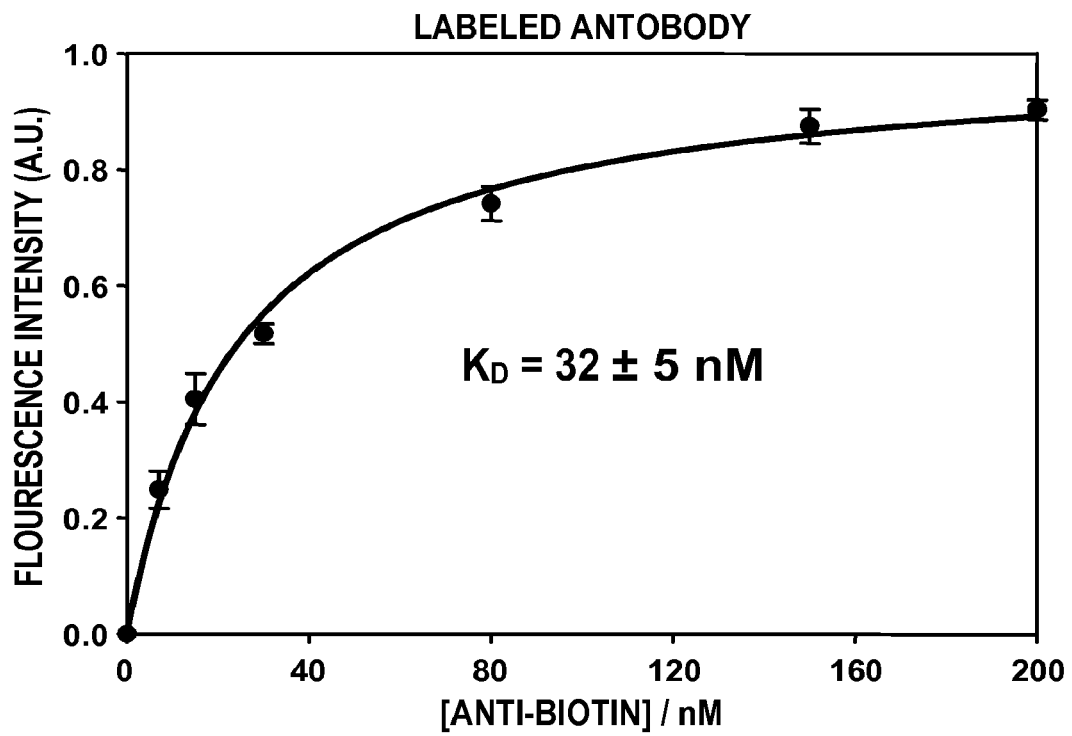
Figure 10A:
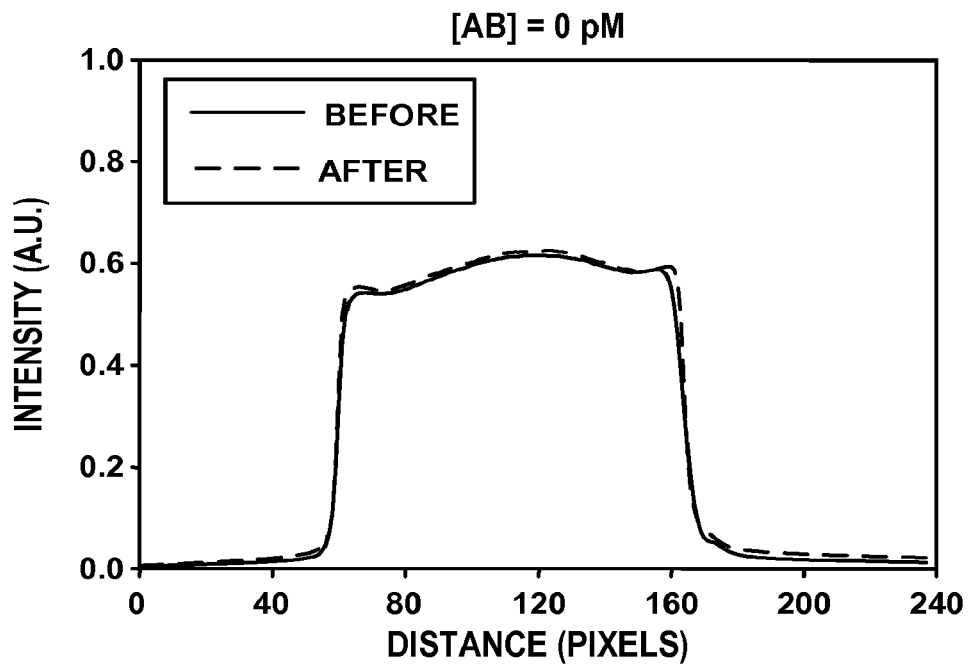
FIG. 10. Intensity line profiles across single microfluidic channels as various concentrations of anti-biotin antibodies are introduced to the bulk solution. The bilayers in these studies contained 0.5 mol % biotin-PE and 0.03 mol % ortho-Texas Red® DHPE in POPC. The experiments were conducted at pH 7.8 in 10 mM PBS with 150 mM NaCl.
Figure 10B:
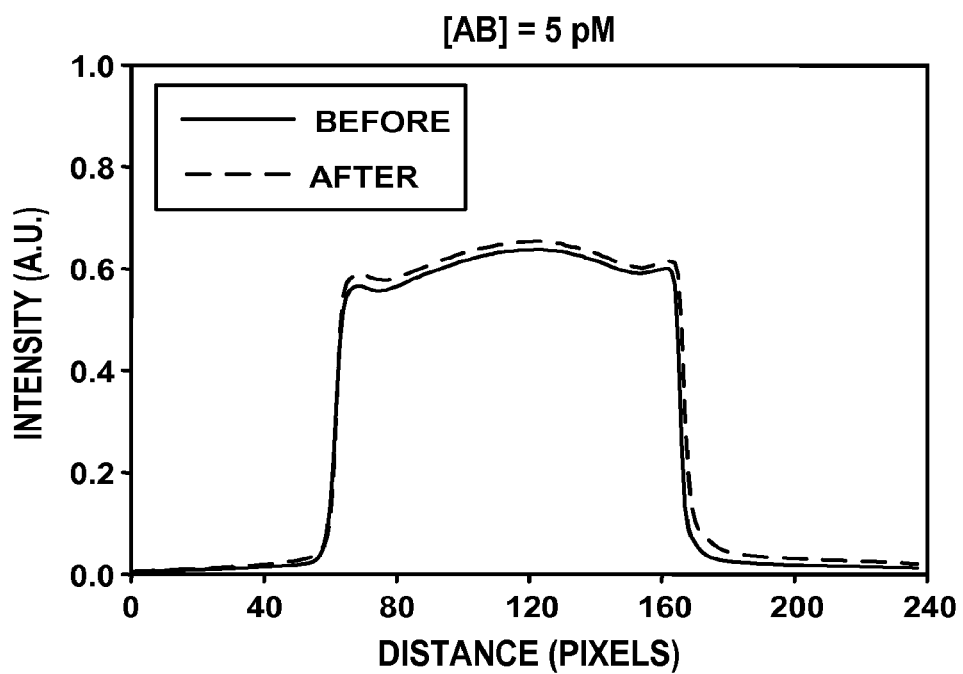
Figure 10C:
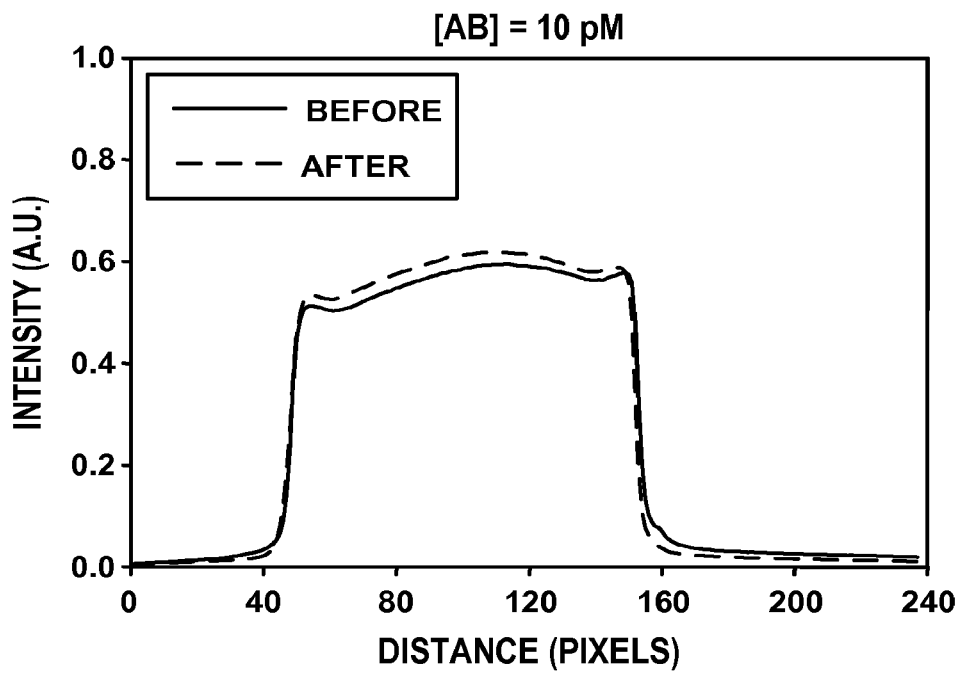
Figure 10D:
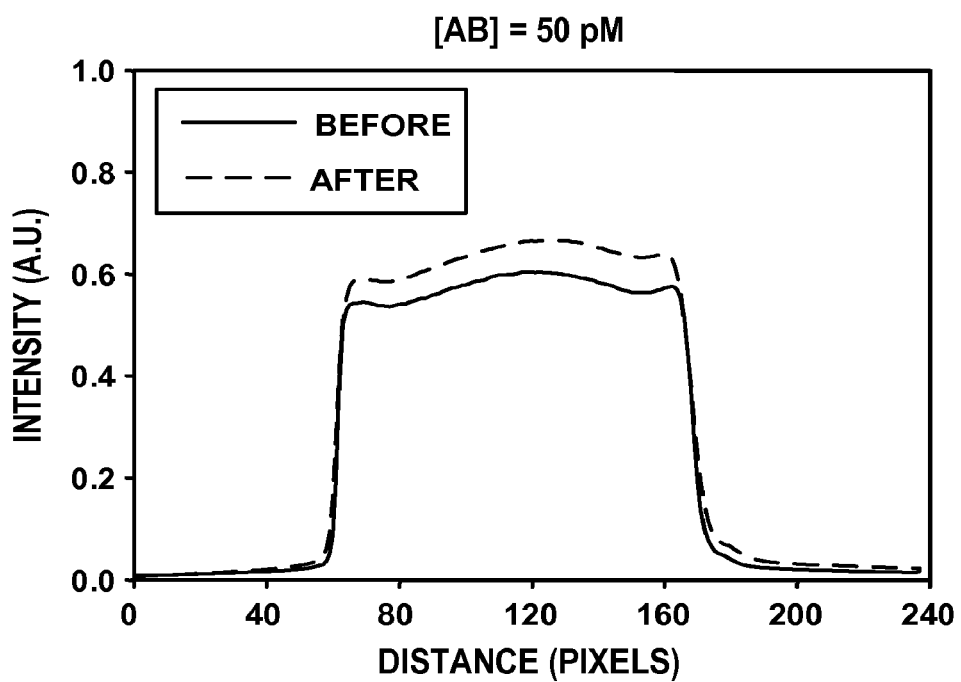
Figure 10E:
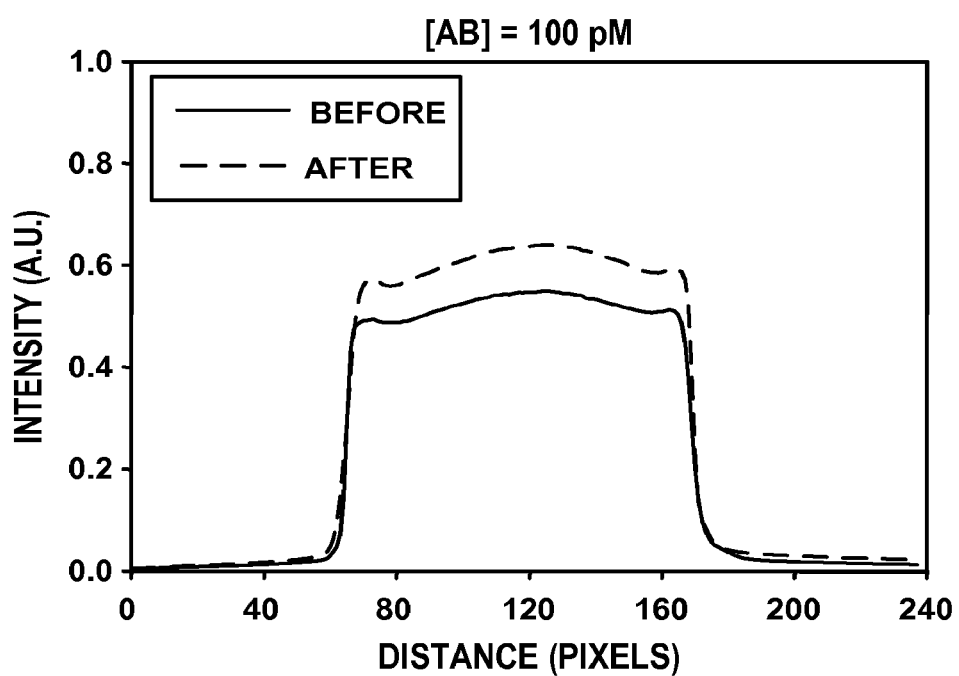

As illustrated, the fluorescence intensity after the introduction of the antibody increased and then leveled-off. The background data (blue) for each channel were then subtracted from the signal data (red) and plotted as a function of bulk protein concentration (FIG. 9A). The data points were fitted by a Langmuir isotherm, which yielded a $K_D$ value of 24 (±5) nM. Classical antibody binding experiments (Yang, T., et al., *J. Am. Chem. Soc.* 125:4779-4784, 2003) were also performed using fluorescently tagged antibodies (FIG. 9B). In this case the membranes contained 99.5 mol % POPC and 0.5 mol % biotin-PE. These experiments yielded a $K_D$ value of 32 (±5) nM. Therefore, the labeled and label-free assays give identical results within experimental error.

The y-axis in FIG. 9A is based upon the change in fluorescence, $\Delta F$, relative to the maximum fluorescence, $\Delta F_{max}$, when a saturation concentration of anti-biotin is present. Several sets of control experiments were performed. For example, anti-dinitrophenyl (anti-DNP) antibodies were used instead of anti-biotin antibodies. Also, experiments were performed without any biotin-PE in the membrane. In both of these cases, the fluorescence intensities from the microchannels remained unchanged within experimental error upon introduction of protein. Such results are consistent with both high ligand-receptor specificity as well as relatively low levels of non-specific protein adsorption.

The similarities in the results for the labeled antibody measurements and label-free measurements are remarkable (FIG. 9). Moreover, they have essentially identical error bars associated with them. This is strong evidence for the reliability of the label-free assay. Significantly, it should be noted that the label-free assay is far easier to perform. The classical assay shown in FIG. 9B requires that the antibodies be conjugated with fluorescence dye molecules and that free dye be subsequently separated from the labeled antibodies by running the mixture down a size exclusion column. Once the labeled antibodies are introduced into the microchannels, the fluorescence assay must discriminate between antibodies bound to the surface and those in the bulk solution above it. This is typically done by total internal reflection fluorescence microscopy (TIRFM) (Axelrod, D., et al., *Annu. Rev. Biophys. Bio.* 13:247-268, 1984), a surface specific technique which requires a laser beam to be introduced into the sample through a dove prism geometry (Yang, T., et al., *J. Am. Chem. Soc.* 125:4779-4784, 2003). By contrast, the label free assay may be run in standard epifluorescence mode because the pH sensitive dye molecules are already located at the surface by incorporation into the supported bilayer.

The lower limit of detection (LOD) of a pH sensing technique may be characterized by abstracting both bulk and surface values. The benchmark for comparison to be used in this example is data from surface plasmon resonance (SPR) measurements. Sensitivity limits are often reported in the literature in terms of the minimum bulk analyte concentration which can be detected (Liang, M., et al., *Assay Drug Dev. Techn.* 5:655-662, 2007). For example, in an SPR assay, one may wish to monitor an antibody/antigen interaction with a $K_D$ value of 30 nM. In this case, the hapten might be attached to the substrate and the antibody introduced over the surface at varying concentrations. The LOD is normally given in such cases as the minimum bulk protein concentration that can be detected. A typical value might be ~60 pM as this concentration represents 2% of the concentration corresponding to the $K_D$ value. However, one might also wish to find the LOD for biotin/streptavidin binding. Since this latter system has a tighter equilibrium dissociation constant ($K_D \approx 1$ pM) (Haes, A. J. and R. P. Van Duyne, *J. Am. Chem. Soc.* 124:10596-10604, 2002), the LOD may be 20 fM. Again, this would represent 2% of the $K_D$ value. In both cases, one is detecting nearly the identical number density of proteins on the surface. Therefore, the total number of proteins that can be detected at the surface per unit area would represent a more intrinsic reflection of the sensitivity. However, since bulk values are so widely reported, both sets of data for pH sensing studies may be collected and reported.

Figure 8:
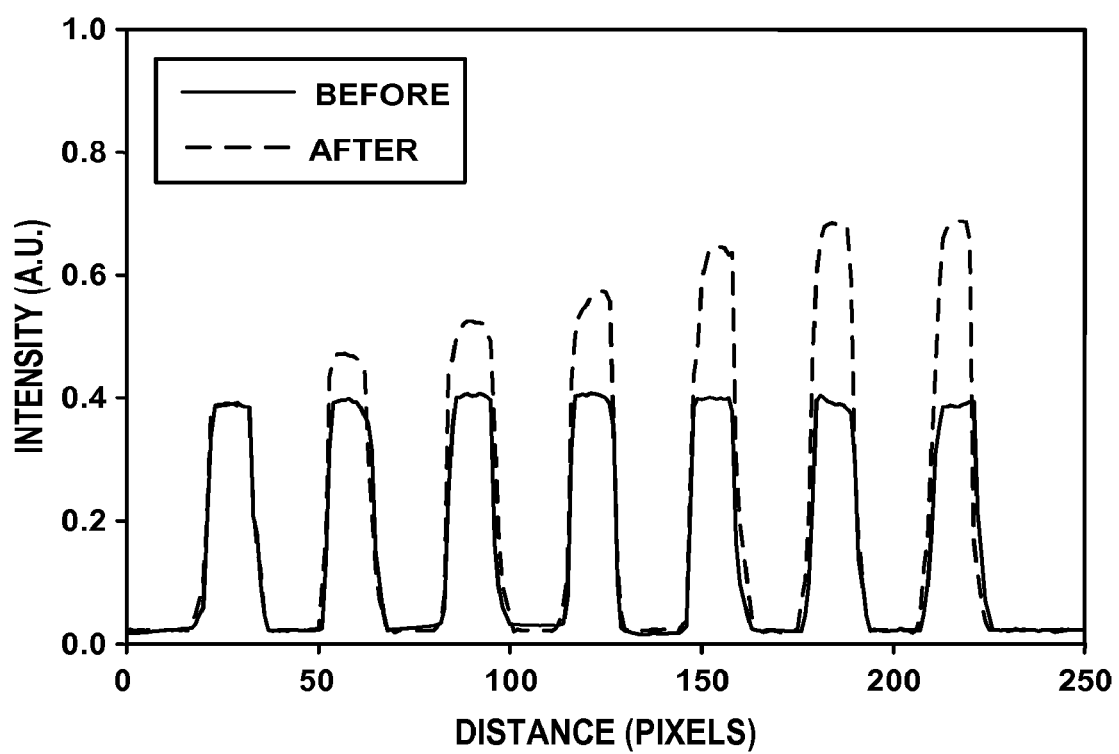
FIG. 8. Fluorescence line profiles from FIG. 7.

A first set of LOD measurements made for biotin/anti-biotin under the same conditions as those described in FIGS. 7-9 are shown in FIG. 10. These data are for fluorescence line profiles cross single channels both before (blue) and after (red) the introduction of anti-biotin antibodies. Since the experiments were conducted at pH 7.8, there is already a significant amount of intensity from the ortho-Texas Red® DHPE molecules before the antibody is introduced. As can be seen, the line profile remains essentially unchanged when 0 pM antibody was added, but changes by ~10% when 100 pM anti-biotin was added. The intensity changes are linear with concentration between 0 and 100 pM. Error analysis on the intensity profiles revealed that they are stable to within ±0.3% over a 1 hour time period. This gives an LOD value of ~8 pM if LOD is defined as 2.58 times the experimental error. This definition of LOD was chosen because it represents the 99% confidence limit for the measurements.

Figure 30:
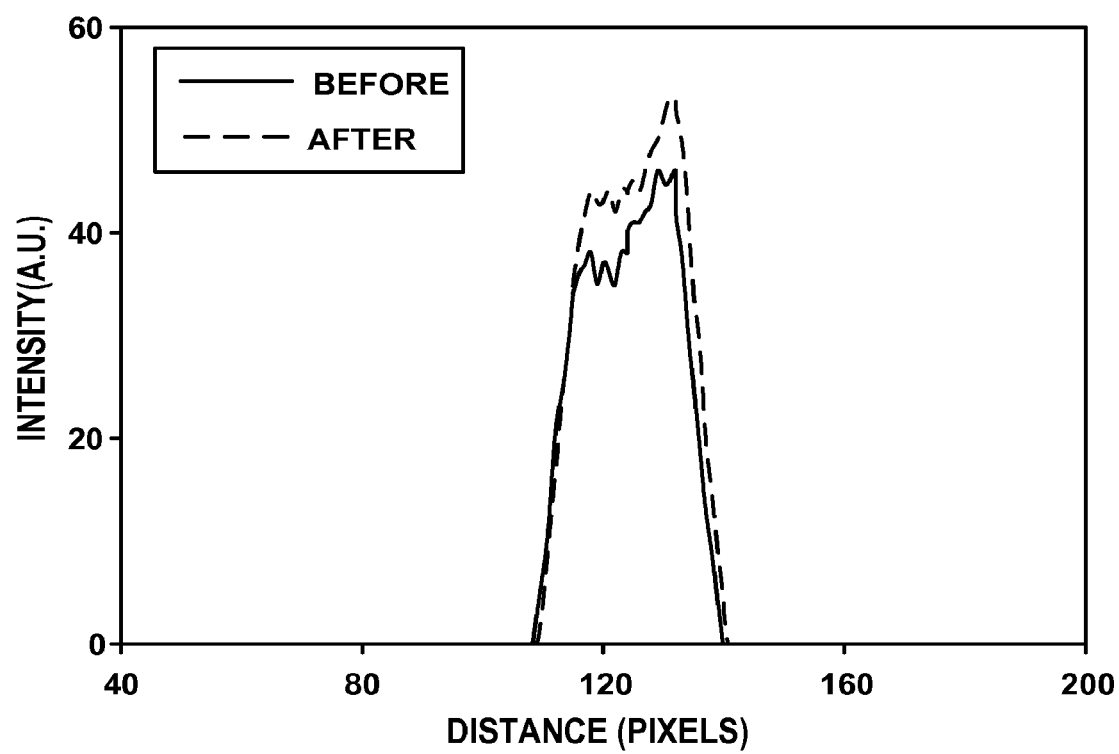
FIG. 30. A line profile from a micrograph under conditions described in FIG. 29 with 10 fM anti-biotin antibody in the bulk solution.
Figure 31:
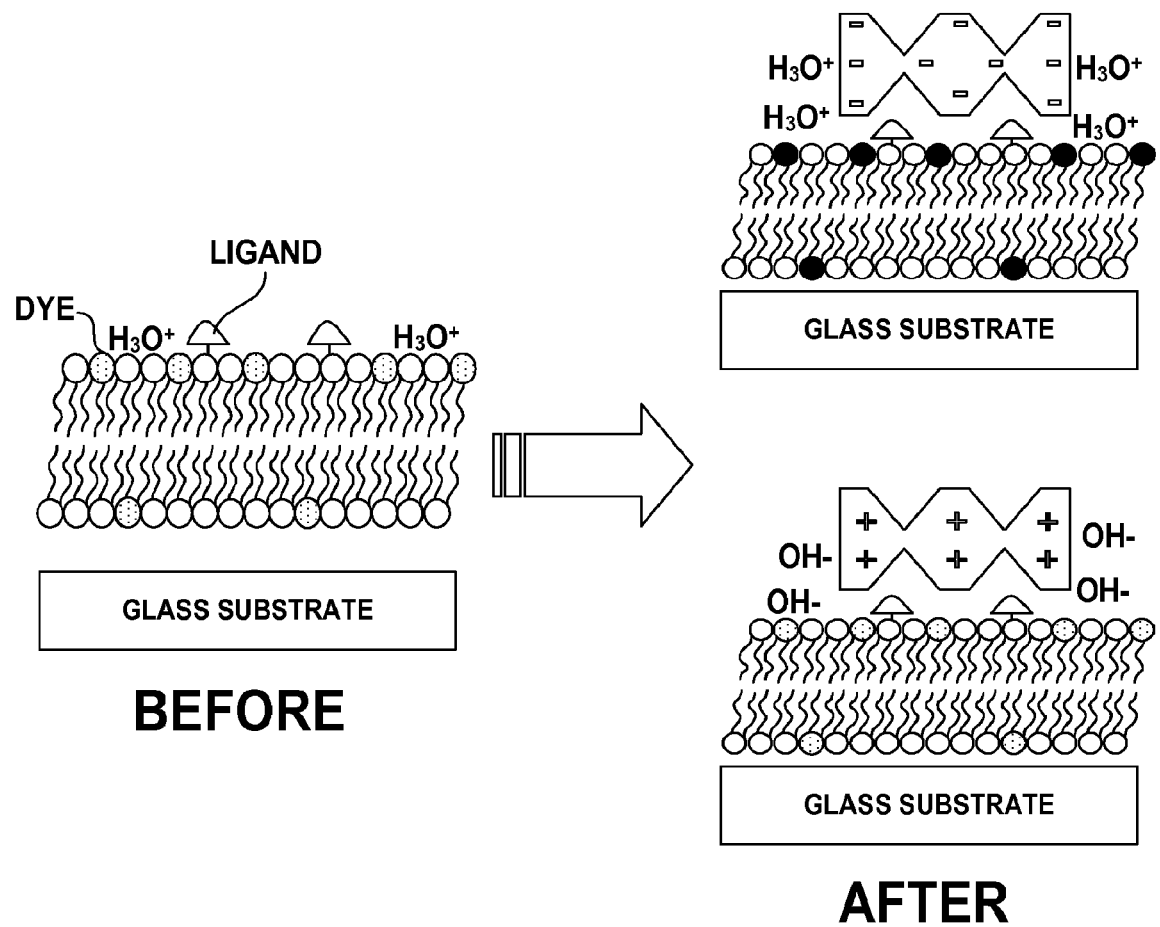
FIG. 31. Depiction of experiments using a bulk solution comprising positively charged protein versus a negatively charged protein.
Figure 32:
FIG. 32. Parameters of avidin (net positively charge) and streptavidin (net negative charge) as relevant to the methods described herein.
Figure 33:
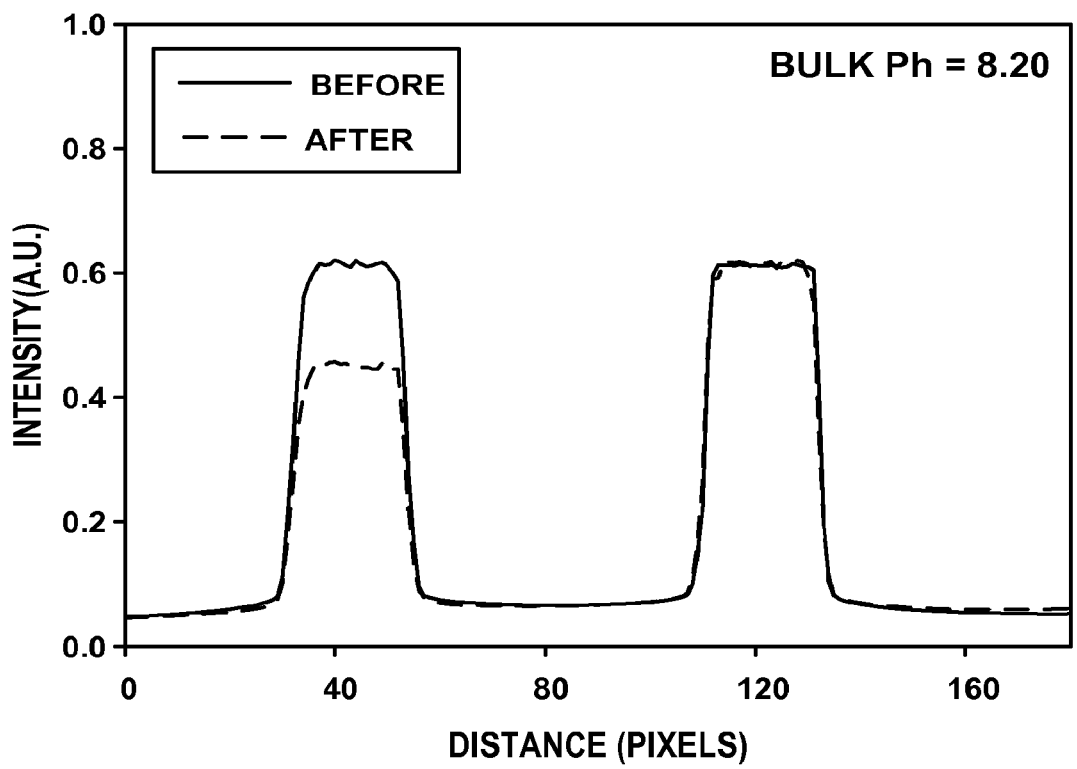
FIG. 33. Experimental line profiles of biotin/avidin and biotin/streptavidin in a POPC bilayer.
Figure 34:
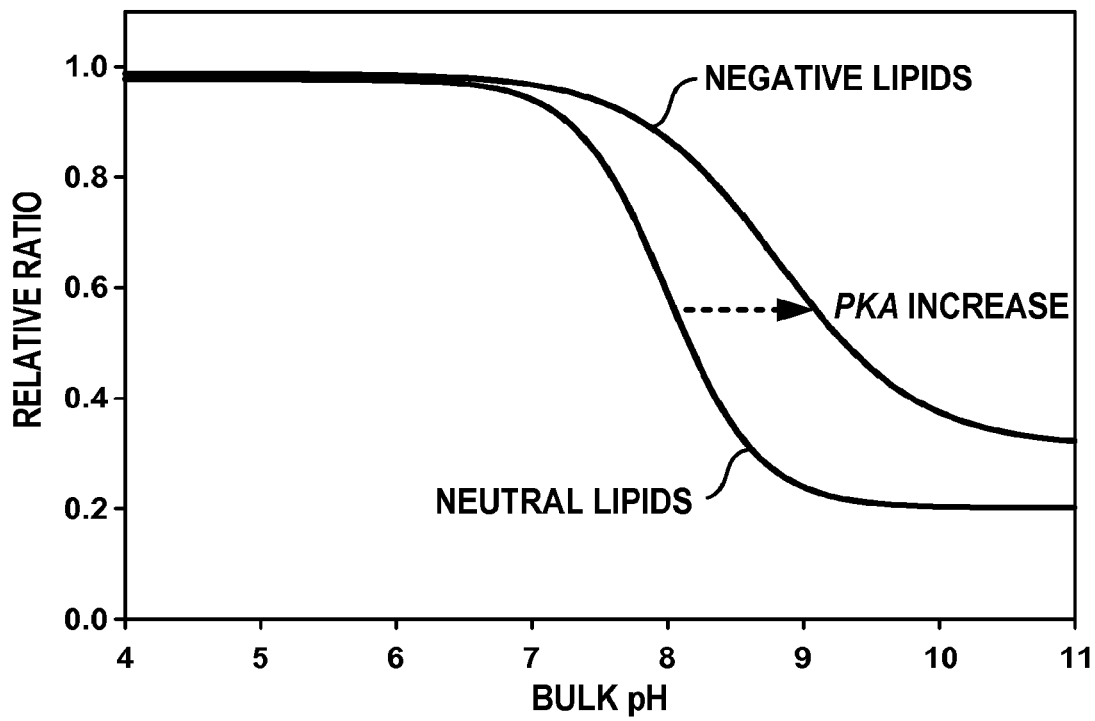
FIG. 34. Shifts in titration curves depending on the introduction of negatively charged lipids to a POPC bilayer.
Figure 35A:
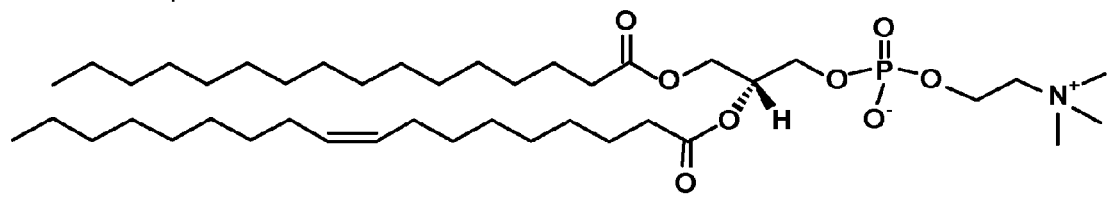
FIG. 35. Structures of lipids employed in some experiments described herein.
Figure 35B:
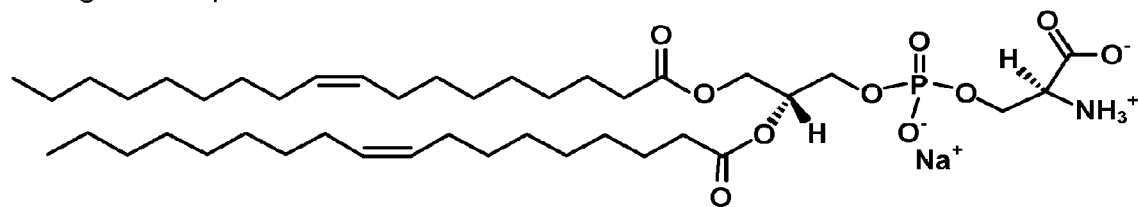
Figure 36A:
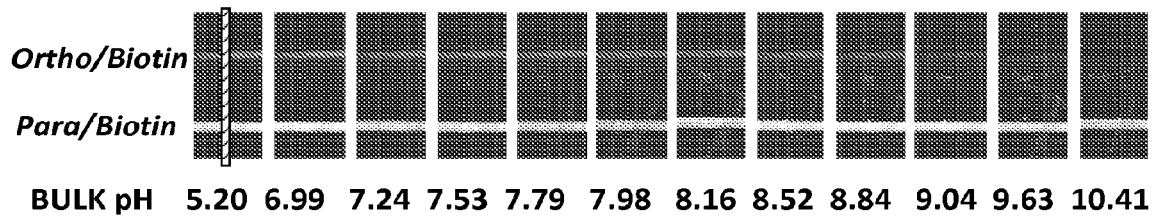
FIG. 36. Adding 20 mol % DOPS (a negatively charged lipid) to the membranes shifts the apparent $pK_A$ of ortho-Texas Red® DHPE to a more basic value with respect to the one found in FIG. 15b. The shift is by 0.44 pH units.
Figure 36B:
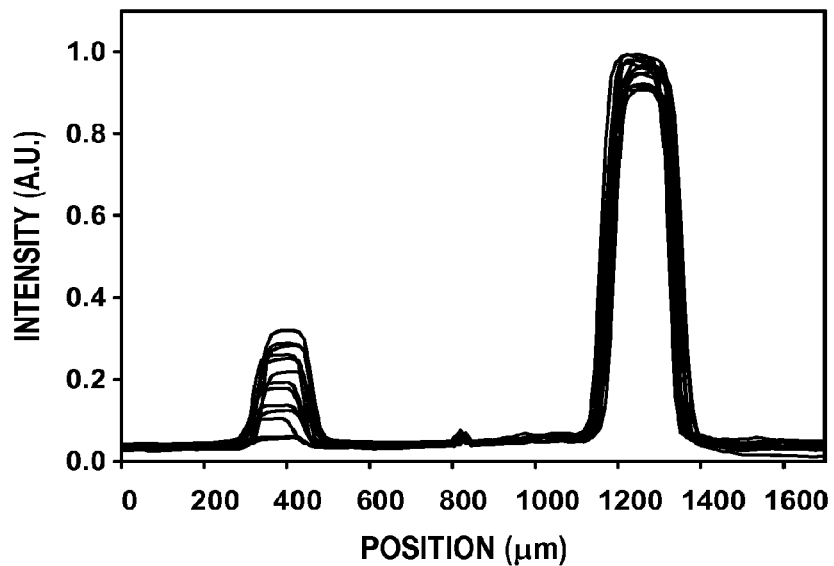
Figure 36C:
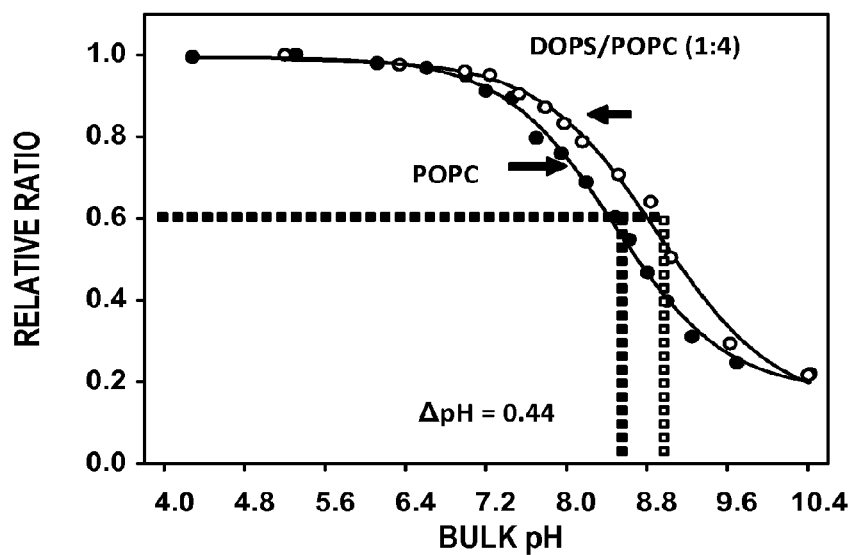
Figure 37:
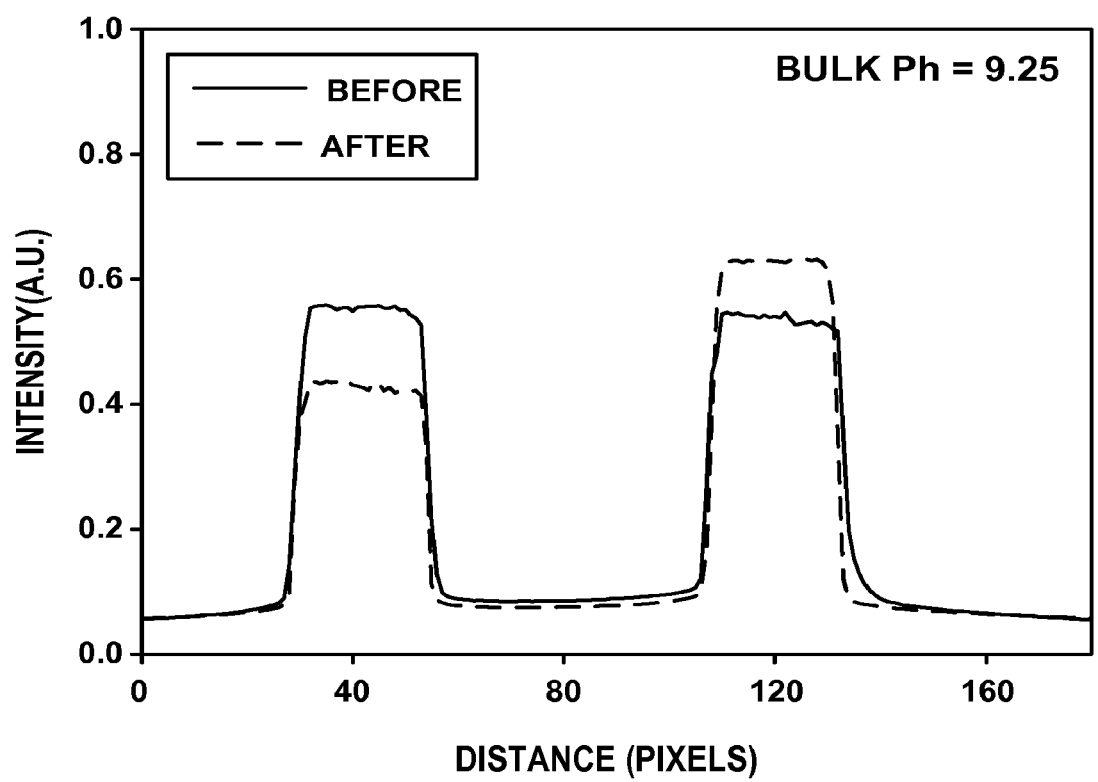
FIG. 37. Experimental line profiles of biotin/avidin and biotin/streptavidin in DOPS/POPC (1:4).

The results shown in FIG. 10 demonstrate remarkable sensitivity while using only 0.03 mol % ortho-Texas Red® DHPE. Indeed, the LOD value is roughly 0.04% of the $K_D$ value found in FIG. 9. Much lower LODs can be achieved when the ortho-Texas Red® DHPE concentration is higher as shown in FIG. 30 where it is lower than 10 fM. By contrast, corresponding SPR imaging (SPRI) data typically show detection limits that are 2 orders of magnitude less sensitive if the signal is not otherwise amplified by subsequent chemical processing steps (Lee, H. J., et al., *Anal. Chem.* 78:6504-6510, 2006). The best SPR data obtained from averaging signal over an entire sample (non-imaging mode) could perhaps approach the quality of data provided herein (Yang, C. Y., et al., *Lab on a Chip* 5:1017-1023, 2005). However, data from SPR systems have already been carefully optimized and no possibility for multiplexing exists without a corresponding loss of signal to noise.

In some embodiments, the sensitivity limits obtained from data in FIG. 10 may be improved (e.g., substantially improved) by simple modifications of the current experiment. For example, the ortho-Texas Red® DHPE and/or biotin-PE concentrations in the membrane may be modulated. LOD may also be improved (e.g., significantly improved) by making side-by-side measurements with ortho-Texas Red® and para-Texas Red® dyes in neighboring microfluidic channels that have otherwise identical membrane chemistry. Such measurements may be particularly valuable because the ultimate sensitivity limit in FIG. 10 may be related to fluctuations in the intensity of the illumination source as well as a small degree of photobleaching in the sample (Lord, S. J., et al., *J. Phys. Chem. A* 111:8934-8941, 2007). Using the pH insensitive para-Texas Red® DHPE dye as a reference system may enable these sources of noise to be eliminated and, hence, significantly improve upon the ±0.3% error bars already obtained.

As noted above, the intrinsic sensitivity of this technique may depend upon how many surface bound proteins are needed to detect a change in fluorescence at the 99% confidence level. In the studies shown above, 0.5 mol % biotin-PE was employed and 4×4 pixel binning was used for detection. This means that each 16 µm$^2$ area gave rise to a separate signal. The area per lipid molecule in the membrane is known to be 0.65 nm$^2$. Therefore, the results in FIG. 10 correspond to an LOD of ~250 IgG molecules/µm$^2$. This non-optimized result is within a few orders of magnitude of single molecule measurements. A system optimized in accordance with the present disclosure, in some embodiments, may be capable of detecting less than 10 proteins/µm$^2$ and/or single molecules. This is consistent with the notion that each protein will activate multiple fluorophores. Where this occurs, it would constitute far better sensitivity than SPR. Where this assay is already being performed in imaging mode, many separate interactions may be detected simultaneously with the same sensitivity by using lithographic patterning techniques (Cremer, P. S. and T. L. Yang, *J. Am. Chem. Soc.* 121:8130-8131, 1999; Jung, S. Y., et al., *Chem Phys Chem* 6:423-426, 2005).

The data shown in FIGS. 7-10 suggest that unprecedented sensitivity may be achieved from the biotin/anti-biotin binding system. Nevertheless, it may be that this is probably one of the least sensitive ligand-receptor binding pairs that may be chosen. In some embodiments, for example, the LOD values for other systems may be even better. Indeed, the biotin/anti-biotin assays were performed with a polyclonal IgG antibody fraction from rabbit raised against biotin conjugated KLH (keyhole limpet hemocyanin). This antibody has a isoelectric point (pI) value between 6.0 and 6.5 and bears only a slight negative charge at pH 7.8 as determined by measurements with pressure-mediated capillary electrophoresis (Williams, B. A. and G. Vigh, *Anal. Chem.* 69:4410-4418, 1997).

Figure 11:
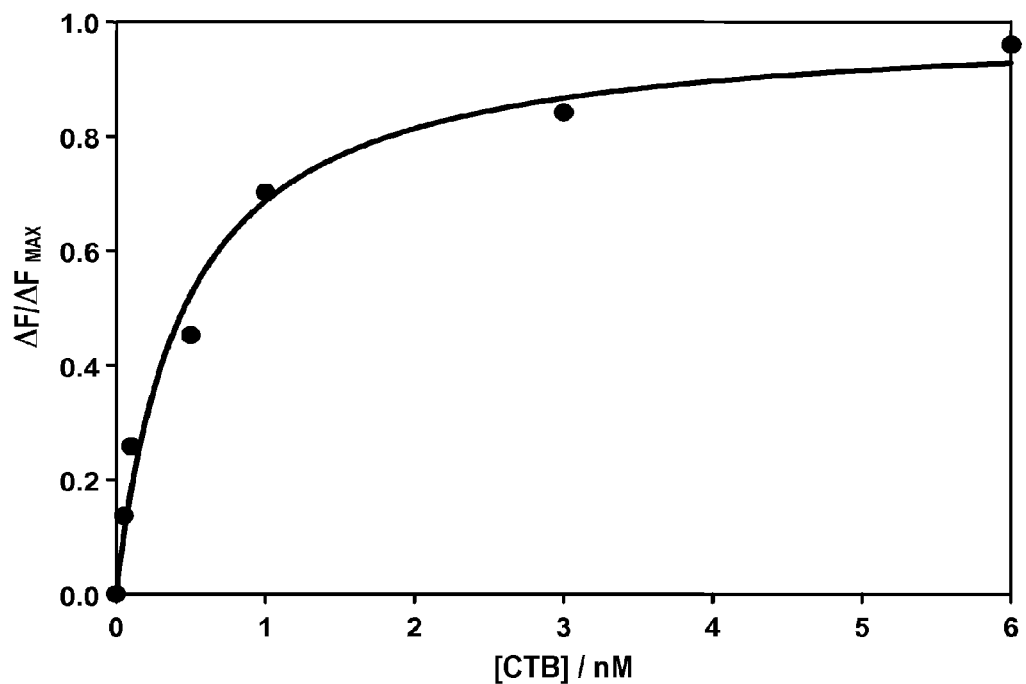
FIG. 11. The binding of cholera toxin B subunits to 0.25 mol % GM$_1$ in POPC membranes.

Examples of other ligand-receptor interactions that may be tested and/or used may include cholera toxin/$GM_1$ and/or concanavalin A/mannose binding. Even better sensitivity may be achieved in these cases because both concanavalin A and cholera toxin are further from their isoelectric points at pH 7.8. For example, POPC membranes were doped with 0.25 mol % $GM_1$ and 0.03 mol % ortho-Texas Red® DHPE. The binding of cholera toxin B subunits was monitored using a microfluidic assay and the abstracted binding curve is shown in FIG. 11.

As can be seen, excellent binding data are achieved for this system with $K_D$=0.45 (±0.13) nM. This $K_D$ value is in excellent agreement with literature data obtained by fluorescently tagging the toxin molecules (Shi, J., et al., *J. Am. Chem. Soc.* 129:5954-5961, 2007). Because the equilibrium dissociation constant of this system is more than 50 times tighter than the one for biotin/anti-biotin, one would expect the detection limit to be 100 fM or even better. This may be tested by probing the LOD for this system. Again, bulk concentration and/or surface concentration values may be obtained.

Most proteins possess a net negative charge near physiological pH. Under these circumstances, it is expected that the fluorescence intensity will rise when protein binds at the interface. The data in FIG. 8 are a good example of this. In some embodiments, an assay may work almost equally well, however, for proteins which are positively charged. In this case, the fluorescence intensity should decrease because the local pH at the surface increases upon protein binding. Therefore, the assay would be a "turn-off" rather than a "turn-on" sensor. Traditionally, "turn-off" sensors are deemed to be less desirable than "turn-on" sensors because one is often unsure if the analyte of interest is responsible for turning off the signal or if an unknown external environmental factor plays a role. One may be concerned that, in the case of pH sensitive biosensors, photobleaching of the dye molecules will decrease the fluorescence signal and could theoretically lead to false positive measurements. According to some embodiments of the present disclosure, however, this may not be a problem because all measurements may be referenced against the pH insensitive para-Texas Red® control system. In other words, in some embodiments, an assay may include simultaneously measuring the relative difference between the ortho- and para-Texas Red® fluorescence channels as analyte is flowed over the lipid bilayers. These dyes may be suitable for these relative measurements because, in part, the relative photo-stability of the two dyes are nearly identical within experimental error. Indeed, any environmental response which destroys one dye would be expected to also destroy the other. The only important difference between these two chemical isomers may be their pH response.

Biotin/avidin and biotin/streptavidin binding systems may be used to test the relative performance of "turn on" and "turn off" assays. Identical membranes containing biotin-PE as well as the pH sensitive dye may be used in both cases. Streptavidin, which has a pI of 6.4 (Skander, M., et al., *J. Am. Chem. Soc.* 126:14411-14418, 2004), is negatively charged at pH 7.8. Therefore, the sensor may act as a standard "turn on" sensor. On the other hand, avidin, which has a pI of 10.4

(Skander, M., et al., *J. Am. Chem. Soc.* 126:14411-14418, 2004), is positively charged at pH 7.8. Therefore, the sensor will "turn off" as protein is introduced. Detection limits may be directly compared between these two systems and any environmental responses that affect the ability of this assay to work in both directions may be assessed.

It is, of course, possible to design a system that "turns-on" when the surface pH is raised. Fluorescein and hydroxycoumarin derivatives are typical examples of fluorophores that that are activated upon deprotonation (Meidan, V. M., et al., *Biochim. Biophys. Acta* 1464:251-261, 2000; Fromherz, P., *Method. Enzymol.* 171:376-387, 1989). Both dyes may be tuned to work near physiological pH. Moreover, fluorescein and its derivates are commonly used pH indicators for monitoring bulk solution conditions (Ma, L.Y., et al., *Spectrochim. Acta. A* 60:1865-1872, 2004). However, employment of fluorescein for monitoring ligand-receptor interactions would be more problematic. Indeed, the type of sensors used according to some embodiments herein may require highly photostable states in order to obtain accurate data in these heterogeneous binding assays. Unfortunately, fluorescein is several times less photostable than Texas Red® DHPE (Lord, S. J., et al., *J. Phys. Chem. A* 111:8934-8941, 2007). Hydroxycoumarin exhibits a resistance to photobleaching that is not optimal in comparison to rhodamine dyes, as explained herein.

In some embodiments, ligand-receptor measurements may be made at or near pH 7.8 and/or at other bulk pH values offset from this number. For example, some binding events are only activated under acidic conditions (Goerges, A. L. and M. A. Nugent, *J. Biol. Chem.* 279:2307-2315, 2004). Thus, some assay embodiments may be performed over a bulk pH range from approximately 4.3 to 11.3.

Figure 6:
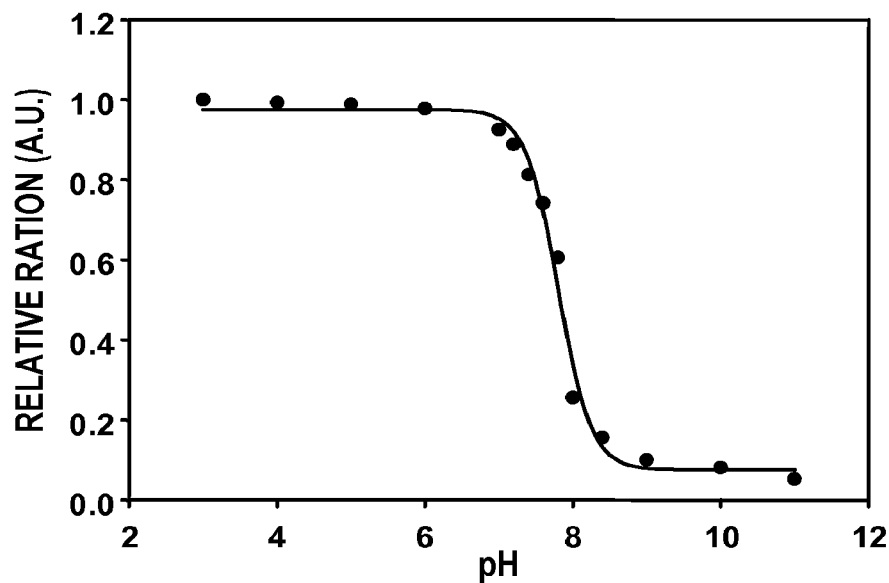
FIG. 6. Titration curve for the ortho-conjugated isomer of Texas Red® DHPE in a supported phospholipid bilayer. The circles represent fluorescence measurements and the solid line is a fit to the data. Note: more data points are plotted in FIG. 6 than are shown in FIG. 5 for the sake of clarity.
Figure 12A:
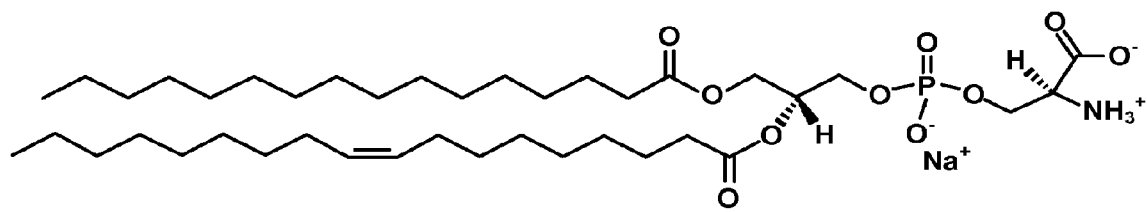
FIG. 12. Molecular structures for (a) POPS and (b) DDAB.
Figure 12B:
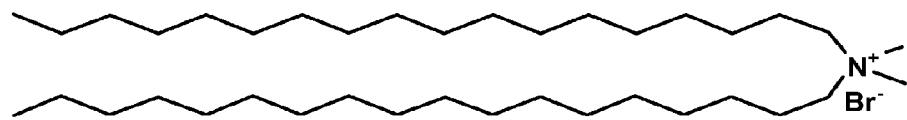

The titration curve in FIG. 6 clearly shows that the apparent $pK_A$ of ortho-Texas Red® DHPE is ~7.8 under the assay conditions described. However, this value may be manipulated by changing the membrane chemistry. For example, adding positively charged lipids to the membrane will repel hydronium ions from the interface, while the addition of negatively charged lipids will induce the opposite effect. These changes to the interfacial chemistry will shift the apparent $pK_A$ value for ortho-Texas Red® DHPE. In some embodiments, the apparent $pK_A$ of a pH sensitive dye may be varied by ±3.5 pH units. The apparent $pK_A$ of a dye may be tested in a microfluidic system by employing DDAB (dimethyldioctadecylammonium (bromide salt)) as the positively charged lipid component and POPS (1-palmitoyl-2-oleoyl-sn-glycero-3-[phospho-L-serine] (sodium salt)) as the negatively charged lipid component. The structures for these two species are provided in FIG. 12. These charged amphiphiles may be desirable because they are well known to incorporate into phospholipid membranes at concentrations ranging from 0 to 25 mol % (Senthilathipan, V. and G. Tollin, *Photochem. Photobiol.* 46:537-542, 1987). Moreover, they may not phase segregate or drastically change the phase transition properties of the membrane under the conditions at which they will be employed (Wagner, M. L. and L. K. Tamm, *Biophys. J.* 81:266-275, 2001).

One potential concern about modulating surface charge to change the apparent $pK_A$ value of the fluorescence dye is that such changes could potentially also change the equilibrium dissociation constants of a particular binding system via an electrostatic effect. For example, negatively charged proteins will be attracted to positively charged surfaces (Kloss, A. A., et al., *Langmuir* 16:3414-3421, 2000). Such effects may be offset, in some embodiments, by including sufficient salt (e.g., greater than 50 mM NaCl) in the bulk solution to screen the charged interface (Mauk, M. R., et al., *Biochemistry* 21:1843-1846, 1982). Moreover, bilayers provide excellent resistance to non-specific adsorption. Nevertheless, it may be desirable to monitor changes in $K_D$ values and/or number densities of non-specifically adsorbed proteins under a variety of different conditions to ensure that this is applicable to a particular set of conditions.

Demonstration of very low detection limits and high selectivity with simple laboratory solutions may be a first step in developing a new biosensor. Ultimately, however, it may be desirable to prove an assay's selectivity in the presence of a variety of interferants. Standard tests for selectivity may include being able to monitor a particular ligand/receptor interaction in the presence of blood plasma, urine, milk, or tap water. In some embodiments, antibody/antigen and cholera toxin/$GM_1$ interactions may be tested in the presence of blood plasma. Obtaining high selectivity for a pH sensitive assay may depend upon the ability of a phospholipid membrane to resist non-specific protein adsorption. Indeed, non-specific adsorption of plasma proteins would lead to a shift in the interfacial pH in much the same way as specific adsorption. According to some embodiments of the present disclosure, fluid phospholipid membranes may be particularly good at resisting non-specific protein adsorption. A system may be challenged, in some embodiments, with plasma solutions both in the presence and absence of real analytes (e.g., antibodies and cholera toxin). The effect of interferants on the LOD of a system, if any, may be monitored. In addition, the effect of adding a lipopolymer to the membrane may also be checked.

For many applications of a pH sensitive biosensor assay, one is effectively concerned with the smallest change in fluorescence that can be measured. Under those conditions the change in the measured fluorescence with the quantity of adsorbed protein is almost perfectly linear. This is because the relative fluorescence of ortho-Texas Red® DHPE changes almost perfectly linearly with pH value around the middle of the titration curve (FIG. 6). On the other hand, to obtain the type of thermodynamic data shown FIGS. 7-9, the dynamic range of the assay must also be considered. Specifically, the fluorescence increased approximately 70% from the condition where no protein was bound to the point where the surface was saturated with antibodies in FIG. 8. This data was obtained by starting just below the middle point of the dye's titration curve and the quantitative increase was from ~0.45 to ~0.77 of the maximum possible fluorescence value when all the dye molecules are protonated. Judging from FIG. 6, the linear range of this assay extends from ~0.20 to ~0.80 of the maximum possible fluorescence intensity of ortho-Texas Red® DHPE.

To obtain thermodynamic data for biotin/anti-biotin, 0.5 mol % biotin-PE was employed. The surface may be completely packed with antibody at saturation if ~1 mol % biotin-PE is employed. This should lead to a fluorescence increase from ~0.20 to ~0.80 of the relative maximum. An antibody/antigen assay may be performed under conditions where linearity can be assumed regardless of the ligand density in the membrane. This is because the protein has a relatively large footprint and is not very highly charged. On the other hand, other proteins contain a higher charge density. For these proteins, it will be necessary to determine the maximum concentration of ligand that maybe incorporated into the bilayer while still achieving linearity. The dynamic range for an assay may be increased in some embodiments. In the foregoing example, the assay goes from the near fully "off" position to the nearly fully "on" over about 1 pH unit (FIG. 6). This narrow titration range is excellent for achieving a good LOD value, but not necessarily optimal for measuring thermodynamic binding properties at the highest ligand densities. The titration range observed in FIG. 6 may be widened (e.g., substantially widened) by using a heterogeneous mixture of lipids to make the membrane.

As noted herein, bilayer systems are excellent platforms for measuring ligand-receptor binding because they possess the same two-dimensional fluidity as cell membranes and are particularly resistant to non-specific protein adsorption (Castellana, E. T. and P. S. Cremer, *Surf Sci. Rep.* 61:429-444, 2006). Nevertheless, in some embodiments, a pH-based measurement may be performed in the absence of a supported membrane. In fact, in some embodiments, this sensing concept is applicable to any platform that contains a pH sensitive dye-conjugated substrate and a bulk analyte solution which can be introduced above it. For example, an assay may include a bead-based assay that can be read out with a standard plate reader in a 96 or 384 well format.

Silica and polystyrene beads are inexpensive and commercially available in a variety of different diameters. Bead-based assays may be created using standard diameter spherical silica beads (e.g., 2 μm). Beads may be derivatized by silane chemistry to present three different chemical moieties: (1) a target ligand, (2) a pH sensitive dye molecule, and (3) a polyethyleneglycol (PEG) coating. A schematic diagram of an example system is shown in FIG. 13.

The dye and ligand-terminated silanes play the same role in this assay as they do in assays employing planar supported lipid bilayers. On the other hand, a PEGylated coating may be desirable and/or necessary in this case to resist non-specific adsorption of analyte molecules to the bead surface because protein molecules may otherwise adsorb to the bare aqueous/silica interface.

Figure 13:
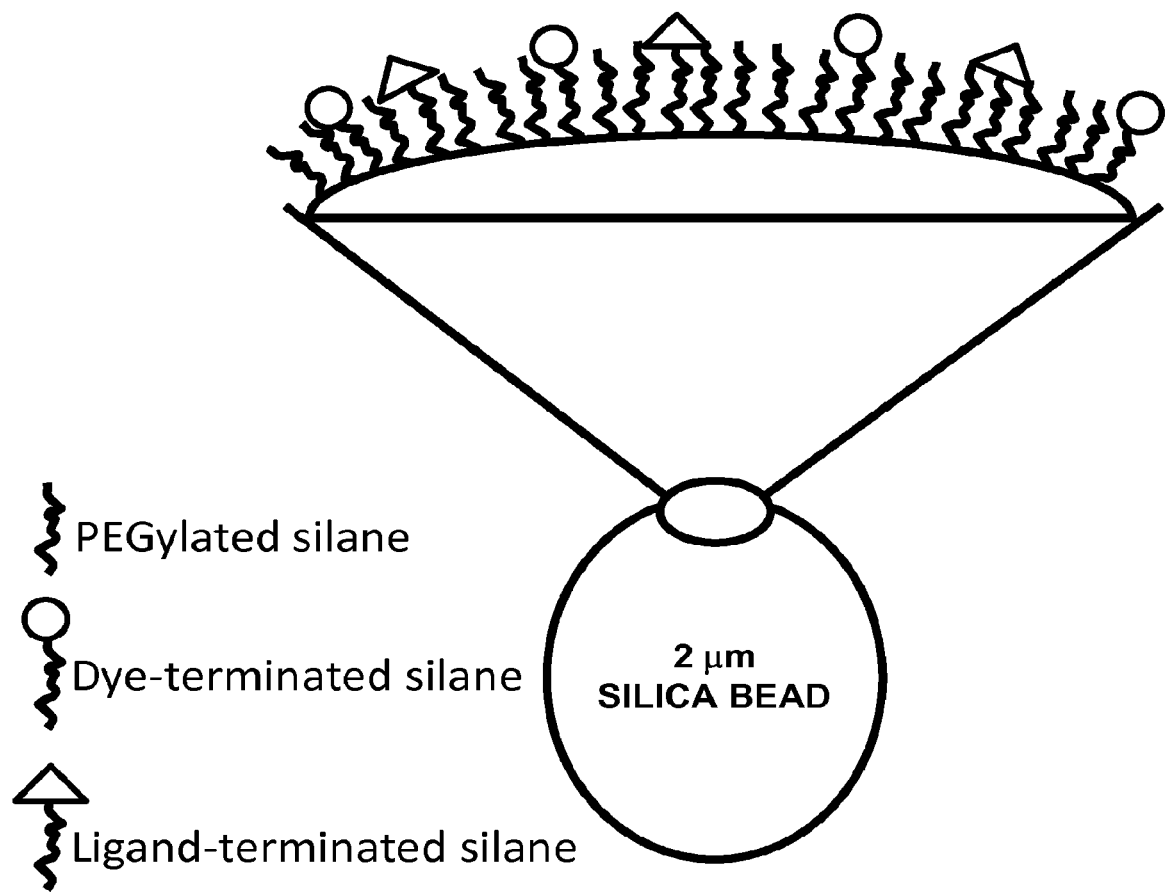
FIG. 13. A 2 µm silica bead derivatized with silane molecules at the surface. The surface chemistry is not drawn to scale.

In some embodiments, beads may be prepared as shown in FIG. 13 using a biotin-PEG-triethoxysilane molecule as the ligand moiety. This ligand may be desirable for two reasons. First, it allows a direct comparison with the biotin/anti-biotin, biotin/streptavidin, and biotin/avidin experiments for lipid bilayers described above. Second, it is commercially available with a variety of PEG chain lengths, which will permit optimization of the polymer spacer length that is to be employed. In addition to the ligand, the PEGylated silane is also commercially available in a variety of different chain lengths. Of course, the dye-terminated silane is not a commercial molecule, but can be made in a single step. For example, ortho-Texas Red®-PEG-triethoxysilane may be synthesized from the appropriate amine-terminated PEG molecule, $NH_2$-PEG-triethoxysilane. The free amine will bind directly to the ortho-sulfonyl chloride to make ortho-Texas Red®-conjugated silane. The para-Texas Red® analog may also be made in an analogous fashion for reference experiments. The ortho- and para-sulfonyl chloride molecules may be separated before conjugation by high pressure liquid chromatography (HPLC).

Upon fabrication, biotin and dye-conjugated beads may be transferred in aqueous solution into individual wells in a 96 well assay format. Analyte protein molecules may be introduced subsequently into individual wells. If the correct ligand/receptor binding pair is formed, then the same local pH shift at the bead interface should occur as the one already found for the supported bilayer assays. A bead assay can be read using a standard fluorescence plate reader. Many of the same control experiments may need to be performed in this format as will be performed with the supported bilayer assay. Namely, detection limits of the assay and/or the effects of non-specific adsorption (if any) may be assessed. The latter may be done, for example, by probing the fluorescence changes upon the introduction of a non-specific antibody (i.e., anti-DNP) into a well. The specificity of this platform in the presence of interferants may be evaluated. The chain length of the PEG moiety may be modulated in order to optimize the assay against non-specific adsorption according to some embodiments. The concentration of the ligand-conjugated and/or dye-conjugated silanes may be modulated to optimize the LOD, while continuing to minimize non-specific adsorption. The size and concentration of the beads employed in this assay may also be modulated.

In some embodiments, the performance of bead assays may be directly compared with data obtained from supported bilayer assays. Supported bilayers may have less non-specific adsorption and better selectivity according to some embodiments. Indeed, the two-dimensional fluidity of the supported bilayer assays allows them to achieve better selectivity than could be obtained by covalently bound ligands. Bilayer systems may be designed to be compatible with microfluidic technologies. On the other hand, the technologies associated with fluorescent plate readers are less expensive than a fluorescence microscope (only a few thousand dollars for a plate reader). Plate reader assays have already been commercialized and are relatively easy to use by the non-expert. A potentially important comparison to be made involves the LOD of each type of device. Supported bilayer-based devices may be able to detect fewer proteins. However, the plate reader device will be measuring fluorescence from a bulk solution and may have a very low detection limit if the bulk analyte concentration is considered.

Most proteins possess a relatively modest charge per unit mass near physiological pH compared with DNA. Therefore, one typically wishes to employ a stable fluorophore as the pH sensitive interfacial detection element. Moreover, a suitable control system against which pH changes may be measured may be required. Texas Red® DHPE satisfies these criteria (FIG. 14). Texas Red® DHPE is made from Texas Red® sulfonyl chloride via addition of the free amine from the head group of 1,2-dihexadecanoyl-sn-glycero-3-phosphoethanolamine (DHPE). Because Texas Red® sulfonyl chloride consists of an ortho and a para isomer (Corrie, J. E. T., et al., *Bioconjugate Chem.* 12:186-194, 2001), the conjugated lipid product is ultimately an isomeric mixture. As discussed herein, the ortho-conjugated isomer fluoresces when the sulfonamide is protonated, but not when it is deprotonated (FIG. 14a) (Marchesini, S., et al., *Biochem. Int.* 27:545-550, 1992). By contrast, the para isomer of Texas Red® DHPE is a pH insensitive dye and may be employed as a reference for determining relative changes in fluorescence intensity of the ortho-conjugated dye (FIG. 14b).

The use of ortho-conjugated Texas Red® DHPE as a reporter of local pH modulation in supported lipid bilayers is demonstrated herein. The apparent $pK_A$ of this molecule in an SLB containing 0.5 mol % biotin-cap-PE on glass was found to be 7.8±0.1. The dye molecule could be used to generate a binding curve for the biotin/anti-biotin pair at the SLB interface. The equilibrium dissociation constant, $K_D$, was found to be 24±5 nM. This value is in good agreement with measurements made by total internal reflection fluorescence microscopy (TIRFM) using dye-labeled proteins. Moreover, unless otherwise noted, the limit of detection (LOD) for the antibody was ~350 fM at the 99% confidence level. This is about 69,000 times smaller than the corresponding $K_D$ value. In imaging mode, the assay could detect fewer than 400 IgG molecules in a single 4×4 binned pixel region. Thus, this assay compares extremely favorably with previously developed detection techniques.

Materials. Texas Red® DHPE was purchased from Invitrogen (Eugene, Oreg.). Rabbit polyclonal anti-biotin antibody came from Rockland (Gilbertsville, Pa.), while affinity purified goat polyclonal anti-dinitrophenyl (anti-DNP) IgG was obtained from Axxora (San Diego, Calif.). Cholera toxin B from *Vibrio cholerae* was purchased from Sigma-Aldrich (St. Louis, Mo.). POPC (1-palmitoyl-2-oleoyl-sn-glycero-3-phosphocholine), biotin-cap-PE (1,2-dipalmitoyl-sn-glycero-3-phosphoethanolamine-N-(cap biotinyl) (sodium salt), DOPC (1,2-dioleoyl-sn-glycero-3-phosphocholine), DPPC (1,2-dipalmitoyl-sn-glycero-3-phosphocholine), ganglioside $GM_1$ (brain, ovine-ammonium salt), and cholesterol were obtained from Avanti Polar Lipids (Alabaster, Ala.). Thin layer chromatography (TLC) was carried out using precoated plates made of silica gel with a pore size of 60 Å and a layer thickness of 250 μm (Silica Gel 60 $F_{254}$, EMD Chemicals Inc., Germany). Purified water was produced from a NANOpure Ultrapure Water System (18.2 MΩ·cm, Barnstead, Dubuque, Iowa). Glass coverslips (25×25 mm, No. 2, Corning Inc.) were used as solid supports for the bilayers. Polydimethylsiloxane (PDMS, Dow Corning Sylgard® Silicone Elastomer-184) was obtained from Krayden, Inc (El Paso, Tex.).

The Separation of Texas Red® DHPE Isomers. The two isomers of Texas Red® DHPE were separated by using a slightly modified form of other procedures (Daniel, S., et al., *J. Am. Chem. Soc.* 129:8072-8073, 2007). Briefly, small spots of the ortho/para mixture were made on a TLC plate from a 1 mg/mL chloroform solution. Next, the spotted plate was placed into a development chamber and ethanol (AAPER Alcohol and Chemical Co., Shelbyville, Ky.) was used as the eluent. Two bands were formed, whereby the upper band was the para isomer and the lower band was the ortho isomer. Each band was recovered separately from the plate by carefully scraping the surface with a razor blade and re-suspending the dye/silica bead mixture in methanol. The silica was separated from the soluble organic material by filtration. Methanol could then be removed by using a rotary pump and further drying the sample under vacuum on a Schlenk line. TLC was rerun with a small portion of the isolated sample to confirm the purity of each isomer.

Preparation of Small Unilamellar Vesicles (SUVs). Lipids in the desired composition ratio were introduced into a glass vial in chloroform. The solvent was removed by passing a gentle stream of dry nitrogen over the solution. The resulting film was further dried under vacuum for 3 h. The film was then hydrated in a 10 mM phosphate buffered saline (PBS) solution containing 150 mM NaCl. After suspension of the lipid mixture, it was subjected to 10 freeze-thaw cycles and then extruded 10 times through two stacked polycarbonate membranes (Whatman) with 100 nm pores. The resulting SUVs prepared by this procedure were 70±10 nm in diameter as determined by dynamic light scattering (Brookhaven Instruments 90Plus Particle Size Analyzer). The final concentration of the lipid solutions employed for vesicle fusion experiments was 0.5 mg/mL. The vesicles were kept at 4° C. before use.

pH Titration and Buffer Preparation. 10 mM PBS solutions containing 150 mM NaCl were prepared at pH values ranging from 4.0 to 10.2 by mixing appropriate amounts of $Na_2HPO_4$, $NaH_2PO_4$, or $Na_3PO_4$. These pH values were chosen to locate the $pK_A$ value of ortho-Texas Red® DHPE. The pH could be adjusted to the desired value by the dropwise addition of HCl or NaOH. The pH was measured with a standard glass electrode setup. Such absolute measurements had an error of ±0.1 pH units associated with them. Changes in fluorescence, however, could be measured far more accurately. These changes in fluorescence intensity corresponded to relative shifts in interfacial pH as small as 0.002 pH units when a 40× objective was employed for making the measurements. Titration curves for the dye molecules in SLBs were obtained by systematically changing the pH of the bulk solution in a stepwise fashion. Fresh buffer was continuously flowed over the surface until no further changes in fluorescence intensity could be observed. The quality and fluidity of the supported bilayers as a function of pH was confirmed by fluorescence recovery after photobleaching (FRAP) measurements (Diaz, A. J., et al., *Langmuir* 24:6820-6826, 2008). Fluorescent micrographs of SLBs were captured with a standard epifluorescence microscope setup (Nikon Eclipse E800).

The fluorescence titration curve of the Texas Red® DHPE dye molecules was monitored in SLBs containing two narrow, parallel lines of bilayers with distinct dye chemistries. The first line contained 99.47 mol % POPC/0.50 mol % biotin-cap-PE/~0.03 mol % ortho-Texas Red® DHPE. The second line was identical, but contained para-Texas Red® DHPE instead of the ortho isomer. The surrounding lipid matrix was a 1:1:1 mixture of DOPC, DPPC, and cholesterol. This composition was chosen because diffusion of the dyes molecules from the narrow lines into the surrounding matrix was extremely slow. The two lines were formed sequentially by mechanically scratching the DOPC/DPPC/cholesterol bilayer and backfilling with the desired lipid mixture using the vesicle fusion method (Mao, H., et al., *Anal. Chem.* 74:379-385, 2002).

The titration curve for the Texas Red® DHPE dye molecules in the presence of a saturated anti-biotin protein monolayer on a supported membrane surface was obtained with the same bilayer as described above. In this case, however, a saturation concentration of IgG (500 nM) was first introduced into the bulk solution. Moreover, all fluorescence measurements as a function of pH were performed in the presence of 500 nM bulk protein concentration to ensure that the surface remained saturated with protein.

All experiments presented herein were conducted with 150 mM NaCl. Additional control experiments were performed with varying concentrations of salts up to 300 mM. The results showed that fluorescence changes upon protein binding were not affected within experimental errors when moderately high salt concentrations were present. This is to be expected because the Debye length is below 1 nm so long as there is at least 100 mM NaCl in the buffer solution (Israelachivili, J. N., *Intermolecular and Surface Forces*; 2nd ed.; Academic Press: San Diego, Calif., 1991).

Fabrication of Microfluidic Devices. Seven-channel microfluidic devices (130 μm wide, 15 μm deep, and separated by 160 μm spacing) were formed by conventional soft lithographic methods (Shi, J., et al., *J. Am. Chem. Soc.* 129: 5954-5961, 2007). First, glass substrates (soda-lime glass slides, Corning) were spin-coated with photoresist (Shipley 1827) and then exposed to UV light through a Kodak technical pan film photomask containing the appropriate image. After the substrates were treated in developing solution and baked overnight at 120° C., they were immersed in a buffered oxide etchant (BOE) to etch the glass. The BOE solution was prepared with a 1:6 ratio (v/v) of 48% HF (EMD Chemicals Inc., Germany) and aqueous $NH_4F$ (200 g in 300 mL purified water, Alfa Aesar, Ward Hill, Mass.) (Holden, M. A., et al., *Sensors Actuat. B* 92:199-207, 2003). The remaining photoresist was removed with acetone. Next, a degassed mixture of Sylgard silicone elastomer-184 and a curing agent (10:1 ratio (v/v)) was poured over the patterned glass substrate. The liquid PDMS was cured in an oven at 70° C. for 1 h and then peeled off the glass substrate. This elastomeric mold and a freshly cleaned glass cover slip were placed into a 25 W oxygen plasma for 30 s and immediately brought into contact to form the PDMS/glass device. The glass slides used in these experiments were cleaned in a boiling solution of ICN 7× (Costa Mesa, Calif.) and purified water (1:4 ratio (v/v)) for 30 minutes, rinsed with copious amounts of purified water, and dried gently under a flow of nitrogen gas. Finally, the glass substrates were annealed in a kiln at 450° C. for 5 h before introduction into the oxygen plasma.

Formation of Supported Bilayers. SLBs were formed on the walls and floors of microchannels by the spontaneous fusion of SUVs (Jung, H. S., et al., *Biophys. J.* 94:3094-3103, 2008). To do this, 5 µL of an SUV solution were injected into each channel immediately after the formation of a PDMS/glass device. The solutions were incubated in the channels for 10 minutes and then rinsed away with pure PBS buffer (pH 8.2) to remove excess vesicles.

To make binding constant measurements, varying concentrations of unlabeled antibody solutions were continually injected into each microchannel at a rate of 200 nL/min until the fluorescence intensity from the surface remained constant. This took up to ~5 h for the lowest protein concentration measurements.

Epifluorescence Microscopy. An inverted epifluorescence Nikon Eclipse TE2000-U microscope with a 10× air objective (N.A.=0.45) was used for FRAP studies. Laser radiation from a 2.5 W mixed gas $Ar^+/K^+$ laser (Stabilite 2018, Spectra Physics) was used to bleach a small spot (14 µm in diameter) in the supported bilayer sample.

Fluorescence imaging studies were performed with a Nikon Eclipse E800 fluorescence microscope (Tokyo, Japan) equipped with a MicroMax 1024 CCD camera (Princeton Instruments), a Texas Red® filter set (Chroma Technology, Bellows Falls, Vt.) and either a 4× air (N.A.=0.13) or a 10× air (N.A.=0.45) objective. An X-Cite 120 arc lamp (EXFO) was used as the light source for all experiments and all images were processed with MetaMorph software (Universal Imaging). Data acquisition for the limit of detection experiments was also performed in epifluorescence mode. In this case, a 40× oil immersion objective (N.A.=1.30) was used to monitor the fluorescence intensity.

Classical Binding Measurements. Binding measurements with labeled antibodies were performed inside microfluidic devices which were identical to those described above. Protein detection was done with total internal reflection fluorescence microscopy (TIRFM) (Jung, H. S., et al., *Biophys. J.* 94:3094-3103, 2008; Yang, T., et al., *J. Am. Chem. Soc.* 125: 4779-4784, 2003). Alexa Fluor®-594 tags were conjugated to the anti-biotin molecules using an Invitrogen labeling kit (Eugene, Oreg.) by following standard procedures. The labeled antibody solutions at various concentrations (PBS buffer, pH 8.2) were flowed through each microchannel until the bulk fluorescence intensity from the dye-labeled antibodies remained constant as judged by epifluorescence measurements. A 594 nm helium-neon laser beam (4 mW, Uniphase, Manteca, Calif.) was projected onto the sample with a line generator lens (BK7 for 30°, Edmund Optics, Barrington, N.J.) for TIRFM measurements. This created a uniform intensity profile perpendicular to the direction of flow of the microfluidic channels. On the other hand, the intensity of the beam parallel to the long axis of the channels corresponded to a Gaussian profile. The glass substrates for the microfluidic devices were optically coupled to a dove prism with index matching immersion oil (type DF, Cargille Laboratories, Cedar Grove, N.J.).

Figure 15A:
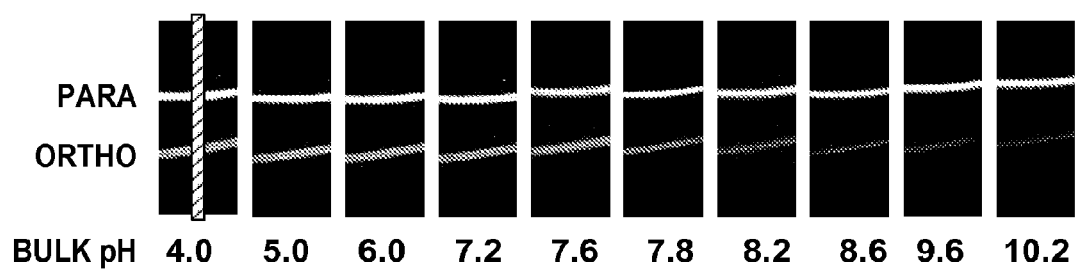
FIG. 15. (a) Fluorescence images of supported POPC bilayers containing para and ortho-conjugated Texas Red® DHPE in two adjacent bands. Each bilayer strip contained 0.5 mol % biotin-cap-PE and ~0.03 mol % of the respective fluorescent dye. The images were taken from pH 10.2 to pH 4.0. A 4× air objective was used to make these measurements. An example of the region from which intensity line profile data was abstracted is denoted with a red line in the first image. (b) Relative intensity for the ortho-conjugated isomer of Texas Red® DHPE as a function of pH. The black circles represent individual fluorescence measurements and the solid line is a sigmoidal fit to the data. Error bars representing standard deviation measurements from three data sets are denoted on each data point. To obtain the y-axis, the intensity of the ortho band was divided by the intensity of the para band at each pH value. This ratio was normalized to 1.0 at pH 4.0. All intensity ratios are relative to this normalization.

Titration Curves for ortho-Texas Red® DHPE. In a first set of experiments, the pH dependent responses of the ortho- and para-conjugated Texas Red® dyes were investigated in supported POPC bilayers with 0.5 mol % biotin-cap-PE. Titration experiments were systematically performed by changing the pH of the bulk solution stepwise from pH 10.2 to 4.0. Bulk solutions at a given pH value were continuously flowed into the device until the fluorescence intensity remained constant. Fluorescence images at each pH value were then captured (FIG. 15a). As illustrated, the intensity of the para band remained nearly unchanged, while the ortho band showed higher intensity at more acidic pH values. No evidence for hysteresis was observed by returning the pH back to 10.2 from 4.0 or even by cycling the pH several times. The normalized peak area of the ortho band relative to the para band as a function of pH is plotted in FIG. 15b and an apparent $pK_A$ value of 7.8±0.1 may be abstracted from the data.

Next, an assay was performed to determine how fast ortho-Texas Red® DHPE responds to bulk pH changes. To do this, two separated bilayer strips were formed containing the ortho and para dyes, respectively. Time-sequence fluorescence images were obtained as the bulk pH was abruptly increased from 4.0 to 10.2. The fluorescence micrographs and line profiles as a function of time are shown in FIG. 16. As illustrated, the fluorescence changed almost as abruptly as the pH could be raised (i.e. within a few seconds). Such a result is in agreement with the response of an ortho-conjugated sulforhodamine isomer in bulk aqueous solution, which may respond to pH changes on the millisecond time scale (Corrie, J. E. T., et al., *Bioconjugate Chem.* 12:186-194, 2001). Moreover, it appears that Texas Red® DHPE molecules in both leaflets of the bilayer are rapidly able to sense the pH jump.

Figure 17A:
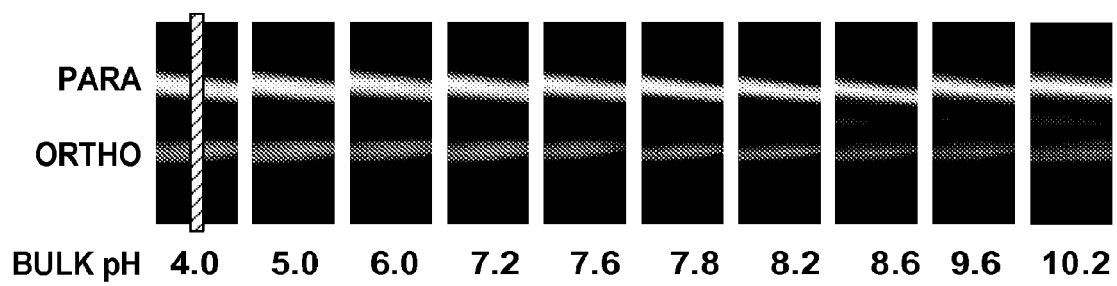
FIG. 17. (a) Epifluorescence images of para-Texas Red® DHPE (upper) and ortho-Texas Red® DHPE (lower) strips at different bulk solution pH values in the presence of a saturation concentration of anti-biotin. (b) Relative intensity ratio for ortho-Texas Red® DHPE as a function of pH. The black circles represent fluorescence measurements and the solid line is a sigmoidal fit to the data ($R^2$=0.99). To obtain the y-axis, the intensity of the ortho band was divided by that of the para band at each pH value and the value at pH 4.0 was set to 1.0. All other intensity ratios are relative to this value. Error bars representing standard deviation measurements from three data sets are denoted on each data point. A 10× air objective was used to make these measurements. The red line across the first image in (a) denotes an example of the region from which intensity line profile data were abstracted.
Figure 17B:
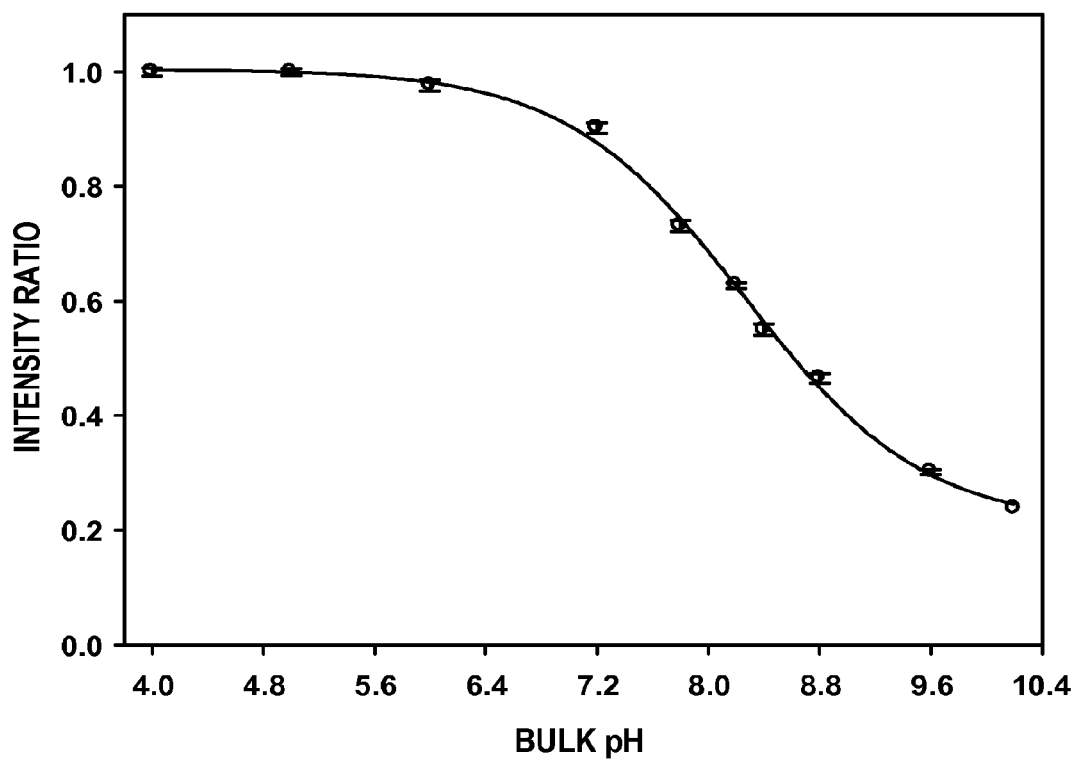

Titration Curve with a Saturated Protein Layer. In some embodiments, the ortho-Texas Red® DHPE isomer may be an excellent reporter for small changes in the local pH brought about by the binding of proteins from bulk solution. To demonstrate this principle, the biotin/anti-biotin antibody binding pair was employed as a test system. First, two separated bilayer strips were formed as described above. Then, the surface was saturated with anti-biotin IgG by the introduction of a 500 nM protein solution over the surface for 10 minutes. All subsequent measurements were made by tuning the solution pH value, but keeping the bulk IgG concentration constant. (The IgG molecules did not noticeably aggregate as the pH was tuned between 4 and 10.2. In fact, no changes in the activity of anti-biotin IgG were observed in the range of pH 4.0-10.2. This is to be expected as these proteins do not possess a single isoelectric point (pI) value as the population is polyclonal.) The results shown in FIG. 17 reveal an apparent shift of ~0.35 pH units with respect to the results in FIG. 15 (the apparent shift of ~0.35 pH units corresponds to the shift in the midpoint of the titration curve for FIG. 17b with respect to FIG. 15b as determined by a sigmoidal fit to the data), which were taken in the absence of bound proteins.

Binding Curve for Anti-Biotin Antibodies. To obtain the equilibrium dissociation constant for the biotin/anti-biotin system, POPC bilayers containing 0.5 mol % biotin-cap-PE and ~0.03 mol % ortho-Texas Red® DHPE were coated on the inside walls and floors of a seven channel PDMS/glass microfluidic device. Experiments were run in all channels at a bulk pH of 8.2. Concentrations of antibodies ranging from 0 to 200 nM were flowed continuously through the individual channels until the fluorescence intensity from the surface-bound dyes remained constant. Epifluorescence images from the device used in these experiments are shown in FIG. 18a. As illustrated, weaker and uniform fluorescence intensity was observed in all channels before the addition of protein. After the IgG molecules were introduced, however, the fluorescence intensity was strengthened in accordance with the bulk concentration of the antibodies.

Figure 15B:
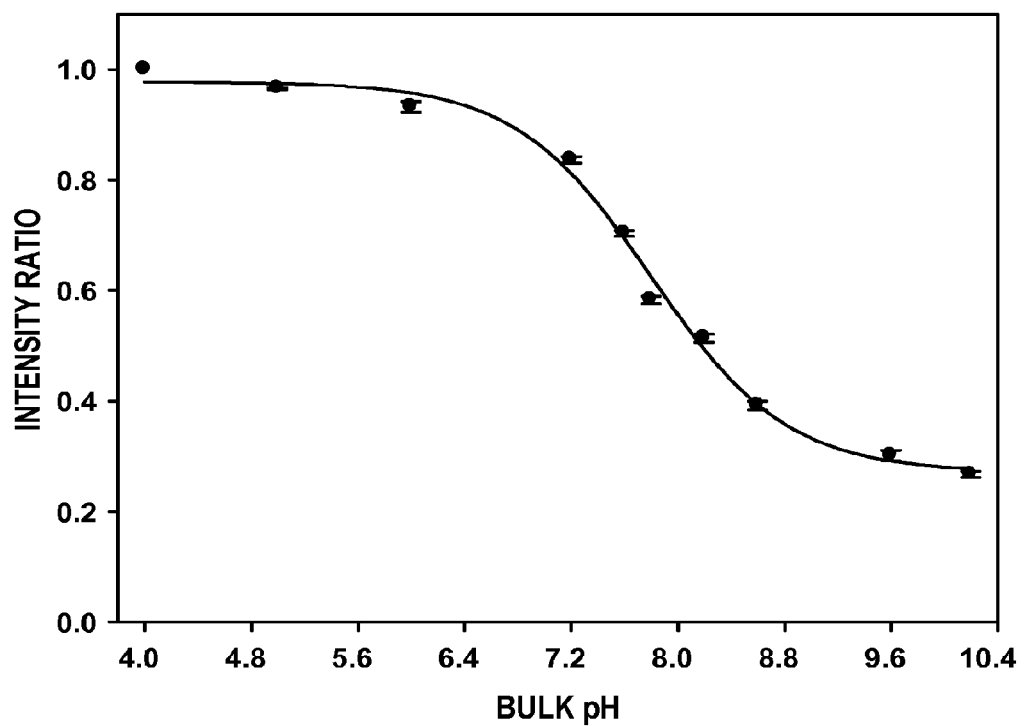
Figure 16A:
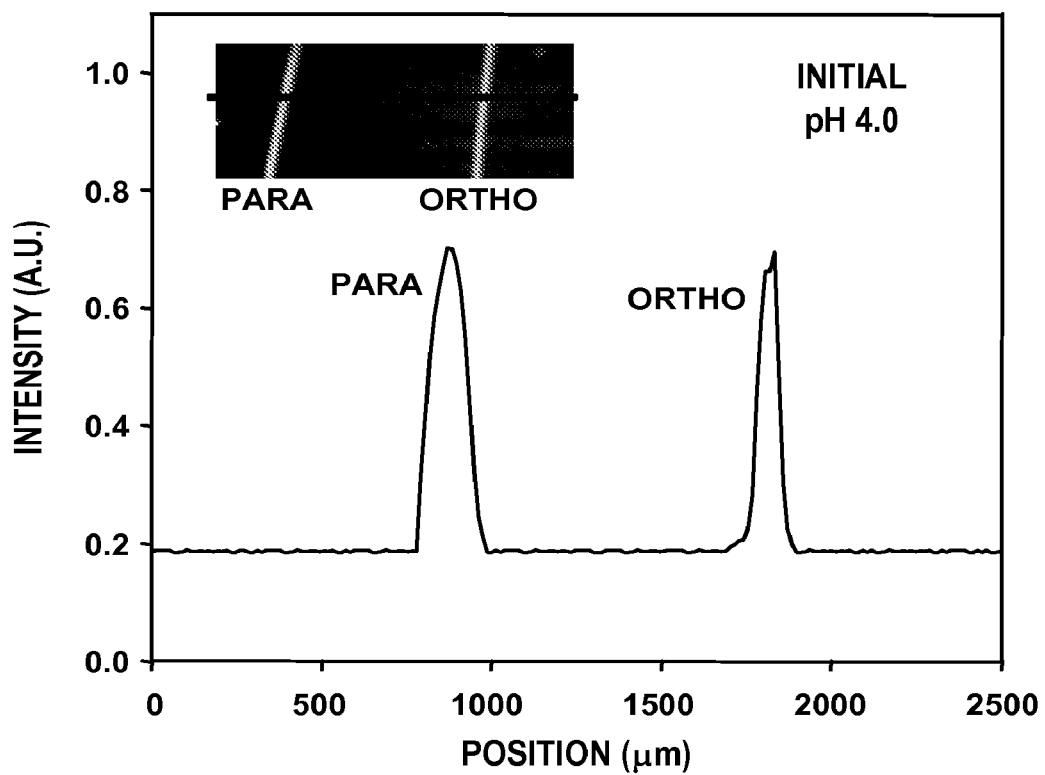
FIG. 16. The time response of ortho and para-conjugated Texas Red® DHPE bands in a supported bilayer to an abrupt jump in pH from 4.0 to 10.2. (a) pH originally set to 4.0, (b) buffer solution at pH 10.2 is flowed over the surface, (c) 2 s later, and (d) 3 s later. Both an epifluorescence image and a corresponding line profile are shown for each time period. An example of the region across which the line profile was taken is denoted with a red line in (a). A 4× air objective was used to make these measurements.
Figure 16B:
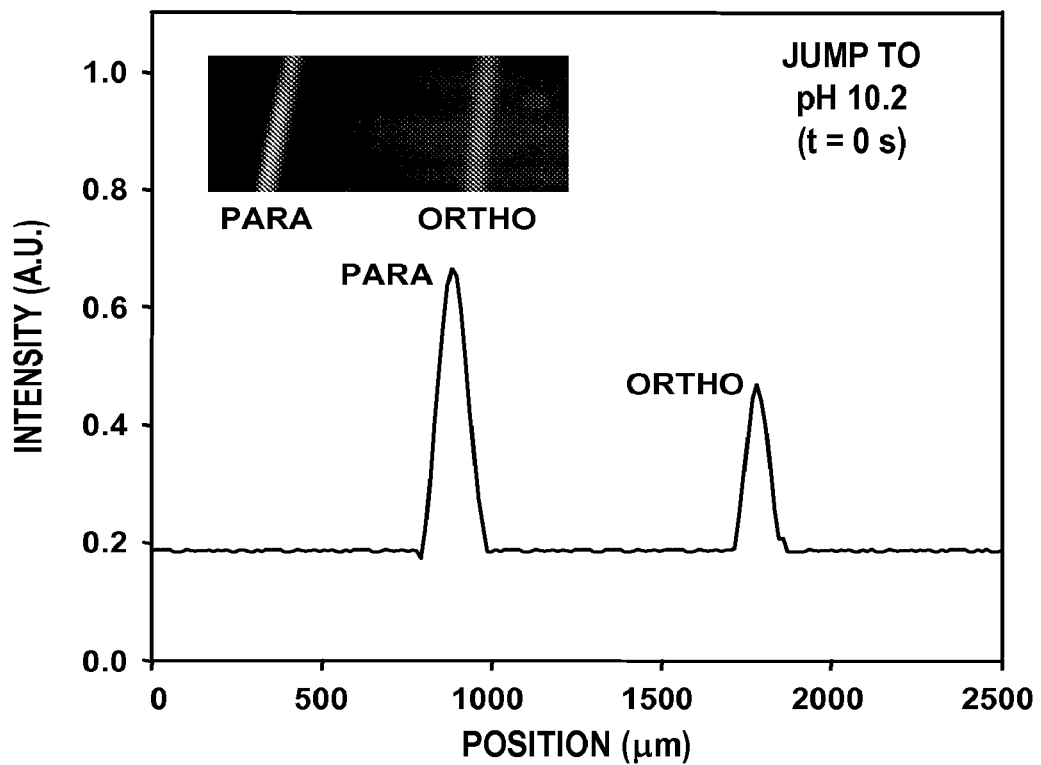
Figure 16C:
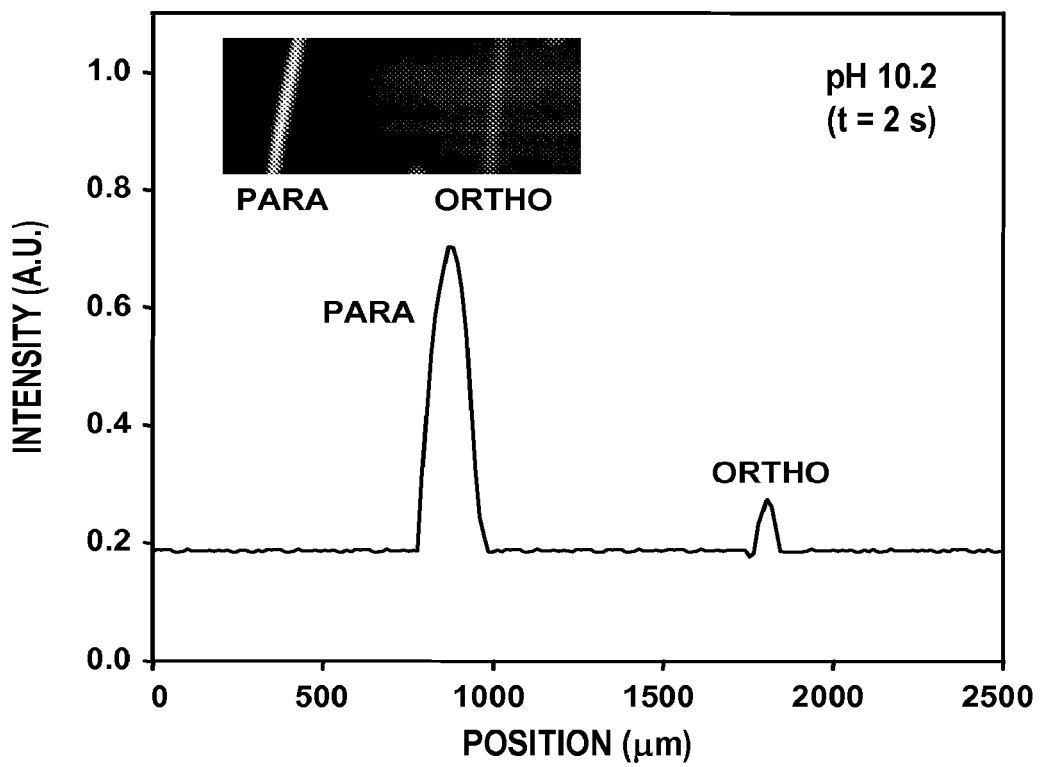
Figure 16D:
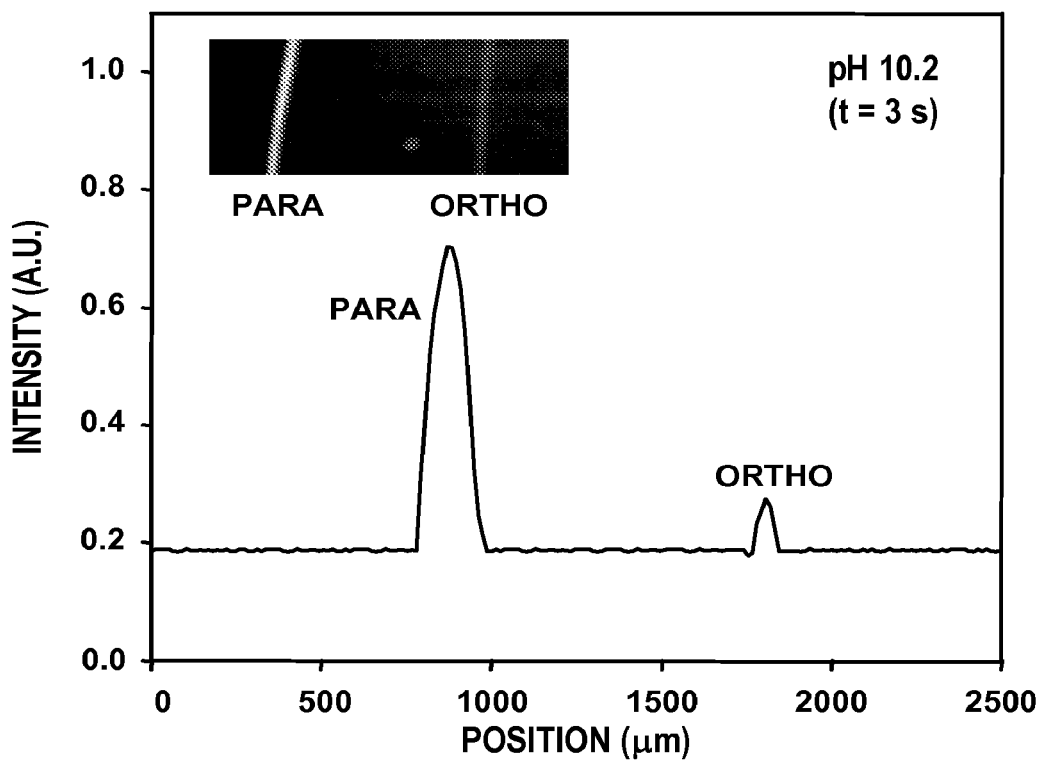

Line profiles taken from the images (blue and red lines in FIG. 18a) are plotted in FIG. 18b. As illustrated, the fluorescence intensity after the introduction of the protein molecules increased and then leveled-off as the protein concentration was increased. The fluorescence intensity from the ortho-Texas Red® DHPE was enhanced after protein binding by 1.4 times at the highest two bulk protein concentrations. Based on the curve in FIG. 15b, the initial fluorescence intensity was 42% of the maximum value and ended at 60% of the maximum value upon protein binding. This interfacial pH shift occurred in the regime where the fluorescence intensity varied nearly linearly with pH (FIG. 15b).

Figure 18C:
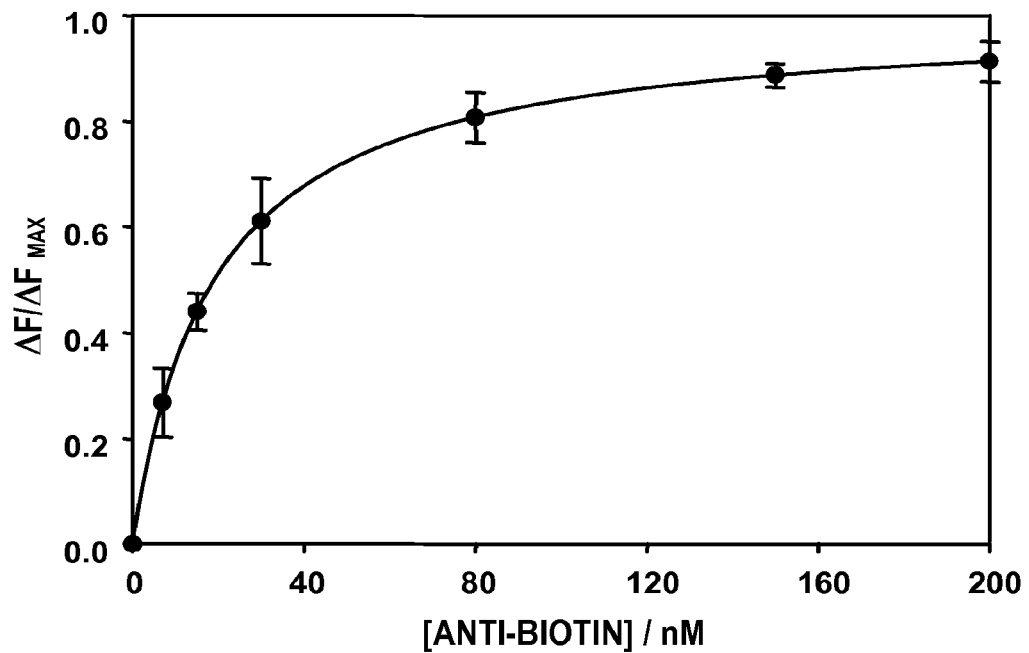
FIG. 18. Epifluorescence images of a bilayer coated microfluidic device before (A1) and after (A2) the introduction of unlabeled anti-biotin antibodies. The concentration of protein in the bulk solution was increased from left to right. The blue and red lines represent the regions used to obtain the line profiles shown in (b). (c) A plot of normalized fluorescence intensity ($\Delta F/\Delta F_{max}$) vs. bulk protein concentration. The solid line represents the best fit to a Langmuir isotherm. (d) Experimental line profiles for the same conditions shown in (b), but with para-Texas Red® DHPE in the membrane instead of ortho. (e) Experimental line profiles for the same conditions shown in (b), but with anti-DNP antibodies. (f) Experimental line profiles for the same conditions as in (b), but in the absence of biotin-cap-PE. A 4× air objective was used to make all measurements. It should be noted that each data point in (c) represents the average of three measurements and the error bars are standard deviations from those measurements.

The normalized increase in fluorescence intensity as a function of bulk antibody concentration from FIG. 18b is plotted as a function of bulk protein concentration in FIG. 18c. Specifically, the y-axis plots the change in fluorescence intensity ($\Delta F$) relative to the maximum change in fluorescence intensity when a saturation concentration of protein is present ($\Delta F_{max}$). In order to extract the apparent equilibrium dissociation constant ($K_D$), the biotin/anti-biotin binding curves were fit to a simple Langmuir isotherm binding model (eq 1):

$$\Delta F = \Delta F_{max} \times \frac{[P]}{K_D + [P]} \quad (1)$$

where [P] is the bulk antibody concentration. The fit to the curve for the data in FIG. 18c yields $K_D$=24±5 nM.

Figure 18D:
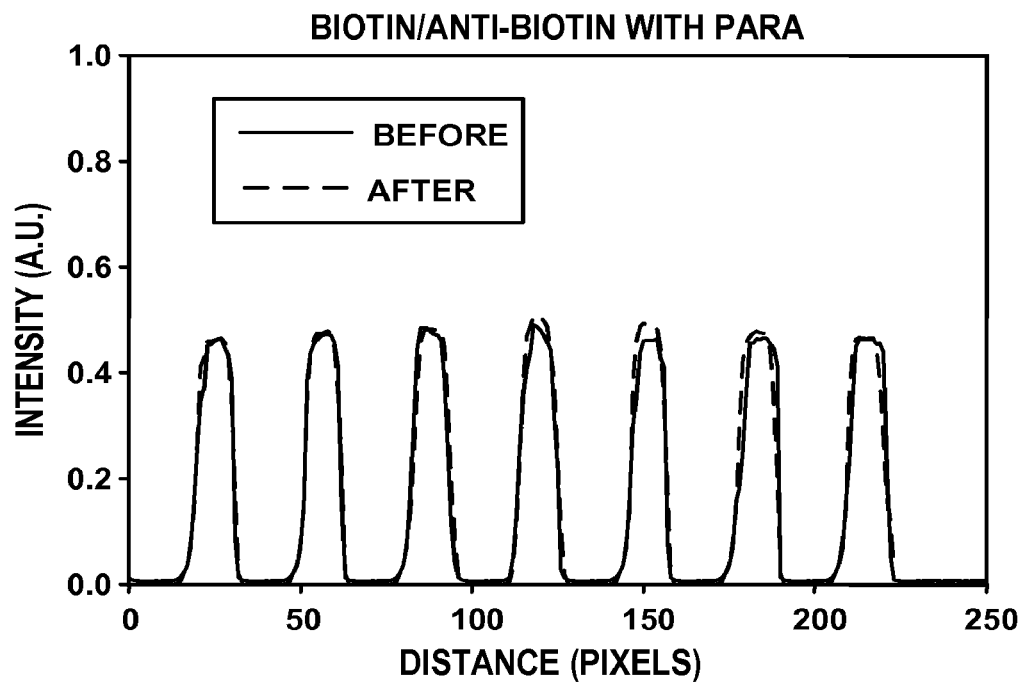
Figure 18E:
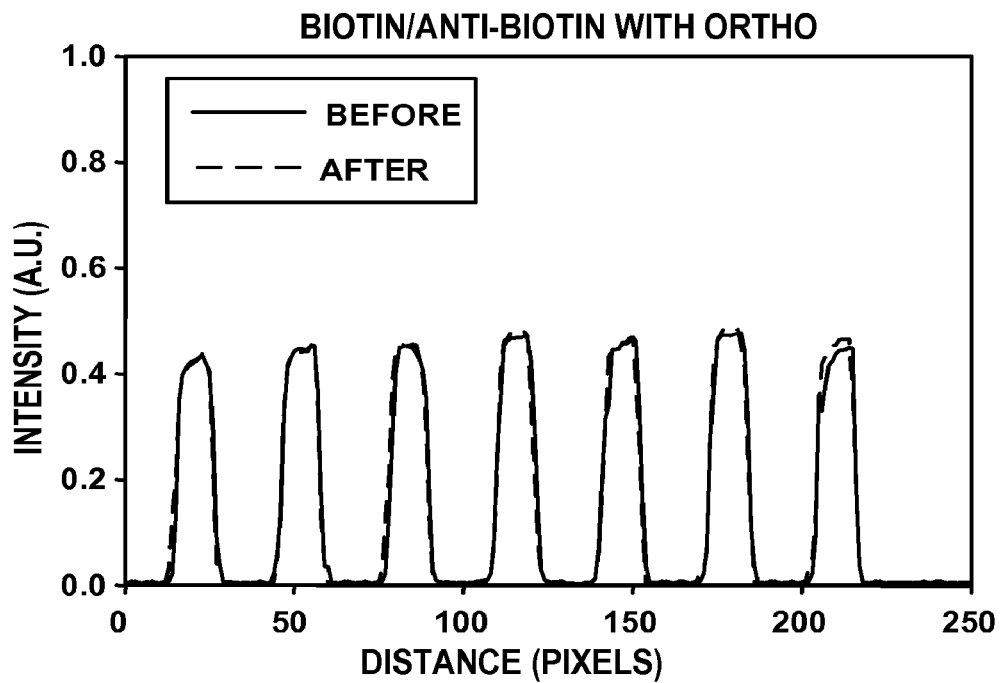
Figure 18F:
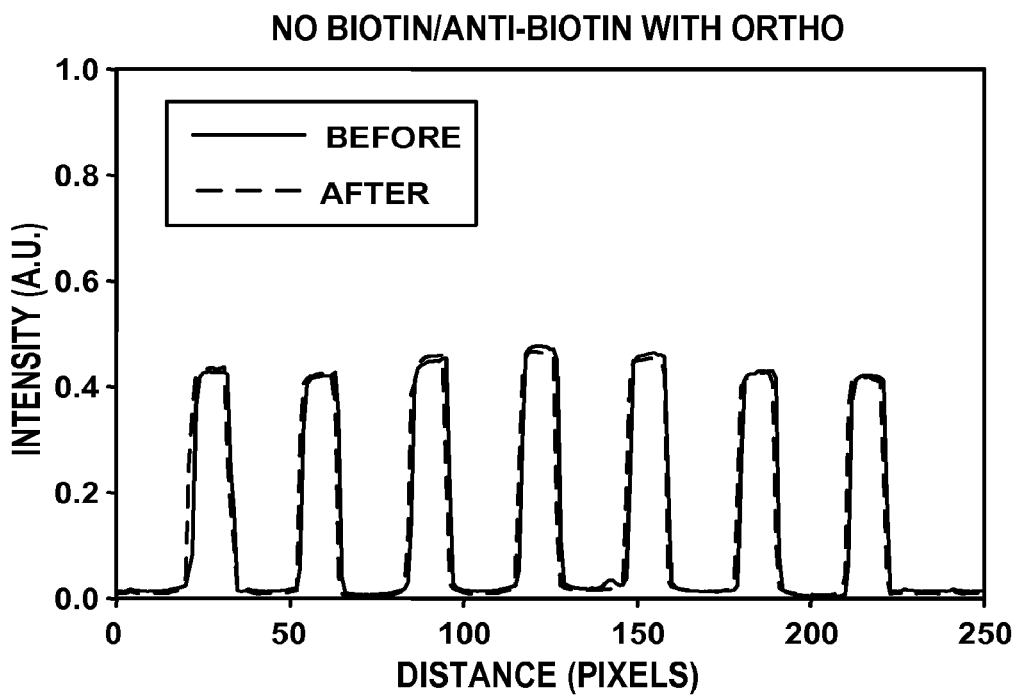

The biotin/anti-biotin binding experiments were repeated under a nearly identical set of conditions, but using para-Texas Red® DHPE instead of ortho. The fluorescence line profiles both before and after antibody binding are shown in FIG. 18d. As illustrated, little if any change in fluorescence intensity occurred under these conditions. Several additional control experiments were also performed. For example, anti-DNP antibodies, which are not specific for biotin, were used instead of the anti-biotin antibodies. Also, experiments were performed with anti-biotin antibodies and ortho-Texas Red® DHPE, but without any biotin-cap-PE in the membrane. In both of these cases, the fluorescence intensities from the microchannels remained unchanged within experimental error upon the introduction of protein (FIGS. 18e & 6f, respectively). Such results are consistent with both high ligand-receptor specificity as well as relatively low levels of non-specific protein adsorption to the surface.

Similar experiments using biotin and anti-biotin were performed but using 1 mol % ortho-Texas Red® DHPE instead of 0.03% and 1.0 mol % biotin-PE instead of 0.5%. Results are shown in FIGS. 28, 29A, 29B, and 30. Using 0.03 mol % as discussed above, detection limits of around 8 pM were detected for biotin/anti-biotin in imaging mode and 350 fM for that same interaction in non-imaging mode. These numbers correspond, in imaging mode, to about 1 part in 3,000 of $K_D$ and in non-imaging mode, this is about 1 part in 70,000. Under conditions using 1 mol % ortho-Texas Red® DHPE and 1.0 mol % biotin-PE, the detection limit was at least 1 part in 3,000,000, and possibly as low as 1 part in 30,000,000. These results demonstrate that increased sensitivity is obtained using higher ortho-Texas Red® DHPE concentrations. Without being bound by theory, it is believed that because the Debye length is shortened (~1 nm) under the conditions of the experiment, the sensitivity is enhanced.

Figure 19:
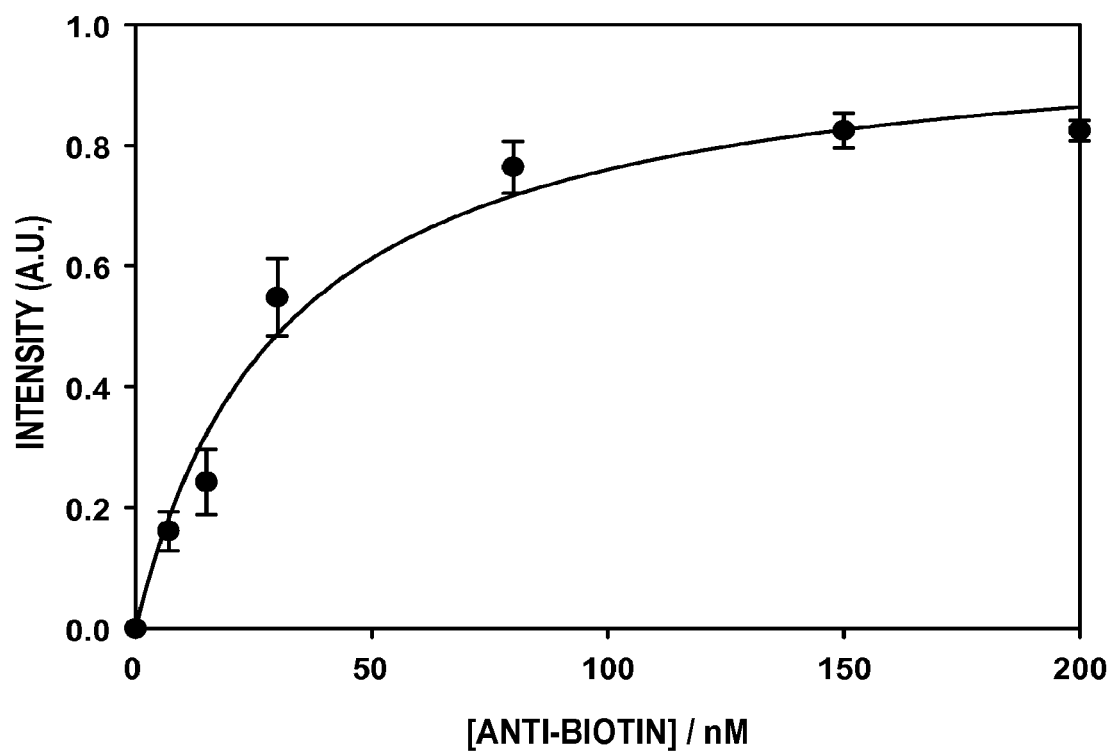
FIG. 19. Plot of TIRFM intensity vs. bulk protein concentration for the labeled anti-biotin/biotin binding system. Each data point represents the average of three measurements and the error bars are standard deviations from those measurements. The solid curve through the data is the best fit to a Langmuir isotherm.

Next, classical antibody binding experiments were performed using anti-biotin antibodies labeled with Alexa Fluor®-594 dye (FIG. 19). Binding measurements were made by total internal reflection fluorescence microscopy (TIRFM) (Axelrod, D., et al., Annu. Rev. Biophys. Bio. 13:247-268, 1984) as described previously (Jung, H. S., et al., Biophys. J. 94:3094-3103, 2008). In this case the supported membranes contained 99.5 mol % POPC and 0.5 mol % biotin-cap-PE. These experiments yielded a $K_D$ value of 32±7 nM. Therefore, the classical label and pH modulation assays gave nearly identical results within experimental error. Moreover, both values correlated well with previously reported values for biotin/anti-biotin interactions on supported membranes (Blake, R. C., et al., Anal. Biochem. 272:123-134, 1999).

The similarities between the classical and pH modulation measurements as well as the associated control experiments are strong evidence for the reliability of the new assay. Specifically, the change of fluorescence intensity in the pH modulation assay appears to correlate linearly with the interfacial antibody concentration under the conditions of these measurements. Moreover, this assay may be far easier to perform than its protein labeled counterpart. In fact, the classical binding assay requires that the antibodies be conjugated with fluorescent dye molecules and that free dye be subsequently separated from the labeled antibodies by running the mixture down a size exclusion column. Once the labeled antibodies are introduced into the microchannels, the fluorescence assay must discriminate between antibodies bound to the surface and those in the bulk solution above it. As noted above, this was done in the present case by TIRFM, a surface specific technique that requires a laser beam to be introduced to the sample past the angle of total internal refection (Yang, T., et al., J. Am. Chem. Soc. 125:4779-4784, 2003). By contrast, a pH modulation assay according to some embodiments may be run in standard epifluorescence mode because the pH sensitive dye molecules are already located at the interface within the supported bilayer. Of course, no modification of the antibodies is needed to do these experiments.

Limit of Detection (LOD) Measurements. The LOD value for this pH sensor assay was determined by two different metrics. First, the CCD camera was used in imaging mode to determine the fewest number of IgG molecules that could be sensed. In that case 4×4 pixel binning was employed, which corresponds to a 1.7 μm² area at the lipid bilayer interface. Second, the experiments were repeated with 200×200 pixel binning to determine the lowest number density of IgG molecules that could be detected. The camera contains a 1024×1024 pixel array.

Figure 20A:
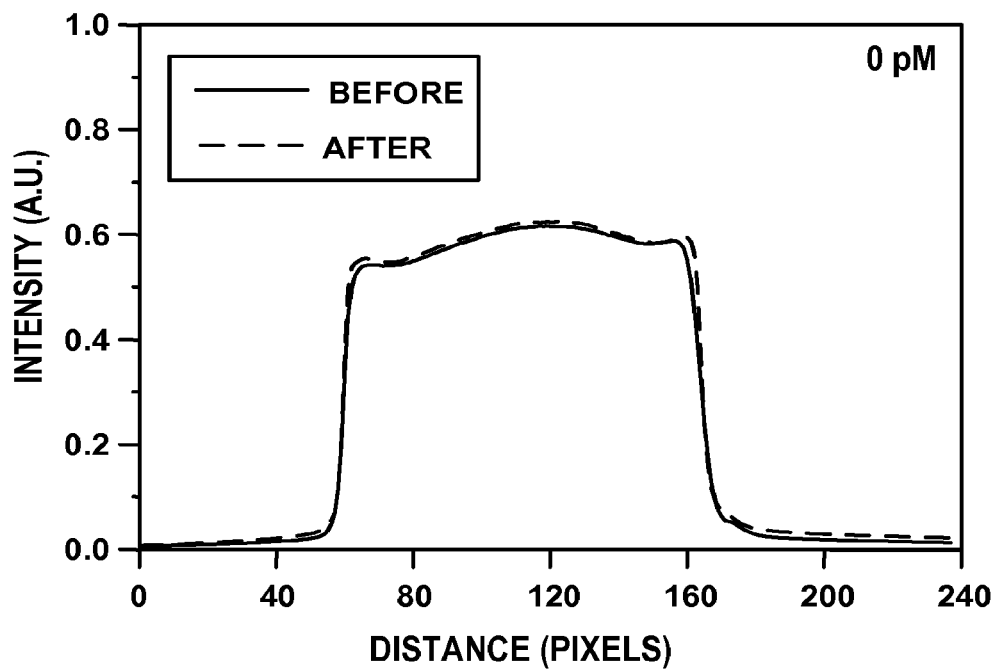
FIG. 20. LOD results for 4×4 pixel binning. (a)-(e) Intensity line profiles across single microfluidic channels as various concentrations of anti-biotin antibodies were introduced to the bulk solution. The experiments were conducted at a bulk pH of 7.8 in 10 mM PBS with 150 mM NaCl. (f) A plot of the change in the fluorescence intensity of the ortho-Texas Red® DHPE, $\Delta F(\%)$, vs. bulk protein concentration (red circles). The slope of the line and its corresponding $R^2$ value are provided in the figure. A control experiment was also performed with para-Texas Red® DHPE in the membrane under otherwise identical conditions (black circles).
Figure 20B:
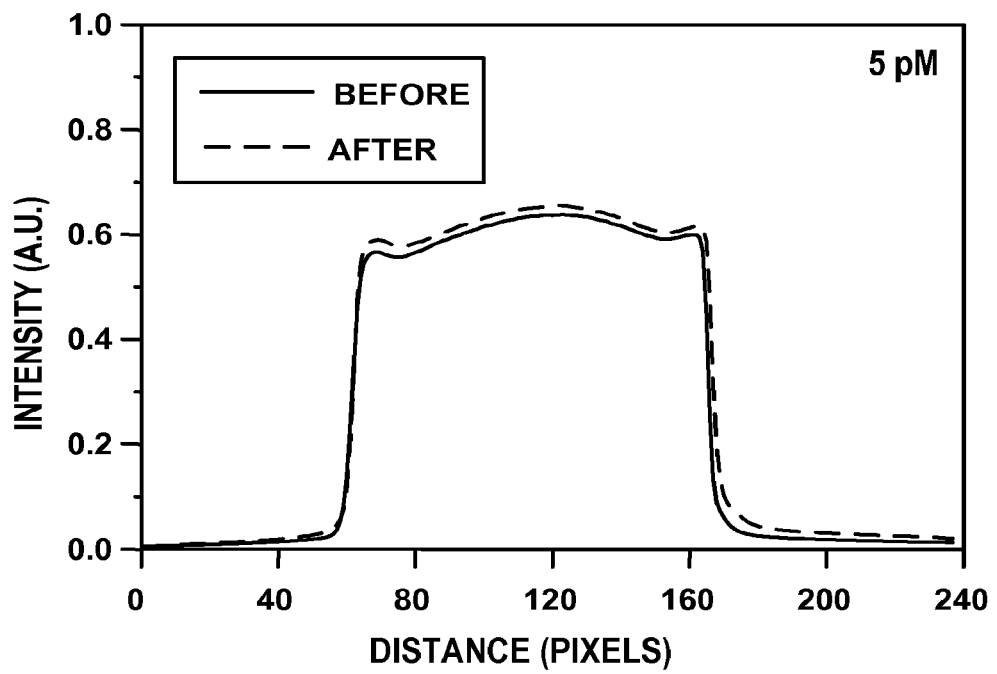
Figure 20C:
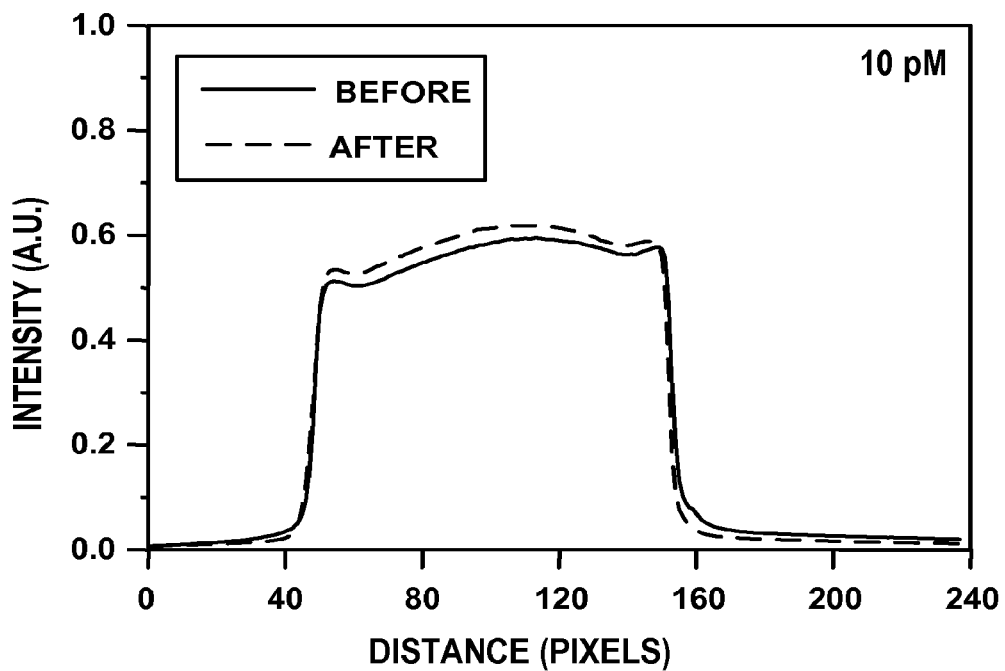
Figure 20D:
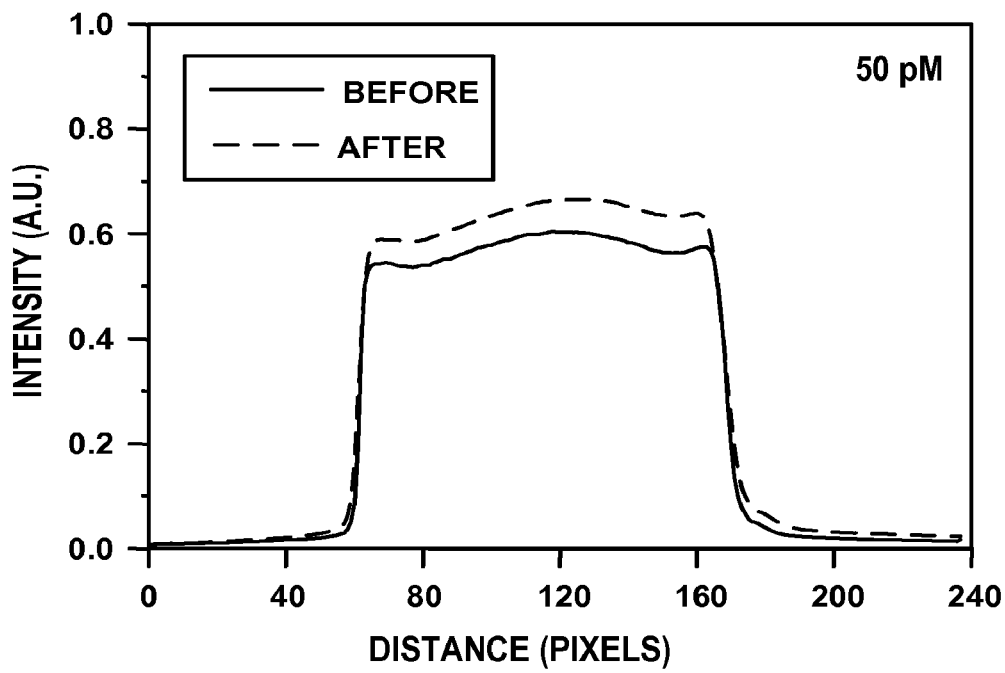
Figure 20E:
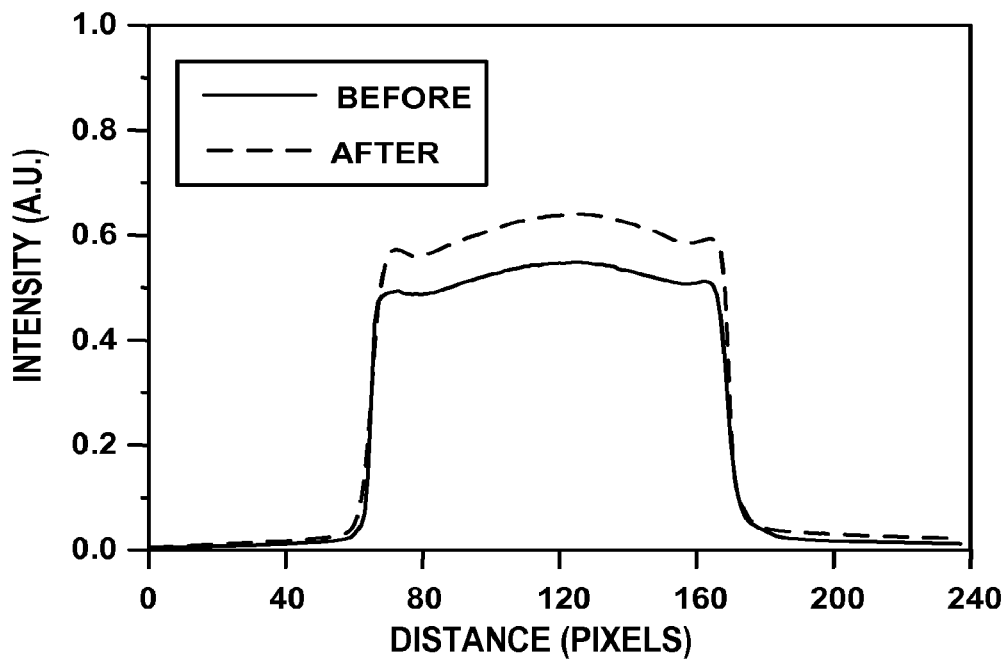
Figure 20F:
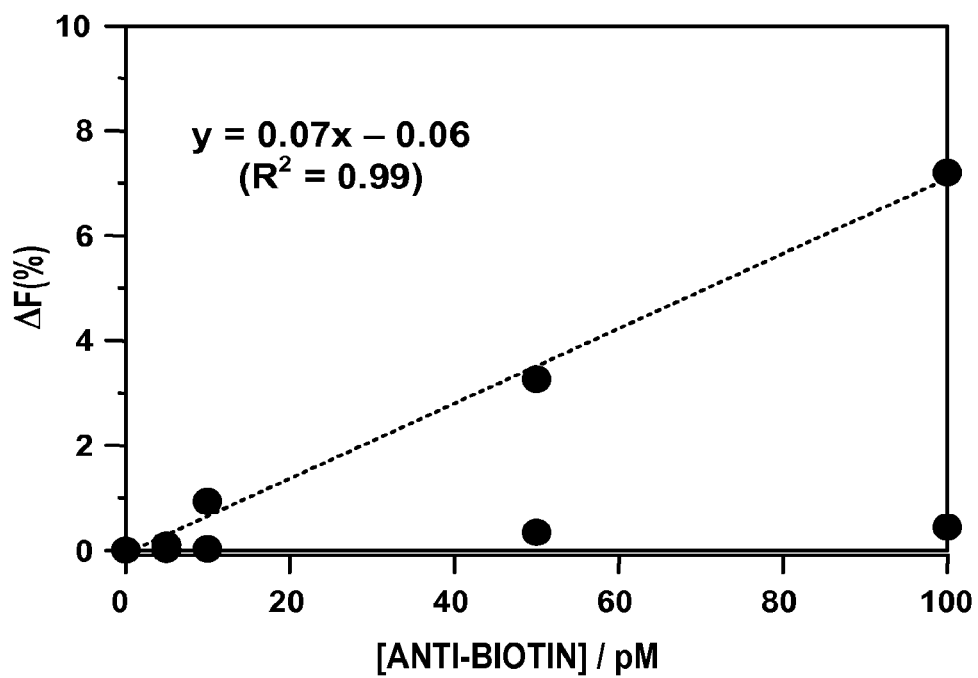

To perform 4×4 binning experiments, supported bilayers were made from POPC lipids doped with 0.5 mol % biotin-cap-PE and ~0.03 mol % ortho-Texas Red® DHPE. Concentrations of anti-biotin IgG ranging from 0 to 100 pM were introduced into the bulk solution. Line profiles both before and after the introduction of the protein are shown in FIG. 20. As illustrated, the fluorescence intensity remained essentially unchanged when 0 pM anti-biotin was added (pure PBS buffer flowed for 60 min), but changed by ~8% when 100 pM anti-biotin was added. Intensity changes were linear with concentration between 0 and 100 pM antibody as shown in FIG. 20f (red circles). The slope of the line and its corresponding $R^2$ value is provided as an inset in the figure.

Error analysis of the intensity profiles revealed that the averaged fluorescence intensity over a given channel was stable to within ±0.2% over a 1 h time period. This gives an LOD value of ~8 pM if the limit of detection is defined as 2.58 times the experimental error. This definition of LOD was chosen because it represents the 99% confidence limit for these measurements (Christian, G. D. Analytical Chemistry; 6th ed.; John Wiley & Sons, Inc., 2004). Control experiments with para-Texas Red® DHPE under the same conditions showed that little if any change in fluorescence intensity occurred when the antibody was introduced (FIG. 20f, black circles). Additional control experiments were performed with anti-DNP as well as without any biotin-cap-PE in the membrane (data not shown). No observable change in fluorescence intensity occurred.

Figure 21A:
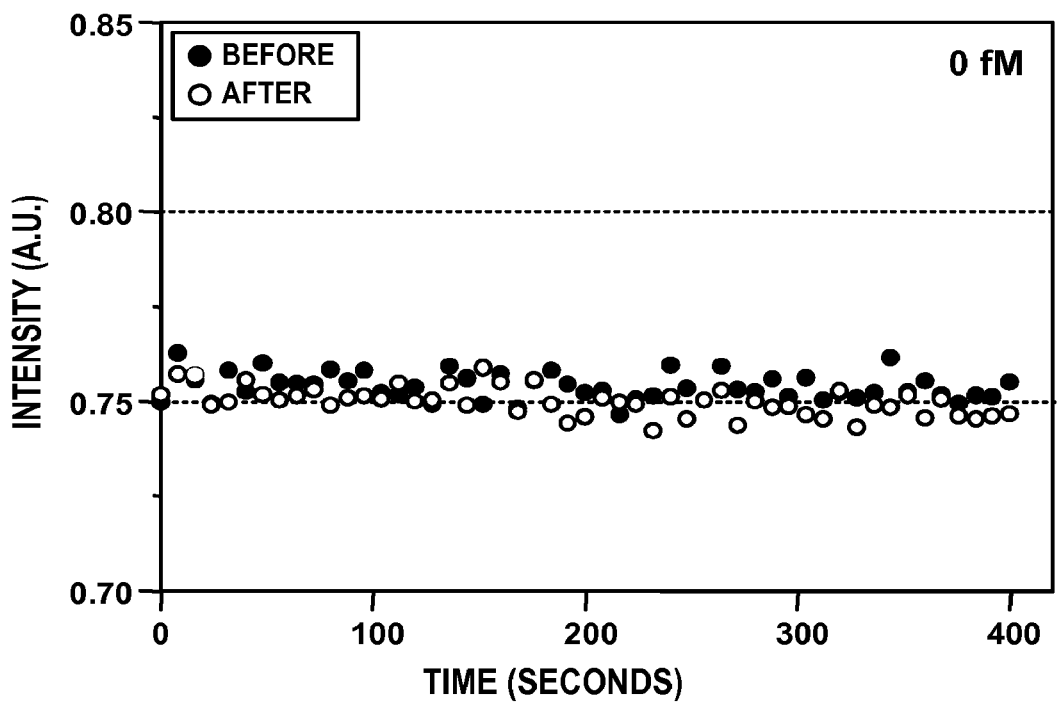
FIG. 21. LOD results for 200×200 binned pixel regions. (a)-(e) Single point fluorescent intensity measurements as a function of time both before and after the introduction of various concentrations of anti-biotin. (f) A plot of fluorescence intensity for ortho-Texas Red® DHPE, $\Delta F(\%)$, vs. bulk protein concentration (red circles). The slope of the line and its corresponding $R^2$ value are provided in the figure.
Figure 21B:
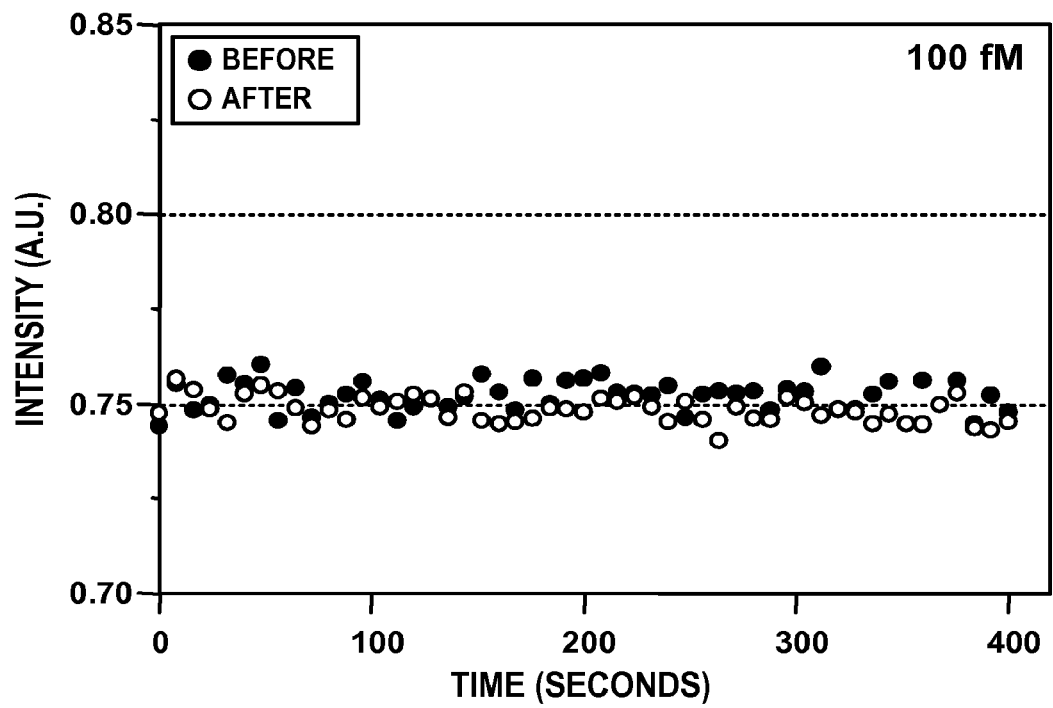
Figure 21C:
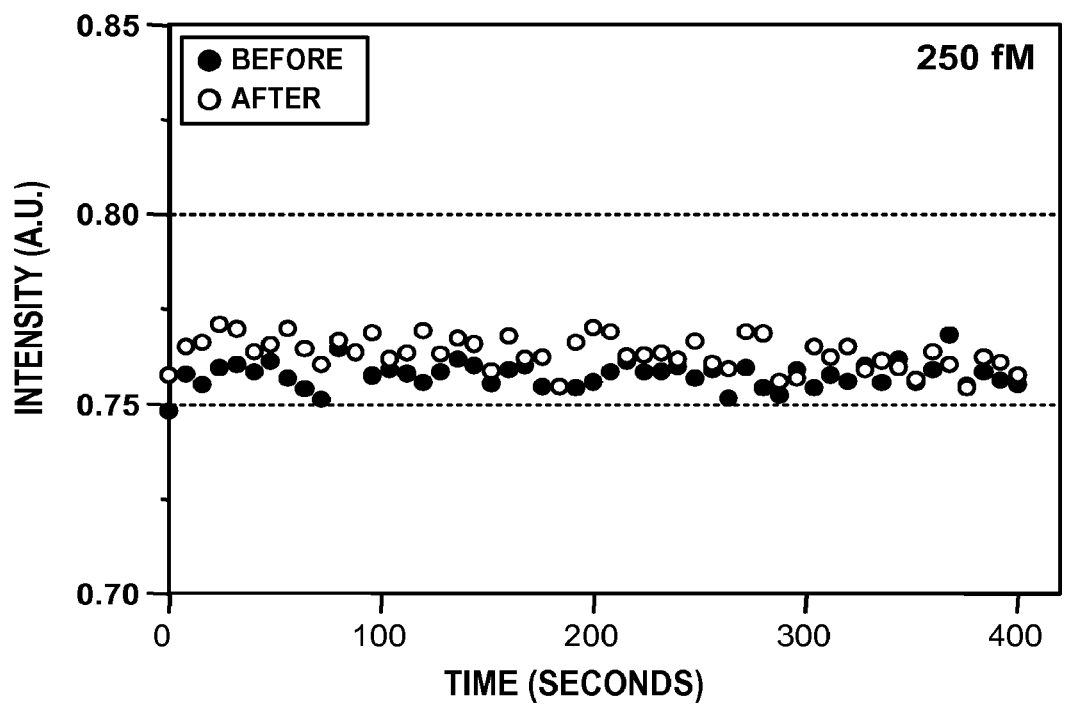
Figure 21D:
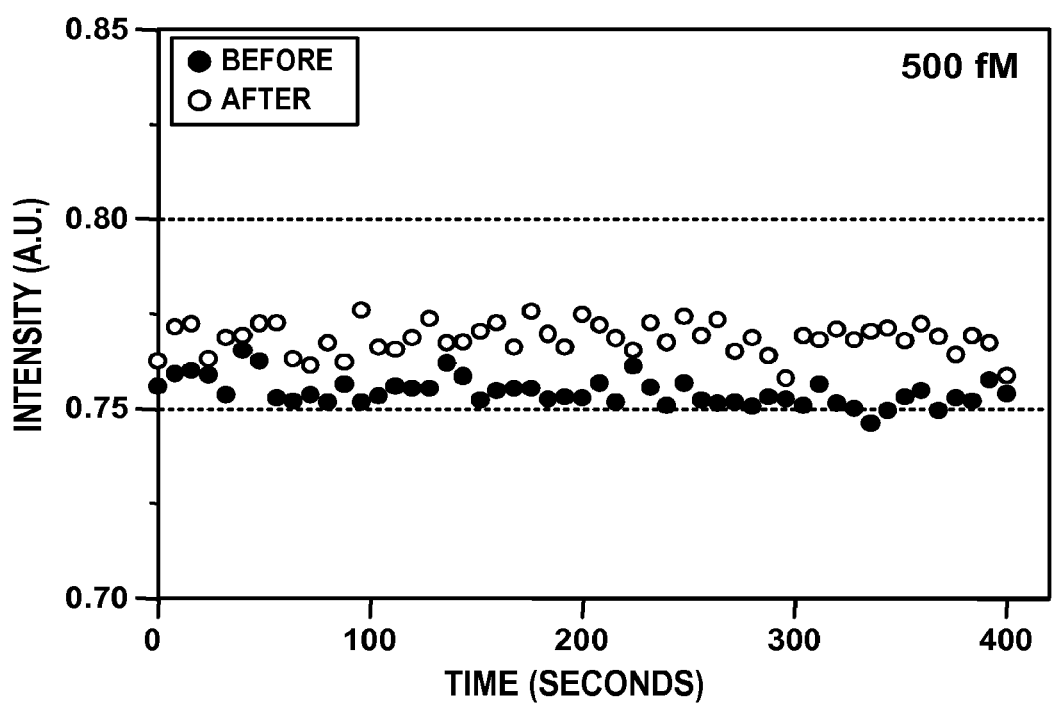
Figure 21E:
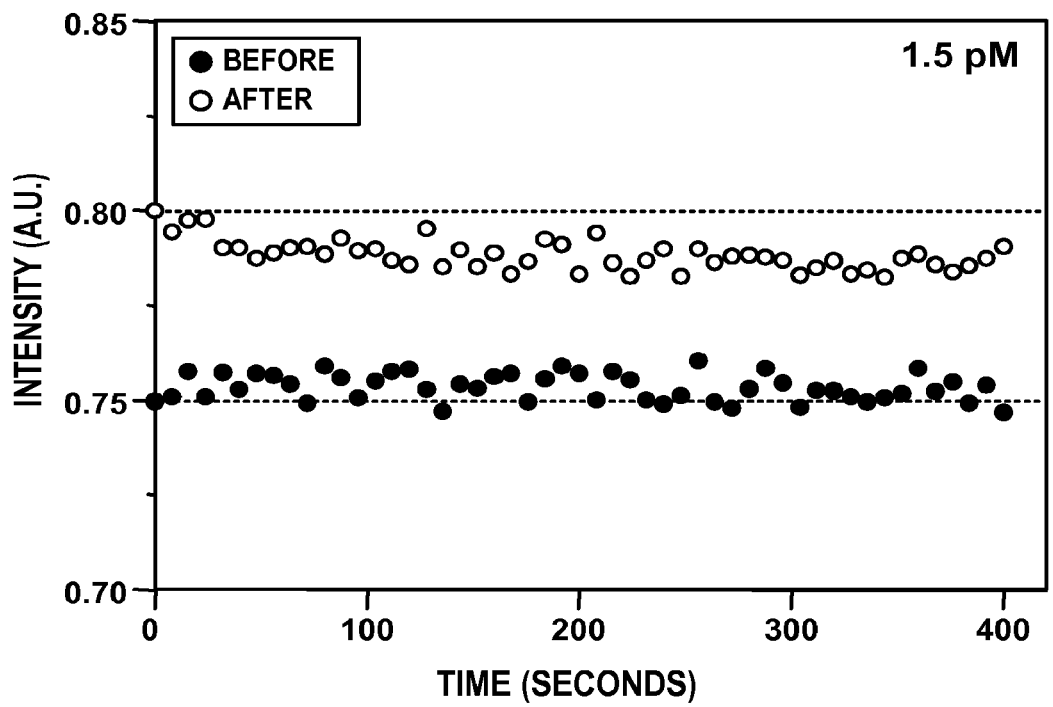
Figure 21F:
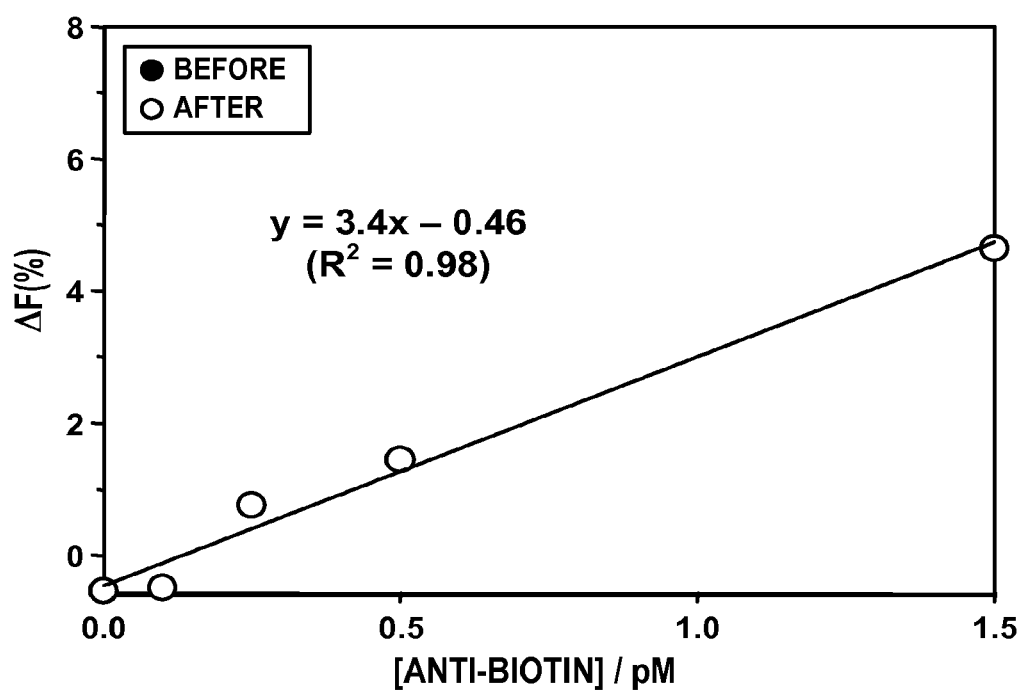
Figure 23A:
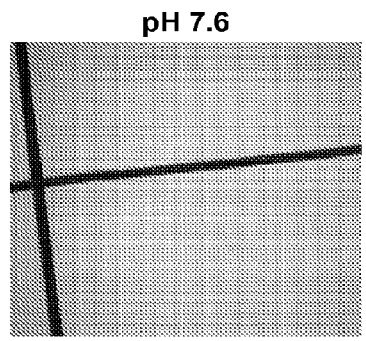
FIG. 23. Fluorescence images of an SLB on a borosilicate substrate composed of 99.47 mol % POPC/0.5 mol % biotin-cap-PE/~0.03 mol % para-Texas Red® DHPE.
Figure 23B:
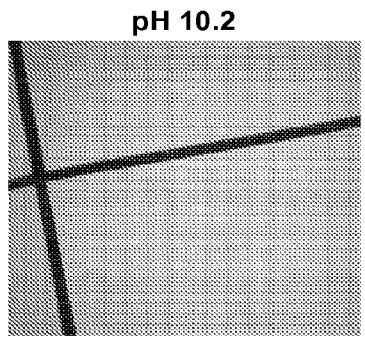
Figure 23C:
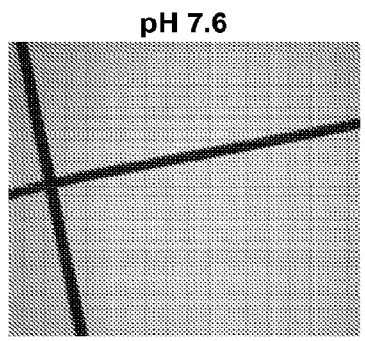
Figure 23D:
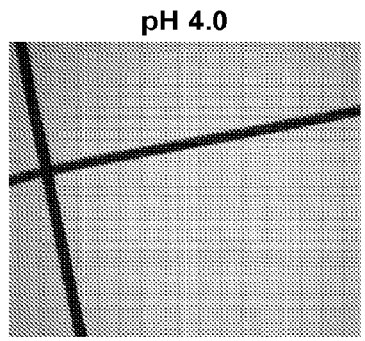
Figure 23E:
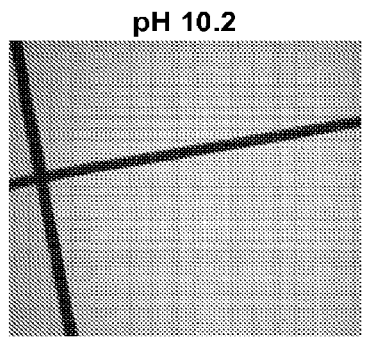
Figure 23F:
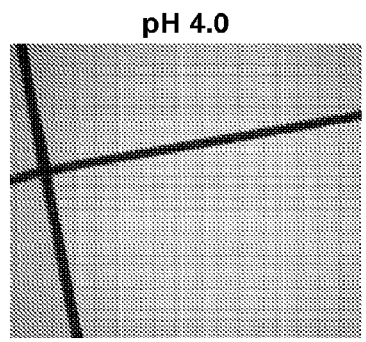
Figure 23G:
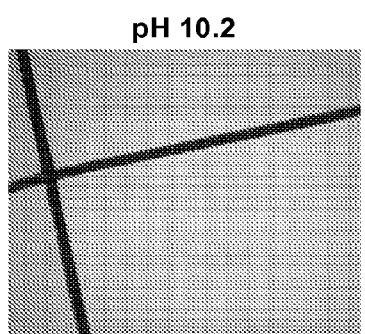

Next, the LOD was determined using 200×200 pixel binning. This dimension, which represents a 65 μm×65 μm region of the liquid/solid interface, was chosen because it corresponds well to the width of an individual microfluidic channel. The experimental conditions were identical to those used above. Concentrations of anti-biotin ranging from 0 to 1.5 pM were introduced into the bulk solution. In this case, single data point intensities were recorded as a function of time (FIGS. 21a to 9e). Approximately 50 data points were obtained for each sample region over the course of 400 sec both before and after the introduction of protein. This was done to improve the signal-to-noise of the experiment. As illustrated, the fluorescence intensity remained stable to within ±0.3%. The data at each antibody concentration were averaged and plotted in FIG. 21f (red circles). The LOD value was found to be ~350 fM at the 99% confidence limit.

The present disclosure relates, according to some embodiments, to a pH sensitive assay for monitoring ligand/receptor binding at lipid membrane interfaces. In some embodiments, a method may be quite general since most biomacromolecules in solution bear a net charge. In some specific example embodiments, a shift of ~0.35 pH units occurred upon saturation binding of IgG to a lipid membrane with 0.5 mol % lipid-conjugated haptens compared to the case of no bound proteins. Such a result is in agreement with the notion that increasing the density of negative charge at the interface recruits counterions (especially hydronium ions). In fact, Fromherz has suggested that changes in membrane potential may affect the interfacial concentration of hydronium ions and thereby shift the local pH (Fromherz, P. *Method. Enzymol.* 171:376-387, 1989). Also, Latour and co-workers demonstrated that deprotonated COOH-terminated self-assembled monolayers (SAMs) attract hydronium ions to the interface, thus resulting in a decrease of the local pH value (Fears, K. P., et al., *Langmuir* 24:837-843, 2008). Changes in interfacial charge density, therefore, may lead to corresponding shifts in the apparent $pK_A$ values of titratable surface groups relative to their values in bulk solution (Zuidam, N. J. and Y. Barenholz, *Biochim. Biophys. Acta* 1329:211-222, 1997). This makes the titration of fluorescent dye molecules useful for sensor development. How useful this phenomenon can be for assay development may ultimately depend upon its sensitivity.

Sensitivity limits for biosensor platforms are often reported in the literature in terms of the minimum bulk analyte concentration that can be detected (Liang, M., et al., *Assay Drug Dev. Techn.* 5:655-662, 2007). However, the LOD is usually strongly correlated to the strength of a given ligand/receptor binding event. For example, a typical antibody/antigen interaction may have a $K_D$ value of 25 nM, while a tighter protein/ligand interaction could be $K_D$=~1 pM. A heterogeneous detection assay (i.e. detection of the analyte by binding to a surface from solution) may have a detection limit of 250 pM for the former, but 10 fM for the latter. In reality, these apparently different bulk detection limit values may actually represent similar number densities of proteins at the interface because each LOD value would be 1% of $K_D$. Therefore, the number of proteins at the interface which can be detected may represent a more intrinsic measure of the LOD value for a particular assay platform.

In the studies described in FIG. 20, 0.5 mol % biotin-cap-PE was employed and used 4×4 pixel binning of a CCD camera with a 40× oil immersion objective for detection. This corresponds to a 1.7 μm² surface area at the liquid/solid interface for each binned pixel region. The area per lipid molecule in the membrane is known to be ~0.7 nm²/lipid (White, S. H. and G. I. King, *Proc. Nat. Acad. Sci. U.S.A.* 82:6532-6536, 1985). By assuming that biotin-cap-PE is roughly the same size as the lipids, 0.5 mol % of this molecule translates to ~7×10³ ligands/μm² on the upper bilayer leaflet. The intensity change at 500 nM IgG is ~150 times greater than that observed at the LOD (~8 pM). Therefore, the number density of proteins at the interface may be ~150 times less than the saturated value. This results in a detection limit of ~380 IgG molecules if one assumes a 2:1 binding ratio between the antibody and the antigen (Yang, T., et al., *J. Am. Chem. Soc.* 125:4779-4784, 2003). Such a non-optimized result is within a few orders of magnitude of single molecule measurements. This result corresponds to a surface density of 56 pg/mm². This surface density LOD value may be substantially improved by binning together a larger number of pixels while making the binding measurements. Although one loses the ability to obtain a surface image, the signal to noise ratio may roughly improve with the square root of pixels employed. Additional improvements may be obtained by time averaging. The data for 200×200 pixel binning are provided in FIG. 21. Such data represents an antibody surface density of ~2 pg/mm². Moreover, the 350 fM LOD is a factor of ~69,000 lower than the $K_D$ value of 24 nM, although one is no longer sensing just a few hundred IgG molecules. It may be possible to sense even lower number densities of proteins by binning an even larger number of pixels together. Indeed, simultaneous sensing over a 1 mm² area may reduce the number density detection limit by yet another order of magnitude. In that case, however, the ability to perform multiplex detection is completely eliminated.

Currently, surface plasmon resonance (SPR) is one of the most commonly employed label-free assays for monitoring ligand/protein binding at an interface. Since direct comparisons between assays may sometimes be problematic, this discussion is limited to antibody/antigen binding measurements. In that case, SPR platforms in a Kretschmann configuration (Kretschmann, E., *Z. Phys.* 241:313-324, 1971) gave rise to an LOD of ~3 pM for a system with a $K_D$ value of ~4 nM (Yang, C. Y., et al., *Lab on a Chip* 5:1017-1023, 2005). For the present assay, a detection limit significantly better than that (~350 fM out of 24 nM) was achieved. Of course, the sensitivity limits for SPR and SPRI may be improved (e.g., vastly improved) by secondary amplification steps (Nam, J. M., et al., *Science* 301:1884-1886, 2003; Fang, S. P., et al., *J. Am. Chem. Soc.* 128:14044-14046, 2006; Goodrich, T. T., et al., *J. Am. Chem. Soc.* 126:4086-4087, 2004). By analogy, LOD from the current pH modulation assay could also be substantially enhanced by subsequent amplification procedures after antibody binding.

The pH modulation platform developed here may be highly versatile. Binding measurements were made on two dimensionally fluid lipid bilayers because these systems are laterally mobile and may allow the same type of multivalent protein binding to take place as occurs in vivo on a cell surface (Kim, J., et al., *Langmuir* 17:7255-7260, 2001). Moreover, supported lipid bilayer platforms are highly resistant to non-specific protein adsorption (Castellana, E. T. and P. S. Cremer, *Surf. Sci. Rep.* 61:429-444, 2006). Nevertheless, this sensing concept could be expanded to any liquid/solid interface that contains substrate-conjugated ligands and pH sensitive fluorophores. It may also be capable of measuring nearly any protein-ligand binding event provided that the incoming macromolecule possesses a net charge and therefore changes the interfacial pH. As another demonstration of the universality of this method, the binding of cholera toxin B to ganglioside $GM_1$ is provided herein.

The present disclosure describes, in some embodiments, a simple detection method based on pH sensitive dyes was developed. For example, ortho-conjugated Texas Red® DHPE may be incorporated in supported phospholipids bilayers as an interfacial pH sensor. Such sensors have inherently excellent limits of detection and are relatively easy to use. Moreover, the method is fully compatible with multiplexed detection. Therefore, it and similar pH-sensitive dyes could potentially be used in high throughput screening applications.

Additional data related to bilayer quality, saturation anti-biotin binding as a function of pH, and binding data for the $GM_1$-cholera toxin B system is provided herein. Specifically, FIG. 22 provides fluorescence images showing the quality of the bilayers. The two scratch marks in the images were made intentionally with a pair of tweezers to provide contrast. The samples were bleached with the 568 nm line from a mixed gas $Ar^+/Kr^+$ laser. The bleach spots were 14 μm in diameter (full width at half maximum) and the dimensions of the images were 290 μm by 230 μm. Both the fluorescence recovery and bilayer uniformity indicate that the bilayers are of good quality.

FIG. 23 demonstrates that the identical supported bilayer as in FIG. 22 looks relatively unchanged down to the diffraction limit after repeatedly cycling the pH.

Figure 3A:
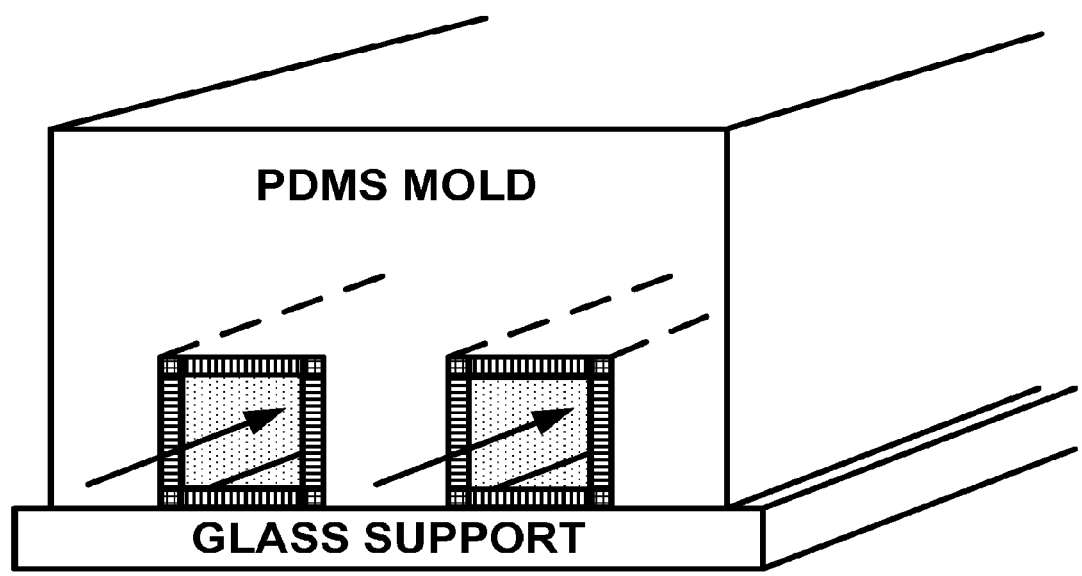
FIG. 3. (left) Schematic diagram of a PDMS/glass microfluidic device. The walls are coated with planar supported bilayers. The arrows represent the direction of solution flow. (right) Epifluorescence image of a working microfluidic device.
Figure 3B:
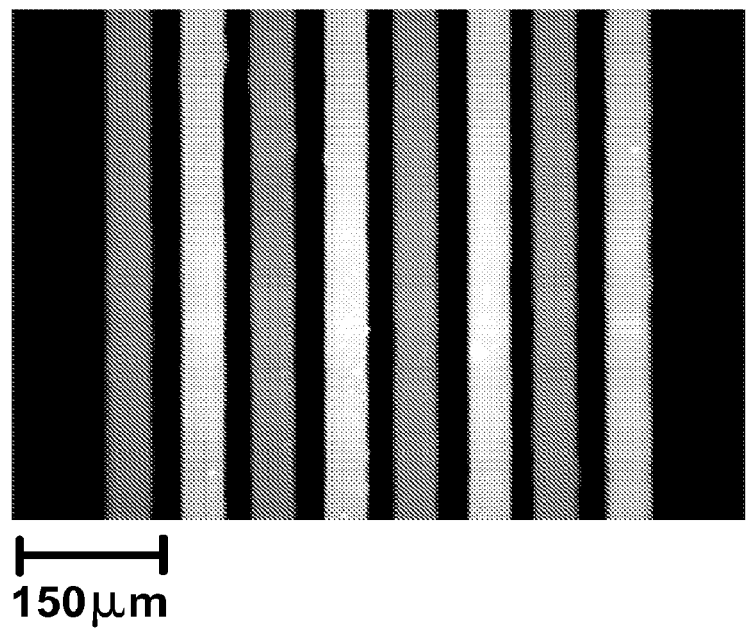
Figure 24A:
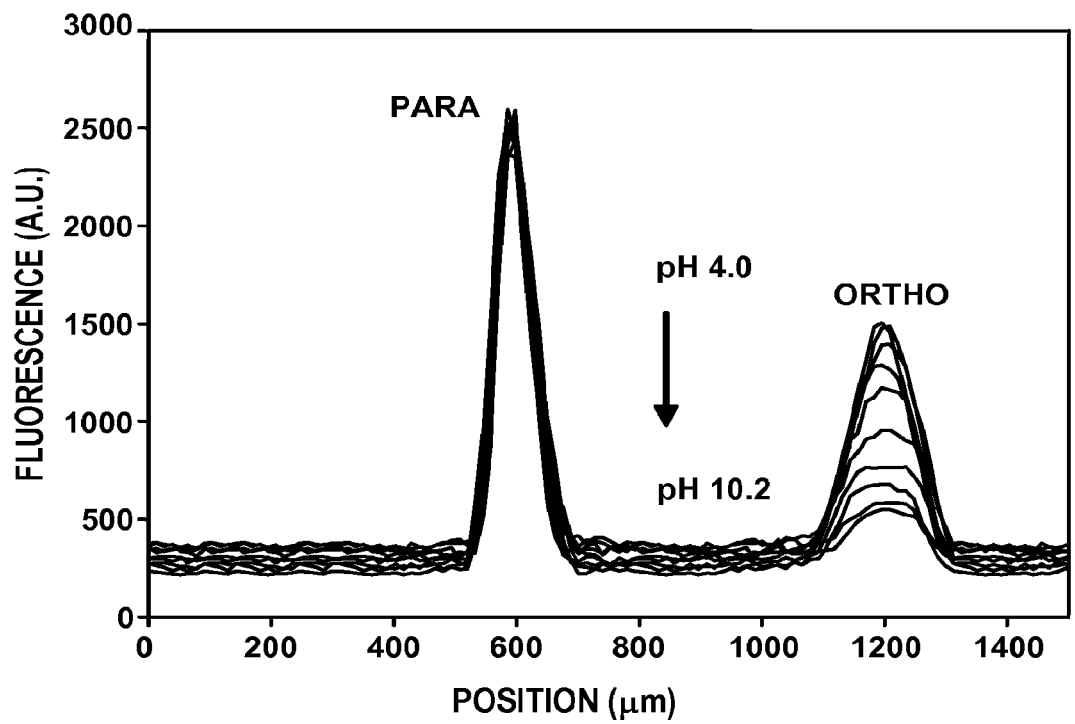
FIG. 24. Fluorescence line scans across the images in (a) FIG. 3a and (b) FIG. 5a. The ratios of the areas under the ortho to ortho peaks were used to obtain the titration curves shown in FIG. 16b and FIG. 18b.
Figure 24B:
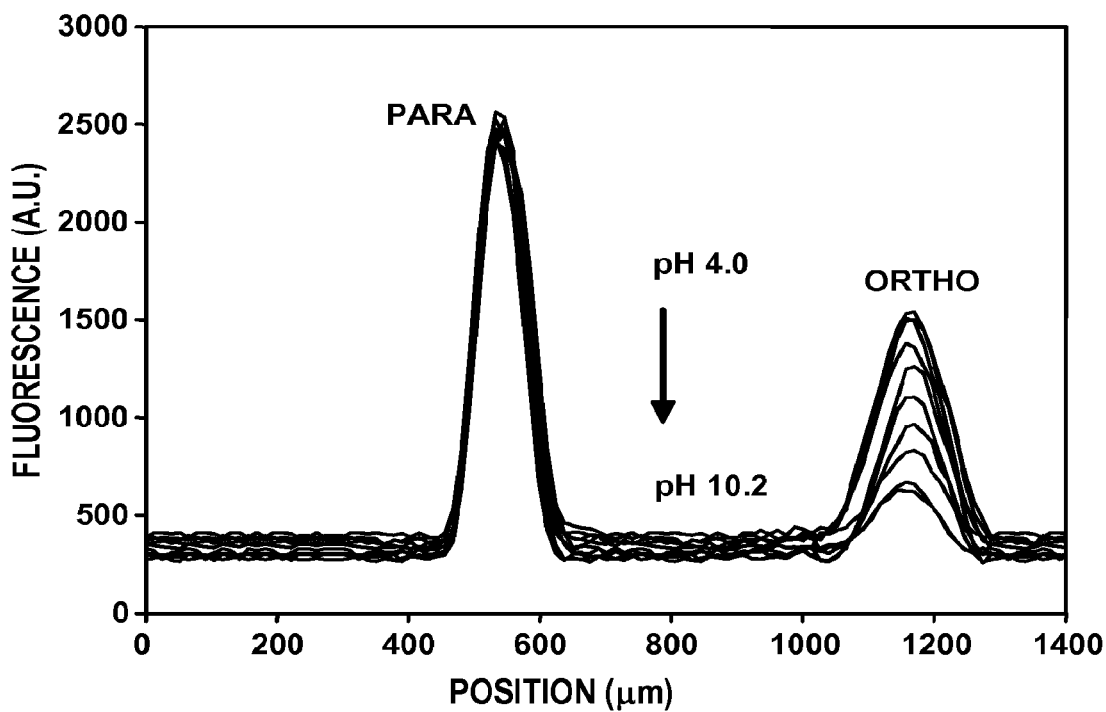

FIG. 24 shows intensity line profile data corresponding to (a) FIG. 3a and (b) FIG. 5a.

Figure 25A:
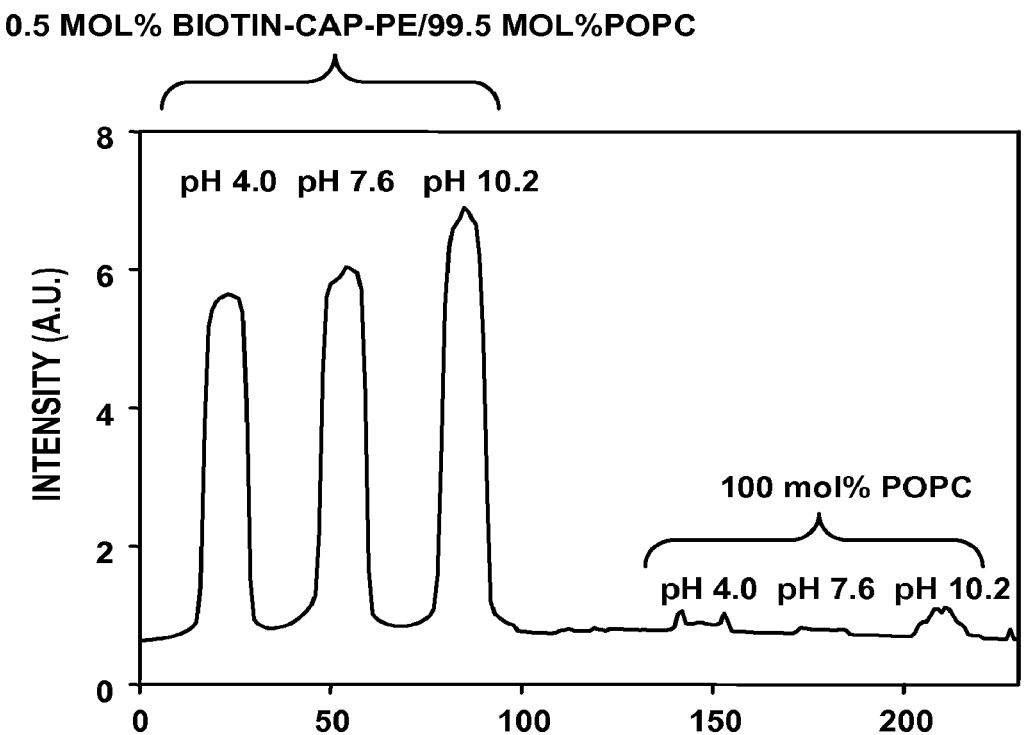
FIG. 25. (a) Fluorescence line scans of the TIRF intensity across a seven-channel microfluidic device coated with POPC bilayers. The three channels on the left contained 0.5 mol % biotin-cap-PE. Alexa Fluor®-594 (pH insensitive dye) (Soper, S. A. et al., Anal. Chem. 70:477 R-494R, 1998) labeled anti-biotin solutions (500 nM) were prepared at pH 4.0, pH 7.6, and pH 10.2, respectively. They were then flowed through the six channels as TIRF measurements were made. The channel in the middle was left empty. (b) Fluorescence intensity for specific binding minus non-specific binding at the three different pH values. The error bars represent standard deviations from three sets of measurements.
Figure 25B:
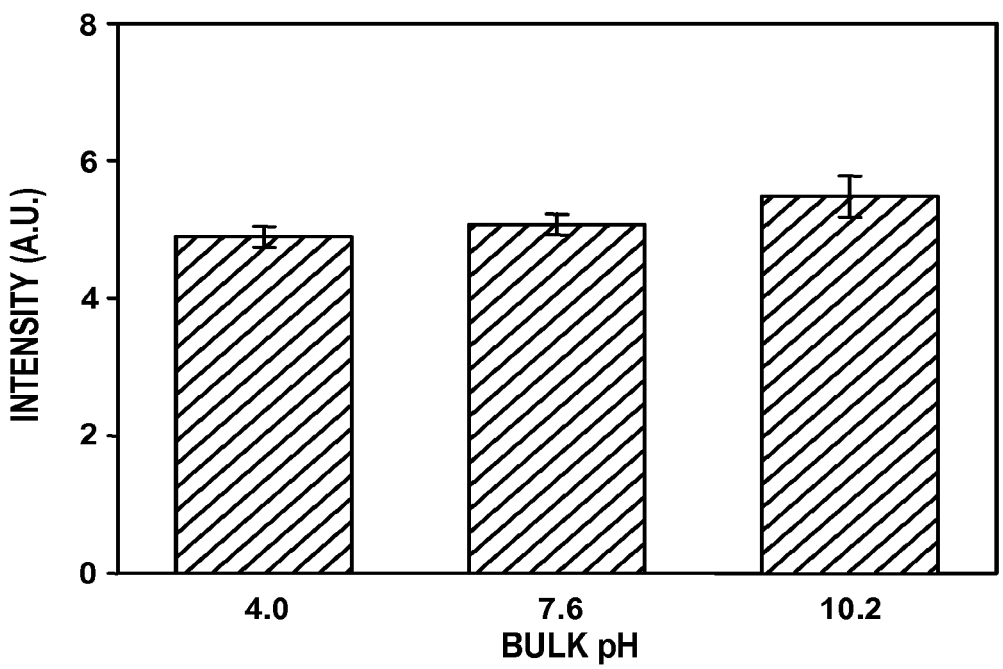

FIG. 25 shows (a) fluorescence intensity line profile data across a seven channel microfluidic device containing POPC bilayers with and without 0.5 mol % biotin-cap-PE at three distinct pH values: pH 4.0, 7.6, and 10.2. The middle channel was left blank. In all six experimental cases, 500 nM of anti-biotin IgG were introduced above the bilayers and the protein was tagged with Alexa Fluor®-594 dye. Fluorescence measurements were made by total internal reflection fluorescence microscopy. As can be seen from the data, the intensity values in both of the channels at pH 10.2 are somewhat higher than at 4.0 or 7.6. Specifically, the channel on the far right shows evidence for a modest amount of non-specific protein adsorption under the most basic set of conditions. (b) The three bars show the peak intensity for specific adsorption at a given pH value minus the peak intensity at the same pH in the absence of biotin in the membrane. Since these values are nearly the same within experimental error, it can be concluded that roughly the same amount of IgG specifically binds to the biotinylated lipids under all conditions. However, there is clearly more non-specific adsorption at pH 10.2. This is an indication that small defects probably form in the supported lipid bilayer under these conditions.

Figure 26C:
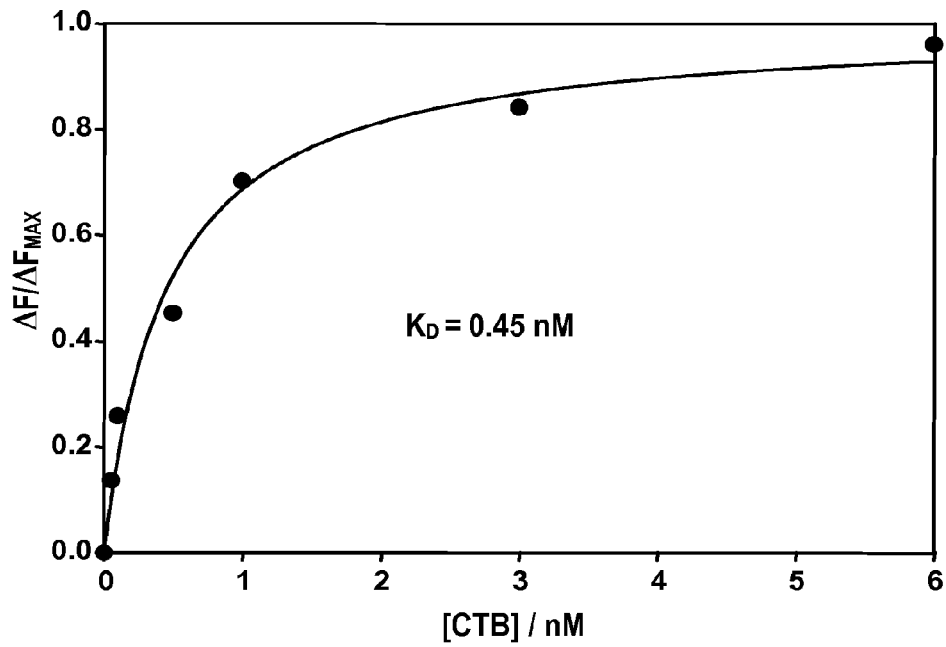
FIG. 26. Binding constant measurements for cholera toxin B to $GM_1$ in POPC/ortho-Texas Red® DHPE membranes. The experimental conditions were identical to those for the biotin/anti-biotin binding pair, but contained 0.5 mol % $GM_1$ instead of biotin-cap-PE. Moreover, the measurements were made at a bulk pH value of 8.2 (a) Epifluorescence images of the seven channel device before and after the introduction of the toxin. (b) Fluorescence line profiles from (a). (c) Fluorescence changes vs. bulk protein concentration. The binding curve was fit to a simple Langmuir isotherm as shown in Eq. 1 of the main text. The abstracted dissociation constant was $K_D$=0.45 nM. This value is in excellent agreement with literature data obtained by fluorescently tagging cholera toxin B. (Kim, S. R. and N. L. Abbott, Adv. Mater. 13:1445-1449, 2001.)

FIG. 26 shows the binding of cholera toxin B to POPC bilayers containing 0.5 mol % $GM_1$ and ~0.03 mol % ortho-Texas Red® DHPE. The measurements were made in a seven channel microfluidic device following the same general procedures used for making biotin/anti-biotin measurements. The measured $K_D$ value was 0.45 nM, which was in excellent agreement with previous measurements made using labeled cholera toxin B (Shi, J. et al., J. Amer. Chem. Soc. 129:5954-5961, 2007. It should be noted that the isoelectric point of cholera toxin is close to pH 7.8 (Mekalanos, J. J., et al., Infec. Immun. 16:789-795, 1977). Therefore, the protein should possess a small net native charge at pH 8.2, which is the bulk pH value at which these measurements were made. The small absolute rise in fluorescence intensity observed upon saturation binding is consistent with this idea.

Figure 27:
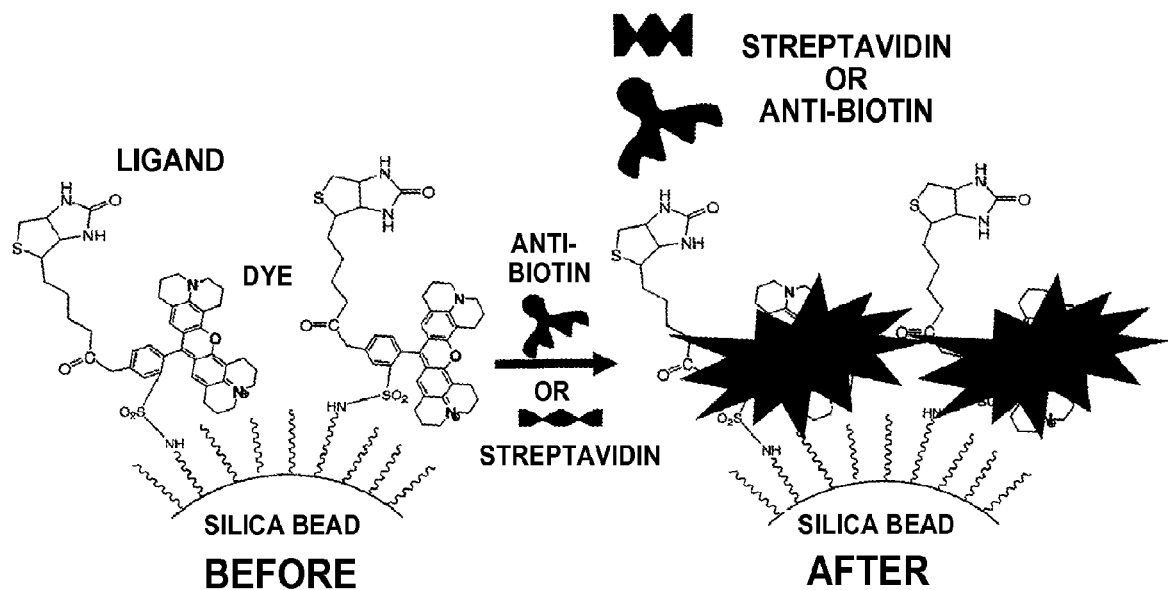
FIG. 27. The direct attachment of ortho-Texas Red® DHPE to both a surface (silica bead) and to a ligand (biotin) via attachment at the para position.
Figure 28:
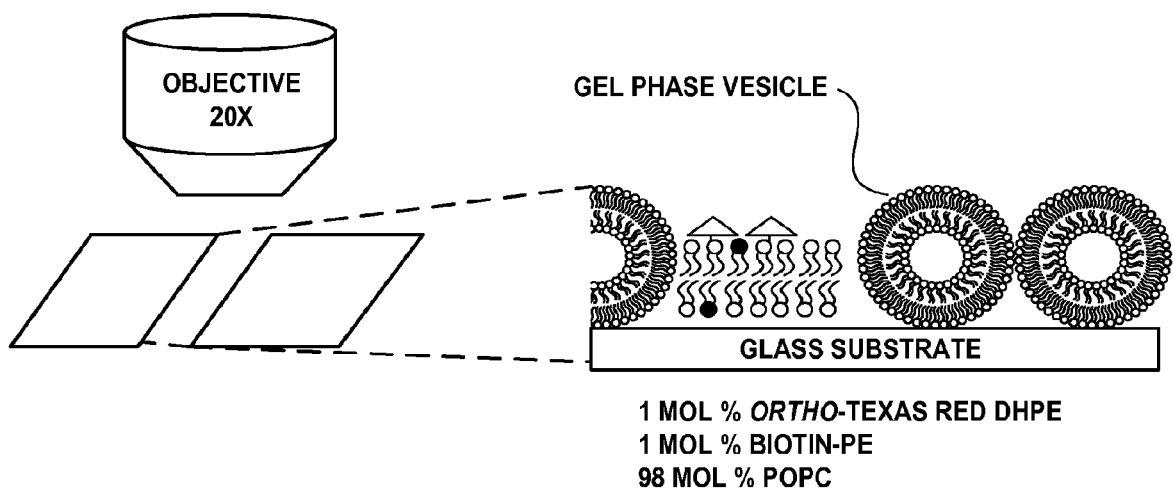
FIG. 28. Depiction of experiments using an increased amount of ortho-Texas Red® DHPE and an increased amount of immobilized ligand.
Figure 29A:
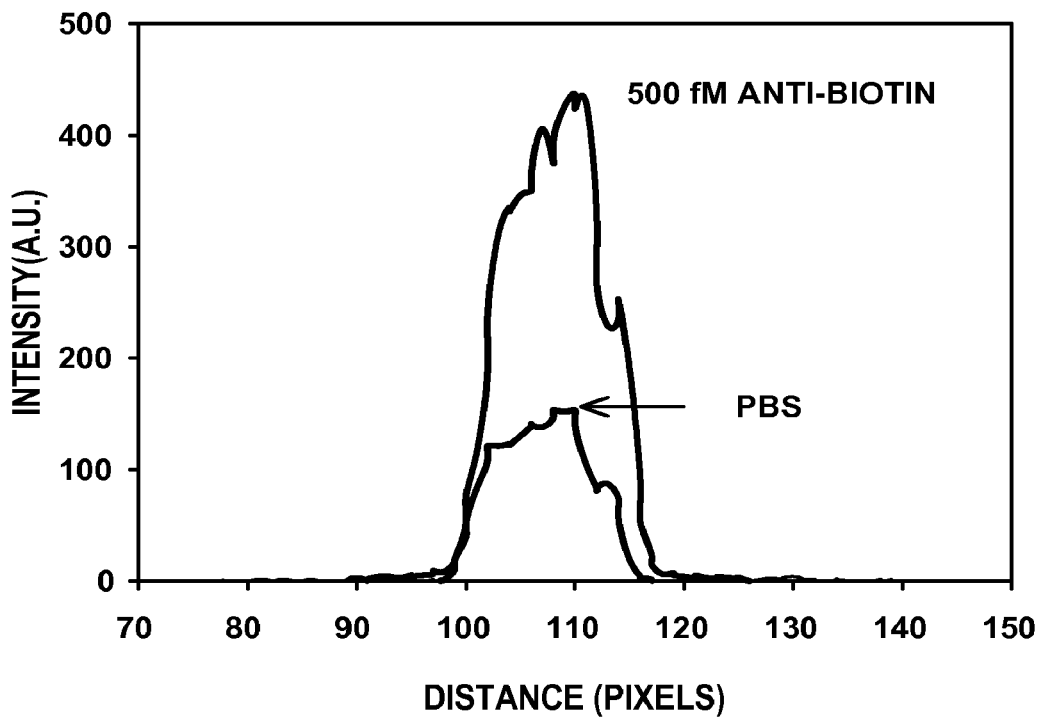
FIG. 29. Experimental line profile for the experimental condition of FIG. 28 and with 500 fM anti-biotin antibody in the bulk solution.
Figure 29B:
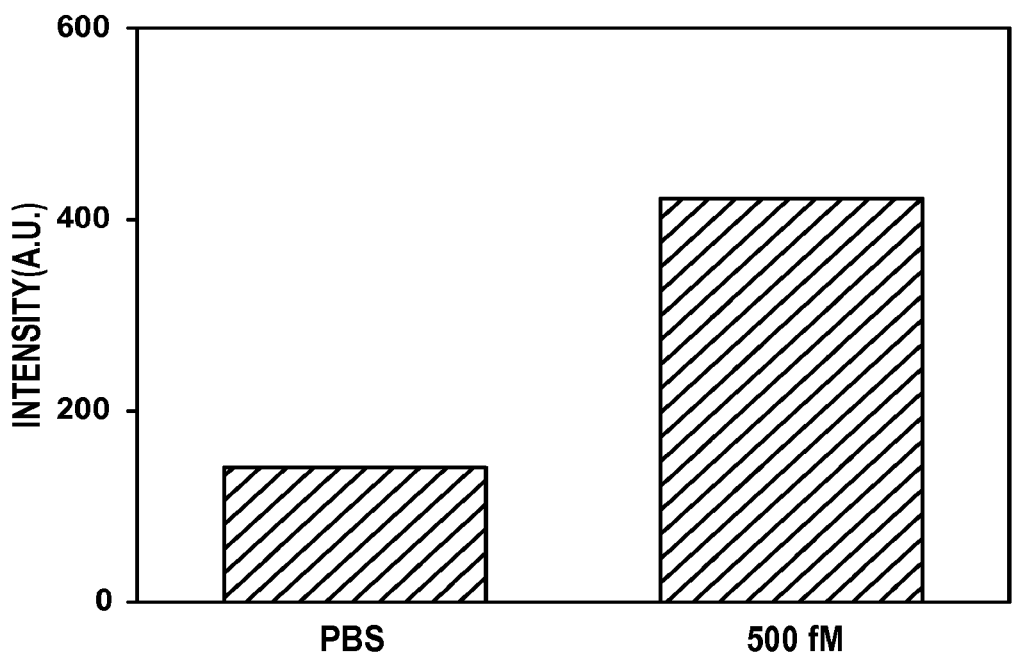

FIG. 27 shows the direct attachment of ortho-Texas Red® DHPE to both a surface (silica bead) and to a ligand (biotin) via attachment at the para position. This should greatly increase the sensitivity of the pH modulation assay because the ligand and dye are covalently linked together and therefore always in close proximity. This idea is not restricted to the use of ortho-Texas Red® as any pH sensitive dye could be substituted. Of course, any ligand could be substituted for biotin (e.g., sialic acid, 2,4-dinitrophenyl, RGD, ssDNA, etc.). Also, this idea is not restricted to the case of silica beads. The ligand-dye combination could be linked to any type of bead of any size. It could also be conjugated to a planar substrate (e.g., silica, glass, mica, sapphire). Some complication will arise near metal substrates because of fluorescence quenching. Finally, it is not even necessary to conjugate the sulfonamide to a surface. Simple termination (e.g., with a methyl group) will still allow the pH modulation behavior to occur. As a consequence, this system could even be used in bulk solution as a homogeneous fluorescence assay.

In addition to the direct attachment ideas shown in FIG. 27, both the ligand and the fluorophore shown here could be attached together to numerous scaffolds. For example both could be attached to a polymer as pendant groups. The detection ideas will remain identical.

In addition to being able to detect negatively charged proteins, experiments have also been performed showing that our pH modulation assay can detect positively charged proteins. In this case, the sensor works as a "turn off" rather than as a "turn on" sensor. To investigate this, the binding of avidin, which is a positively charged macromolecule, was studied. The conditions were similar to those described above except where explicitly stated. Under all conditions, a saturation concentration of avidin or streptavidin was employed (1 μM). The bilayers each contained 1 mol % biotin-PE and 0.03 mol % ortho-Texas Red® DHPE. See FIGS. 31-37.

Under these conditions, results showed that at pH 8.2, that this assay detects avidin in a turn off mode. It does not detect streptavidin under these conditions because the protein is almost exactly at its isoelectric point at the surface. However, upon adding 20 mol % DOPS (a negatively charged lipid) to the membrane, the assay was rerun at pH 9.25. Under these conditions, it detects avidin in a "turn off" mode and streptavidin in a "turn on" mode.

It should be noted that the effective pH at the interface is about a unit lower than the pH of the bulk solution under all conditions. This is because the underlying glass substrate in these assays is negatively charged and therefore attracts hydronium ions even in the absence of bound proteins.

The pH modulation detection assay is amenable monitoring protein-small molecule and protein-protein interactions homogeneously in aqueous solution. As a demonstration, the binding of biotin (vitamin B7) to avidin conjugated with ortho-Texas Red® succinimidyl ester was monitored in two parallel rectangular glass capillary tubes (0.1 mm×1.0 mm inner diameter) as shown in FIG. 38.

Avidin was labeled with Texas Red® succinimidyl ester as follows: The ortho isomer of Texas Red® succinimidyl ester was separated from the para isomer via thin layer chromatography utilizing silica plates (TLC Silica Gel 60 F254, EMD Chemicals) and 8:92 (methanol:chloroform) solvent. The separated band was removed from the plates with a razor and the ortho-Texas Red® succinimidyl ester was eluted from the silica with the same methanol/chloroform solvent. The dye (21 μg) was dried down with nitrogen in a 2 mL reactive vial containing a magnetic stir bar. To this reaction vial was added 0.5 mL of a 2 mg/mL avidin solution in 1 M sodium bicarbonate. This solution was allowed to stir for two hours at room temperature before being separated in a column containing Bio-Rad BioGel® Fine size purification resin in phosphate buffered saline (PBS, 10 mM potassium phosphate, 150 mM NaCl, 2 mM sodium azide, pH 7.2). This PBS was utilized as the elution buffer as well. The collected Texas-Red® succinimidyl ester-labeled avidin was utilized in the sensing experiments.

The two rectangular capillaries were passivated with a surface coating of bovine serum albumin (BSA). The BSA was then thoroughly rinsed away with phosphate buffered saline (10 mM $Na_2HPO_4$, 150 mM NaCl, pH 7.0). Next, a 3 μM solution of ortho-Texas Red® succinimidyl ester conjugated avidin was introduced in PBS into both capillaries. The right capillary additionally contained a 200 μM concentration of biotin (vitamin B7). A line scan across the micrograph is shown on the right. As can be seen, the fluorescence intensity is approximately a factor of five higher in the capillary that also contains the saturation concentration of biotin. It should be noted that avidin is a positively charged protein and the biotin is natively charged in solution near pH 7.0. Therefore, the local pH near the protein surface is lowered when the small molecule binds.

Figure 38A:
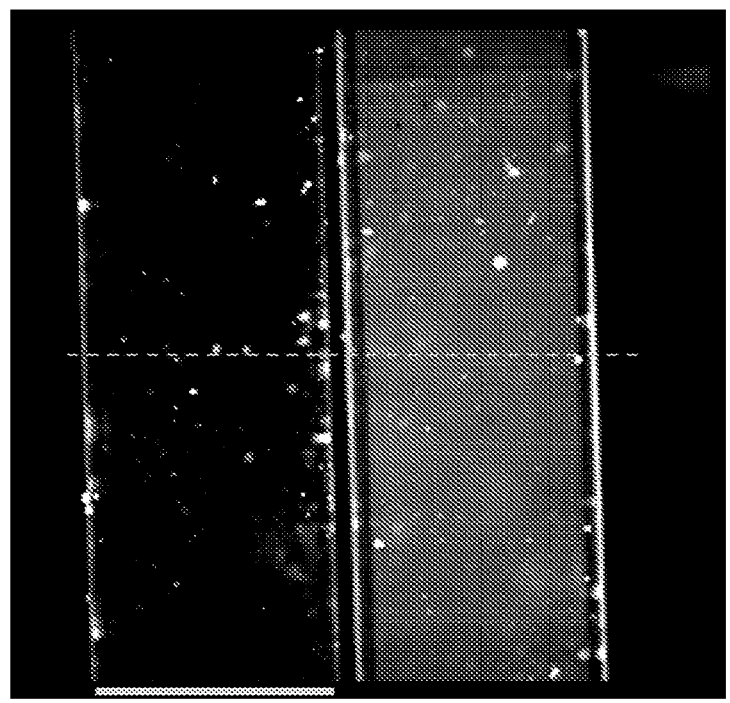
FIG. 38. Binding of biotin to avidin conjugated with ortho-Texas Red® succinimidyl ester. (a) Fluorescence micrograph of two rectangular capillary tubes (0.1 mm×1.0 mm inner diameter). The light gray bar line at the lower left is 1 mm. (b) Line scan from the dashed line from the image.
Figure 38B:
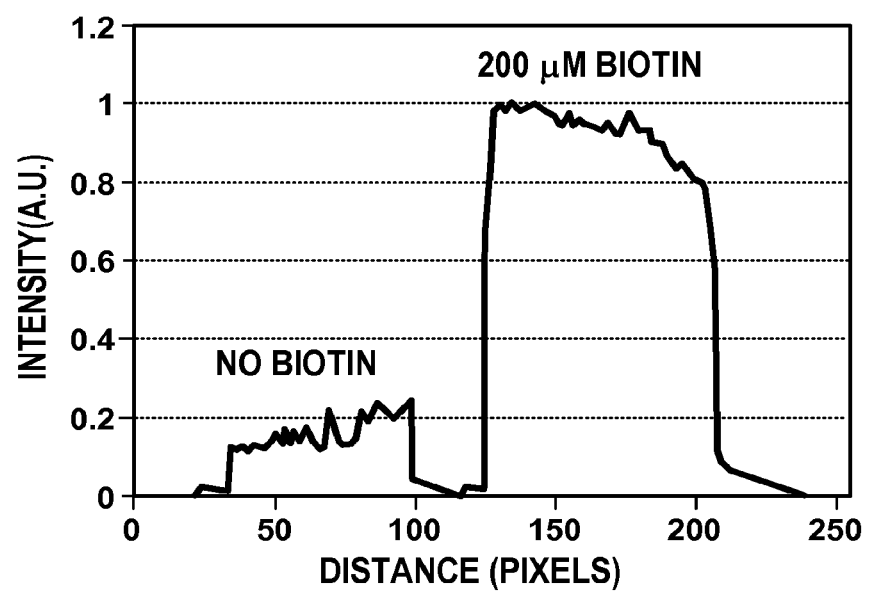
Figure 39A:
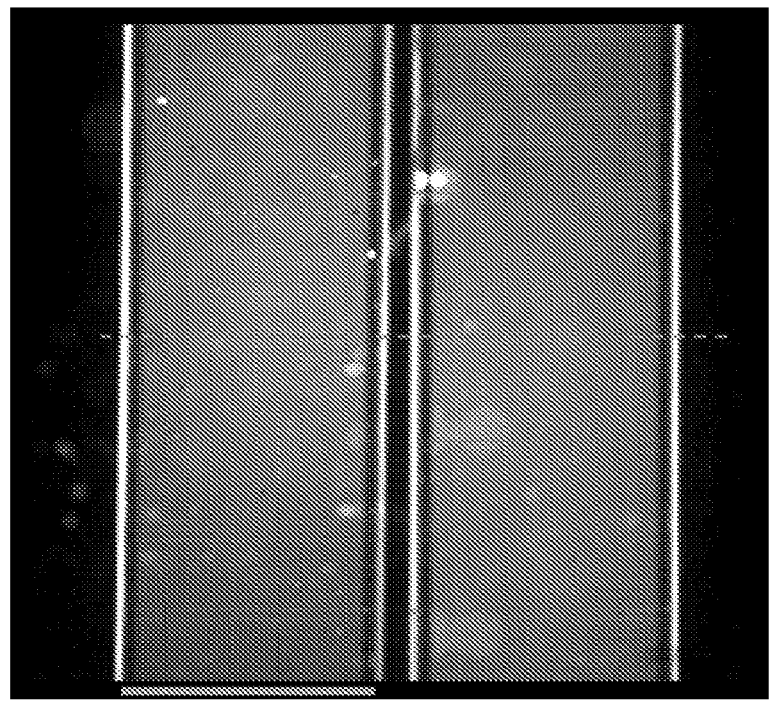
FIG. 39. Binding of biotin to avidin conjugated with para-Texas Red® succinimidyl ester. (a) Fluorescence micrograph of two rectangular capillary tubes (0.1 mm×1.0 mm inner diameter). The light gray bar line at the lower left is 1 mm. (b) Line scan from the dashed line from the image.
Figure 39B:
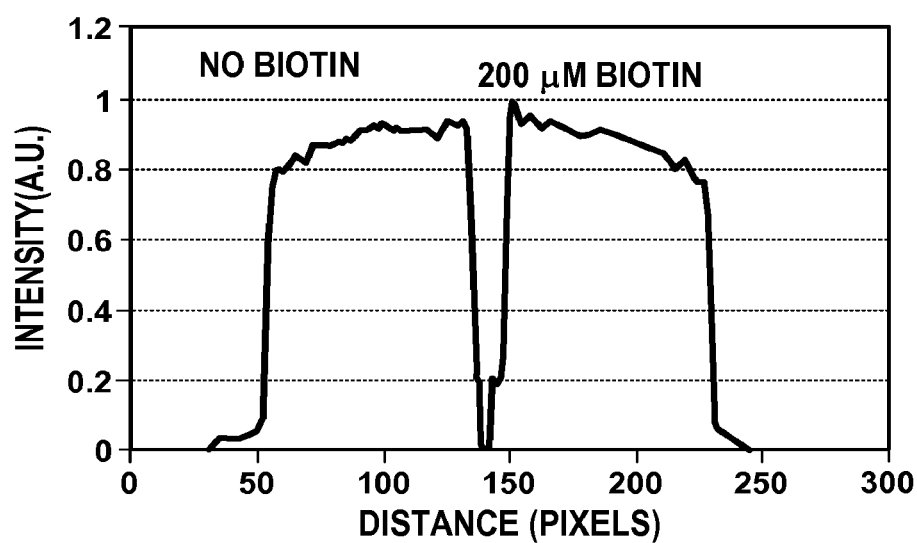

As a control, the same set of experiments was run as in FIG. 38. However, this time the avidin was conjugated with para-Texas Red® succinimidyl ester (FIG. 39). As can be seen, there was little if any fluorescence difference between the two capillary tubes. This is in spite of the fact that a saturation concentration of biotin should be bound to the protein in the right capillary tube.

Figure 40A:
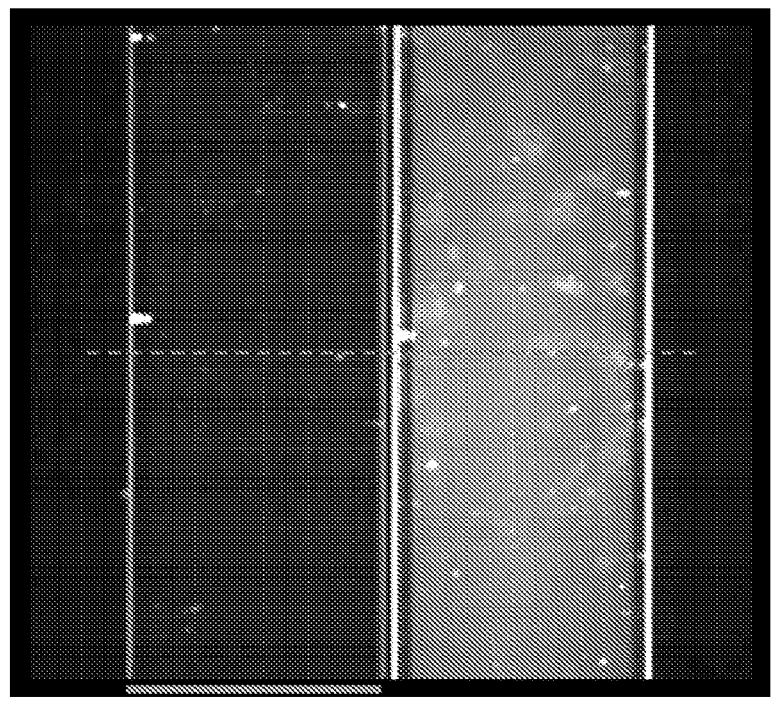
FIG. 40. Protein-protein interactions studied with BSA and avidin conjugated with ortho-Texas Red® succinimidyl ester. (a) Fluorescence micrograph of two rectangular capillary tubes (0.1 mm×1.0 mm inner diameter). The light gray bar line at the lower left is 1 mm. (b) Line scan from the dashed line from the image.
Figure 40B:
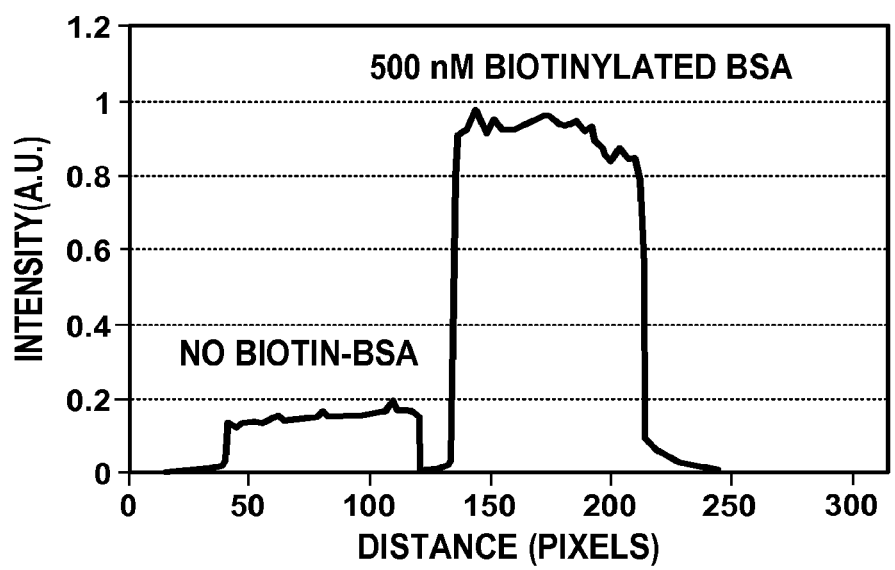

In another set of experiments, protein-protein interactions were investigated homogeneously in the same PBS buffer solution (FIG. 40). The two rectangular capillaries were passivated with a surface coating of bovine serum albumin (BSA). The BSA was then thoroughly rinsed away with phosphate buffered saline (10 mM $Na_2HPO_4$, 150 mM NaCl, pH 7.0). Next, a 3 μM solution of ortho-Texas Red® succinimidyl ester conjugated avidin was introduced in PBS into both capillaries. The right capillary additionally contained 500 μM biotinylated bovine serum albumin (BSA). A line scan across the micrograph is shown on the right. As can be seen, the fluorescence intensity is approximately a factor of eight higher in the capillary that also contains the saturation concentration of biotin. BSA is negatively charged under these conditions. Therefore, it is expected that the local pH around the avidin is lowered upon binding of the biotinylated BSA.

It is also noted that ortho-Texas Red® may be directly attached to a protein or other receptor molecule via the para position. If the protein or other receptor molecule has a ligand binding site, then this method could be employed to detect small molecule or ion binding. For example, charged ligands or ions will directly modulate the local pH. An example is the binding of $Ca^{2+}$ to calmodulin.

Methods described herein also be employed with uncharged receptors or ligands. For example, the binding of a ligand to a protein will cause allosteric rearrangement to the macromolecule, even if the ligand has a net neutral charge. This will in turn slightly modulate the local pH around the attached pH sensitive dye. Thus, methods described herein may pertain to fluorescence detection as induced by allosteric changes upon a receptor-ligand binding event.

Methods described herein may be performed homogeneously in bulk solution or on a support if the protein or other receptor molecule is directly attached to it. Methods described herein may work with other pH sensitive dyes having photobleaching resistance properties, as discussed herein.

As will be understood by those skilled in the art who have the benefit of the instant disclosure, other equivalent or alternative compositions, devices, methods, and systems can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. In addition, the size of a bead, biosensor, and/or assay may be scaled up or down to suit the needs and/or desires of a practitioner. Also, where ranges have been provided, the disclosed endpoints may be treated as exact and/or approximations as desired or demanded by the particular embodiment. In addition, it may be desirable in some embodiments to mix and match range endpoints. A bead, biosensor, and/or assay may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims. Thus, while illustrative embodiments have been illustrated and described, it will be appreciated that various changes can be made therein without departing from the spirit and scope of the invention.

What is claimed is:

1. A substrate comprising:
   (a) an ortho-sulforhodamine 101-conjugate; and
   (b) a ligand or a receptor,
   wherein the substrate is substantially free of para-sulforhodamine 101-conjugate.

2. The substrate of claim 1, wherein the substrate is planar.

3. The substrate of claim 1, wherein the substrate comprises plastic, glass, silica, mica, sapphire, a polymer, or an oxide, or a combination thereof.

4. The substrate of claim 3, wherein the substrate comprises a polymer.

5. The substrate of claim 4, wherein the polymer is polydimethylsiloxane.

6. The substrate of claim 3, wherein the substrate comprises glass.

7. The substrate of claim 1, wherein the substrate comprises a semiconductor.

8. The substrate of claim 1, wherein the substrate comprises a lipid.

9. The substrate of claim 1, wherein the substrate comprises a supported lipid bilayer.

10. The substrate of claim 1, wherein the substrate is free of other fluorophore or fluorophore-containing conjugate.

11. The substrate of claim 1, wherein the substrate is a well of a multi-well plate.

12. The substrate of claim 1, wherein the substrate is a surface of a microfluidic device.

13. The substrate of claim 1, wherein the substrate is further defined as a bead.

14. The substrate of claim 13, wherein the bead is a silica bead or a polystyrene bead.

15. The substrate of claim 13, wherein the diameter of the bead ranges from about 0.05 μm to about 100 μm.

16. The substrate of claim 13, wherein the bead is substantially covered by a coating.

17. The substrate of claim 16, wherein the coating is a protein-resistant coating.

18. The substrate of claim 17, wherein the protein-resistant coating comprises zwitterionic lipids.

19. The substrate of claim 17, wherein the protein-resistant coating comprises polyethyleneglycol (PEG).

20. The substrate of claim 17, wherein either the ligand or the receptor is immobilized on the coating.

21. The substrate of claim 16, wherein the ortho-sulforhodamine 101-conjugate is immobilized on the coating.

22. The substrate of claim 1, wherein the ortho-sulforhodamine 101-conjugate comprises the ligand or receptor to form an ortho-sulforhodamine 101-labeled ligand or an ortho-sulforhodamine 101-labeled receptor.

23. The substrate of claim 22, wherein the ortho-sulforhodamine 101-conjugate comprises the receptor to form an ortho-sulforhodamine 101-labeled receptor.

24. The substrate of claim 1, wherein the ortho-sulforhodamine 101-conjugate is covalently bound to the substrate.

25. The substrate of claim 24, wherein the ortho-sulforhodamine 101-conjugate is covalently bound to the substrate and to either the ligand or the receptor.

26. The substrate of claim 1, wherein the ortho-sulforhodamine 101-conjugate comprises a lipid.

27. The substrate of claim 1, wherein the ortho-sulforhodamine 101-conjugate is further defined as ortho-sulforhodamine 101-DHPE.

28. The substrate of claim 1, wherein the ortho-sulforhodamine 101-conjugate comprises a polymer.

29. The substrate of claim 1, wherein the ortho-sulforhodamine 101-conjugate comprises PEG.

30. A substrate comprising:
(a) a para-sulforhodamine 101-conjugate; and
(b) a ligand or a receptor,
wherein the substrate is substantially free of ortho-sulforhodamine 101-conjugate.

31. A substrate comprising:
(a) an ortho-sulforhodamine 101-conjugate;
(b) a para-sulforhodamine 101-conjugate; and
(c) a ligand or a receptor,
wherein the ortho-sulforhodamine 101-conjugate and the para-sulforhodamine 101-conjugate are optically separated.

32. A bead having a coating, wherein the coating comprises a surface that comprises an ortho-sulforhodamine 101-conjugate, wherein the bead is substantially free of para-sulforhodamine 101-conjugate.

33. The bead of claim 32, wherein the ortho-sulforhodamine 101-conjugate is covalently bound to the coating.

34. The bead of claim 32, wherein the coating comprises PEG.

35. The bead of claim 32, wherein the coating further comprises a first ligand or a first receptor.

36. The bead of claim 35, wherein the first ligand or the first receptor is covalently bound to the coating.

37. The bead of claim 32, wherein the ortho-sulforhodamine 101-conjugate is covalently bound to the coating and covalently bound to a first ligand or a first receptor.

38. A bead having a coating, wherein the coating comprises a surface that comprises a para-sulforhodamine 101-conjugate, wherein the bead is substantially free of ortho-sulforhodamine 101-conjugate.

39. A system for detecting receptor-ligand binding, comprising:
(a) a multi-well plate; and
(b) a bead as in claim 32 or claim 38.

40. The system of claim 39, comprising a bead of claim 32 and a bead of claim 38.

41. The system of claim 39, wherein the system is configured to detect binding of a minimum of about 50 molecules per pixel.

42. The system of claim 39, wherein the system is configured to detect binding of a minimum of about 1 part in 3,000,000 of the receptor-ligand $K_d$.

43. The system of claim 39, wherein the system is configured to operate within a pH range of about 2 to about 13.

44. A microfluidic device comprising at least two channels, wherein one channel comprises an ortho-sulforhodamine 101-conjugate wherein the one channel is substantially free of para-sulforhodamine 101-conjugate, and
a second channel comprises a para-sulforhodamine 101-conjugate wherein the second channel is substantially free of ortho-sulforhodamine 101-conjugate.

45. The microfluidic device of claim 44, wherein the ortho-sulforhodamine 101-conjugate is covalently bound to the surface of one channel, and the para-sulforhodamine 101-conjugate is covalently bound to the surface of the second channel.

46. The microfluidic device of claim 44, wherein a bead of claim 32 is immobilized on the surface of one channel, and a bead of claim 38 is immobilized on the surface of the second channel.

47. A method of detecting binding between a non-fluorescently labeled receptor and a non-fluorescently labeled ligand, comprising:
obtaining a first fluorescence measurement associated with a substrate comprising both a pH-sensitive fluorophore and the non-fluorescently labeled receptor, wherein the pH-sensitive fluorophore is an ortho-sulforhodamine 101-conjugate;
introducing a solution comprising the non-fluorescently labeled ligand to the substrate; and
obtaining a second fluorescence measurement, wherein a change in fluorescence between the first and second measurements is indicative of binding.

48. The method of claim 47, further comprising a para-sulforhodamine 101-conjugate as a reference.

49. The method of claim 47, further comprising covalently binding the receptor to the substrate.

50. The method of claim 47, wherein the method is further defined as a high throughput screening method.

51. A method of detecting binding between a non-fluorescently labeled ligand and a non-fluorescently labeled receptor, comprising:
obtaining a first fluorescence measurement associated with a substrate comprising both a pH-sensitive fluorophore and the non-fluorescently labeled ligand, wherein the pH-sensitive fluorophore is an ortho-sulforhodamine 101-conjugate;
introducing a solution comprising the non-fluorescently labeled receptor to the substrate; and
obtaining a second fluorescence measurement, wherein a change in fluorescence between the first and second measurements is indicative of binding.

52. The method of claim 51, further comprising a para-sulforhodamine 101-conjugate as a reference.

53. The method of claim 51, further comprising covalently binding the ligand to the substrate.

54. A method of detecting binding between a ligand and a receptor, comprising:
obtaining a first fluorescence measurement of a first solution comprising a ortho-sulforhodamine 101-labeled receptor, wherein the solution is substantially free of para-sulforhodamine 101-conjugate;
introducing a second solution comprising a ligand; and
obtaining a second fluorescence measurement, wherein a change in fluorescence between the first and second measurements is indicative of binding.

55. The method of claim 54, further comprising employing para-sulforhodamine 101-conjugate as a reference.

56. A method of determining whether the ligand of a substrate of claim 1 binds to a cognate receptor or whether the receptor of a substrate of claim 1 binds to a cognate ligand, the method comprising:
    obtaining a first fluorescence measurement associated with the substrate of claim 1;
    introducing the substrate to a bulk aqueous solution comprising a cognate receptor or cognate ligand; and
    obtaining a second fluorescence measurement, wherein a change in fluorescence between the first and second measurements is indicative of binding.

57. The method of claim 56, further comprising employing the para-sulforhodamine 101-conjugate as a reference.

58. The method of claim 56, further comprising immobilizing the ortho-sulforhodamine 101-conjugate onto the substrate.

59. The method of claim 56, further comprising immobilizing either the ligand or receptor onto the substrate.

60. A method of determining a kinetic measurement of a receptor-ligand binding event comprising contacting an ortho-sulforhodamine 101 labeled protein with a ligand, wherein $k_{on}$ for the binding event is determined.

* * * * *